(12) United States Patent
Kelley et al.

(10) Patent No.: US 9,284,554 B2
(45) Date of Patent: Mar. 15, 2016

(54) MICRO-RNA SCAFFOLDS AND NON-NATURALLY OCCURRING MICRO-RNAS

(71) Applicant: GE Healthcare Dharmacon, Inc., Lafayette, CO (US)

(72) Inventors: Melissa Kelley, Lafayette, CO (US); Amanda Birmingham, Lafayette, CO (US); Jon Karpilow, Boulder, CO (US); Anastasia Khvorova, Northborough, MA (US); Kevin Sullivan, Boulder, CO (US)

(73) Assignee: GE Healthcare Dharmacon, Inc., Lafayette, CO (US)

( * ) Notice: Subject to any disclaimer, the term of this patent is extended or adjusted under 35 U.S.C. 154(b) by 0 days.

(21) Appl. No.: 14/447,359

(22) Filed: Jul. 30, 2014

(65) Prior Publication Data
US 2014/0336242 A1 Nov. 13, 2014

Related U.S. Application Data

(62) Division of application No. 12/601,508, filed as application No. PCT/US2008/064462 on May 22, 2008.

(60) Provisional application No. 60/939,785, filed on May 23, 2007.

(51) Int. Cl.
| | |
|---|---|
| *C12N 15/11* | (2006.01) |
| *C12Q 1/68* | (2006.01) |
| *C12N 15/113* | (2010.01) |
| *C07H 21/04* | (2006.01) |

(52) U.S. Cl.
CPC ............ *C12N 15/113* (2013.01); *C12N 15/111* (2013.01); *C12Q 1/6869* (2013.01); *C12N 2310/141* (2013.01); *C12N 2310/531* (2013.01); *C12N 2320/30* (2013.01); *C12N 2330/30* (2013.01)

(58) Field of Classification Search
CPC ............................. C12N 15/111; C12N 15/113
See application file for complete search history.

(56) References Cited

U.S. PATENT DOCUMENTS

| | | | |
|---|---|---|---|
| 2006/0185027 | A1 | 8/2006 | Bartel et al. |
| 2007/0044164 | A1 | 2/2007 | Dickins et al. |
| 2007/0113302 | A1 | 5/2007 | Huang et al. |
| 2010/0256222 | A1 | 10/2010 | Kelley et al. |

FOREIGN PATENT DOCUMENTS

| | | |
|---|---|---|
| WO | 2004045543 | 6/2004 |
| WO | 2004076622 | 9/2004 |
| WO | 2005118806 | 12/2005 |
| WO | 2008147837 | 12/2008 |
| WO | 2008147839 | 12/2008 |

OTHER PUBLICATIONS

Ambros, Victor et al., A Uniform System for microRNA Annotation, RNA, A Publication of the RNA Society, 2003 9: 277-279.
European Search Report PCT/US2008064462. Sep. 22, 2011.
European Search Report PCT/US2008064458. Sep. 22, 2011.
Daqian Sun, et al. Multi-miRNA Hairpin Method that Improves Gene Knockdown Efficiency and Provides Linked Multi-gene Knockdown. Biotechniques, vol. 41, No. 1, Jul. 2006, pp. 59-63.
Jing Qu, et al. Artificial MicroRNA-Mediated Virus Resistance in Plants. Journal of Virology,vol. 81. No. 12, Jun. 2007. p. 6690-6699.
Zenghron Li, et al. Inhibition of PRL-3 gene expression in gastric cancer cell line SGC7901 via microRNA suppressed reduces peritoneal metastasis. Biochemical and Biophysical Research Communications vol. 348, No. 1 (2006), pp. 229-237.
Jennifer H. Mansfield, et al. MicroRNA-responsive 'sensor' trans genes uncover Hox-like and other developmentally regulated patterns of vertebrate microRNA expression. Nature Genetics vol. 36, No. 10, Oct. 2004.
Yang Wang, et al. MicroRNA: past and present. Frontiers in Bioscience 12, 2316-2329, Jan. 1, 2007.
Olga Matveeva, et al. Comparison of approaches for rational siRNA design leading to a new efficient and transparent method. Nucleic Acids Research, vol. 35, No. 8, pp. e63-1. 2007.
Angela Reynolds, et al. Rational siRNA design for RNA interference. Nature Biotechnology, vol. 22, No. 3 (2004).
Li, Sung-Chou, et al., Intronic MicroRNA: Discovery and Biological Implications, DNA and Cell Biology, vol. 26, No. 4, 2007, pp. 195-207.
miRBank accession No. MI0000284 (Jul. 2003) retrieved on Nov. 20, 2009. http://microrna.sanger.ac.uk/cgi- bin/sequences/mirna_entry.pl?acc=MI0000284.
Zeng et al., Organic small hairpin RNAs (OshR): A do-it-yourself platform for transgene-based silencing, Methods 63 (2013) 101-109.
Shiba et al., published online on Apr. 25, 2007, Nucleic Acids Research, vol. 35, pp. 3287-3296.
Han et al, Molecular basis for the recognition of primary microRNAs by the Drosha-DGCR8 complex 2006, Cell vol. 125, pp. 887-901.
Zeng et al., Both natural and designed micro RNAs can inhibit the expression of cognate mRNAs when expressed in human cells, 2002, Molecular Cell, vol. 9, pp. 1327-1333.
Miyagishi et al., Optimization of an siRNA-expression system with an improved hairpin and its significant suppressive effects in mammalian cells, 20045, The Journal of Gene Medicine, vol. 6, pp. 715-723.

(Continued)

*Primary Examiner* — Dana Shin
(74) *Attorney, Agent, or Firm* — Dorf & Nelson LLP; Scott D. Locke, Esq.

(57) ABSTRACT

The present disclosure provides a non-naturally occurring miRNA having a stem-loop structure comprising a scaffold derived from a first endogenous miRNA (e.g., miR-196a-2 or miR-204), a mature strand derived from a second endogenous miRNA, and a star strand sequence that is at least partially complementary to the mature strand sequence. The present disclosure also provides a non-naturally occurring miRNA having a stem-loop structure comprising a scaffold derived from an endogenous miRNA (e.g., miR-196a-2 or miR-204), a mature strand designed to be at least partially complementary to a target RNA, and a star strand sequence that is at least partially complementary to the mature strand sequence. The methods and compositions of the disclosure may be used to mediate gene silencing via the RNAi pathway.

12 Claims, 37 Drawing Sheets

(56) References Cited

OTHER PUBLICATIONS

John et al., HUman microRNA targets, 2004, PLoS Biology, vol. 2, pp. 1862-1879.
Stem-Loop Sequence MI0000284, miRBase:Sequences [online] 2003 [retrieved on Sep. 28, 20008] Retrieved from the internet URL <http//micronrna.sangerac.uk/cgi-bin/seqeunces/mirna_entry.pl?acc=MI0000284>.
International Search Report for PCT/US08/64462, Oct. 7, 2008.
Written Opinion of the International Searching Authority, PCT/US08/64462, Oct. 7, 2008.
Griffiths-Jones, et al., microRNA sequences, targets and gene nomenclature, 2006, Nucleic Acids Research, 34: D140-144.
"Stem-loop sequence hsa-mir-196a-1," Accession No. MI0000239, 2003 retrieved from www.mirbase.org on Dec. 31, 2013.
"Stem-loop sequence hsa-mir-196a-1," Accession No. MI0000279, 2003 retrieved from www.mirbase.org on Dec. 31, 2013.
Lagos-Quintana et al., Identification of novel gene coding for small expressed RNAs, 2001, Science vol. 294, pp. 853-858.

Artificial Intron Sequence:

SEQ ID NO:1

5'splice site     *Spel*    *BglII*
5'-CAG/GTAAGTTAGTAGATAGATAGCCGTGCTATTT*actagt*CGT*agatct*ACAATGTTGAATTCTC Branch point   *poly pyrimidine tract*    3'splice site
ACGGCGGCCCGCTC*tactaac*CCTTCTTTCTTTCTCTTCCTTCATCTTTCAG/GCG 3'

Figure 4A miR-196a-2 w/ flanking sequence:

tcagacccctaccaccagcaacccaaagtctactctctagtccttagggaggttgt
gggggcggaaaggggggacggggctgaatttcttcccaaccccttccttctcctccaga
tagatgcaaagctgaatctcccgccctgctcgctcagctgatctgtggcttagtagtttcatgt
tgttggattgagttttgaactcggcaacaagaaactgcctgagttacatcagtcggttttcgtc
gagggccccaacctctccactcctcccagtgggactgcccactgcccctccc
agatagggcaagtgggtgagaccaaggaggacaagtgtgagtgggttgcagaacaagtctg
gagaaccctgcttatgccgtcctct

SEQ ID NO: 3

Figure 4C miR-26b w/ flanking sequence:

tggatacatgtggaatgtcagaggcccagagagggtgtgagacttgtcccaagtcaca
cagaacctcaagggcttgtgctgactccaagcctgcagagtggctctcctctaggctccccg
tgctgtgctccctcgccccacccctgcccgggaccccagttcaagtaattcaggataggttgtgc
tgtccagcctgtttctccattacttgctcggggaccgtgccctgcagccttggggtgaggggc
tgcccctggattcctgcactaggctgaggtttgaggcaggggaaggatttggaattagggacctc
gtgaggtaggactggccagtggagtggaagttttgatcgttttctggcgggggggtggtacagtt
tccccagcagtggtca
SEQ ID NO:4

Figure 4D miR-204 w/ flanking sequence:
tgagggtggaggcaagcagagaggacctcctgatcgtgtatccatagqacaggtgatgga
gaggggtggggttggaggcaagcagagaggcctcctgatcatttaccacagacaggtggtg
gagaggaggtgagggtggaggcaagcagagagqacctcctgatcatgtaccatagqacagggtga
tggagaggaggtggggtggaggtgaggcaagcagaggaccctcctgatcatgtaccatagqacaggt
gatgaaaggaggqtgggqtggaggtqaqgcaagcagagagqacttcctgatcgcgtaccatggctacag
tctttcttcatgtgactcgtggacttcccttgtcatcctatgcctgagaatatgaaggaggc
tgggaaggcaaagqgacgttcaattgtcatcactggcatcttttttgatcattgcaccatcatca
aatgcattggqataaccatgacatgaaattttccatcattggccataactgtccataagaga
gatgaaaacactatatgttaaaggtcatagtagaacttcatccaagcagctctggaattaggaa
ggagtgaaatatactctcaaagactaatagttctggqtccaa
SEQ ID NO:5

Figure 4E

M= mature strand
S= star strand miR-204 scaffold

```
       BlpI                        uca  ug ugac           uggac         gagcau
                                   •||  || ||||    ucg    ||•||                a
    5' GcUuAgcuacagucuuucu    —    ggu  ac acug    —      acuug                u
    3' cguCUcGaguuuuucuac     —      c  u          uua    ||•||                a
       SacI                                                uggac         ggaagu
```

SEQ ID NO: 12

Figure 6F

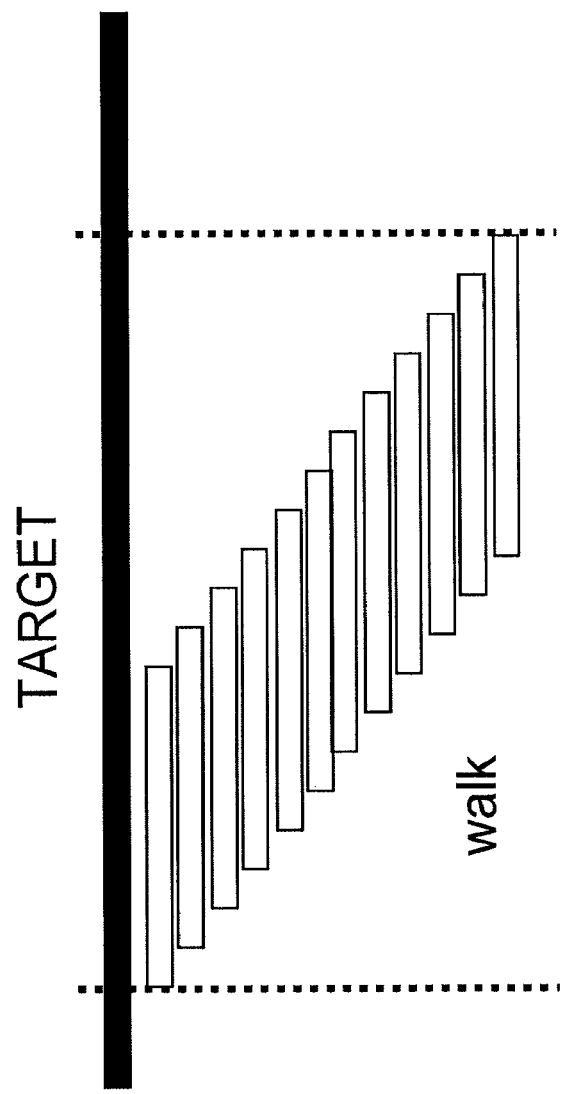

Reporter Insert For The GAPDH Walk ttCGTCATGGGTGTGAACCATGAGAAGTATGACAACAGCCTCAAGATCA
TCAGCAATGCCTCCTGCACCACCAACTGCTTAGCACCCCTGCCAAGG
TCATCCATGACAACTTTGgtatcgtggaaggactcatgaccacagtccatgccatcactgcc
accagaagactgtggatggcccctccgggaaactgtggcgtgatggccgc
SEQ ID NO:15

Figure 7B

CDC2 atggaagattataccaaaatagagaaattggagaagtacctatggagttgtataaggtagacacaaaactacagtcaagtgtagccatgaaaaat
cagactagaaagtgaagaggaaggggttcctagtactgcaatt<u>cggga</u>atttctcattaaggaacttcgtcatccaaatagtcagtcttcaggatgtgcttat
gcaggattcc<u>aggttatatctcatcttt<u>ga</u></u>gtttcttt<u>cc</u>atgg atctgaagaa<u>a</u>tactggattctcatccctgg<u>t</u>cagtacatgt <u>g</u>attcttca<u>c</u>ctgttaagagttattata
ccaaatcctacacaggattgtgttttgtcactctagaagagttcttcacagagactaaaacctcaaaatctcttgattgatgacaaggaacaattaaactggctgatt
ttggcctt gcagagctttggaatataccatcagatagtataacatgagtagtaacactctgtacagatctccagaagattgctgg ggtcagctcgttactcaact
ccagtt gacattggagtataggcaccacatatttgctgaactagcaactaagaaaccact tt ccatgggattcagaaatt gatcaactcttcag<u>gattt</u>cagagcttt
gggcactcccaataatgaagtgtggccagaagtggaatctggaaatc tt acagga ctataagaatacattt cccaaatgaaaccagagctagcatcccatgtcaaaa
acttggatgaaatgcttggatttgctctcgaaaatgttaatctatgatcagcaaacgaatttctggcaaaatggcactgaatcatcccatatttaatgatttgga
caatcagattaagagatgtag

SEQ ID NO:16

⬭ Top score for siRNA algorithm

▭ Top score for shRNA algorithm

Figure 9A

MapK1short (NM_002745)

CTACACCAACCTCTCGTACATCGGGCGAGGGCGCCTACGGCATGGTGTGCTCTGC
TTATGATAATGTCAACAAAGTTCGAGTAGCTATCAAGAAAATCAGCCCCTTTGAGC
ACCAGACCTACTGCCAGAGAACCCTGAGGGAGATAAAAATCTTACTGCGCTTCAG
ACATGAGAACATCATTGGAATCAATGACATTATTCGAGCACCAACCATCGAGCAA
ATGAAAGATGTATATATAGTACAGGACCTCATGGAAACAGATCTTTACAAGCTCTT
GAAGACACAACACCTCAGCAATGACCATATCTGCTATTTCTCTACCAGATCCTCA
GAGGGTTAAAATATATCCATTCAGCTAACGTTCTGCACCGTGACCTCAAGCCTTC
CAACCTGCTCACCACCACCTGTGATCTCAAGATCTGTGACTTTGGCCTGGCC
CGTGTTGCAGATCCAGATCACACAGGGTTCCTGACAGAATATGTGGCCA
CACGTTGGTACAGGGCTCCAGAAATTATGTGTTGGCATTCTGGCAGAATGCTTTCTAACAGGCCC
CATTGATATTTGGTCTGTAGGCTGCATTCTGGCAGAATGCTTTCTAACAGGCCC
ATCTTTCCAGGGAAGCATTACAAGAGACCTGAATTGTATAATAAATTTAAAAGCTAGGAACTATT
ATCCCCATCACAAGAGACCTGAATTGTATAATAAATTTAAAAGCTAGGAACTATT
TGCTTTCTCTTCCACACAAAAATAAGGTGCCATGGAACAGGCTGTTCCAAATGC
TGACTCCAAAGCTCTGGACTTATTGGACAAAATGTTGACATTCAACCCACACAAG
AGGATTGAAGTAGAACAGGCTCTGGCCCACCCATATCTGGAGCAGTATTACGACC
CGAGTGACGAGCCCATCGCCGAAGCACCATTCAAGTTCGACATGGAATTGGATG
ACTTGCCTAAG
SEQ ID NO: 17

Figure 9B

EGFR (NM_005228)

AATGGGTAAGTACATCAAGAGCTTCGTGGAGCGCGTGCTGAAGAACGAGCAGTAATTC
TAGGCGATCGCTCGAGAGCAGCAGCGATGCGACCCTCCGGGACGCCGGGGCAGCGCTC
CTGGCGCTGCTGGCTGCGCTCTGCCCGGCGAGTCGGGCTCTGGAGGAAAAGAAAGTT
TGCCAAGGCACGAGTAACAAGCTCACGCAGTTGGGCACTTTTGAAGATCATTTCTCA
GCCTCCAGAGGATGTTCAATAACTGTGAGGTGGTCCTTGGGAATTTGGAAATTACCTAT
GTGCAGAGGAATTATGATCTTTCCTTCTTAAAGACCATCCAGGAGGTGGCTGGTTATGT
CCTCATTGCCCTCAACACAGTGGAGCGAATTCCTTTGGAAAACCTGCAGATCATCAGA
GGAAATATGTACTACGAAAATTCCTAGCAGTCTTATCTAACTATGATGCAAAT
AAACCGGACTGAAGGAGCTGCCCATGAGAAATTACAGGAAATCCTGCATGGCGCCG
TGCGGTTCAGCAACAACCCTGCCCTGTGCAACATGTGGAGAGCATCCAGTGGCGGACA
TAGTCAGCAGTGACTTTCTCAGCAACATGTCGATGACTTCCAGACCACCTGGGCAG
CTGCCAAAGTGTGATCCAAGCTGTCCCAATGGGAGCTGCTGGGGTGCAGGAGAGGA
GAACTGCCAGAAACTGACCAAAATCATCTGTGCCCAGCAGTGCTCTCCGGCGCTGCCG
TGGCAAGTCCCCCAGTGACTGCTGCCAGTGCTGCTGCAGGCTGCACAGGCCC
CCGGGAGAGCGACTGCCTGGTCTGCCGCAAATTCCGAGAGAAGCCACGTGCAAGGA
CACCTGCCCCCCACTCATGCTCTACAACCCCACCACTGCGTGAAGATGGATGTGAACCCC
GAGGGCAAATACAGCTTTGGTGCCACCTGCGTGAAGAAGTGCCCCCGTAATTATGTGG
TGACAGATCACGGCTCGTCGTGGGCCGACAGTGTGGGCCGAGCTATGAGATGGAGG
AAGACGGCGTCCGCAAGTGTAAGAAGTGCGAAGGGCCTTGCCGCAAAGTGTGTAACG
GAATAGGTATTGGTGAATTTAAAGACTCACTCTCCATAAATGCTACGAATATTAAACACT
TCAAAAACTGCACCTCCATCAGTGGCGATCCACATCCTGCCGGTGGCATTTAGGGG
TGGCTCCTTCACACATACTCCTCCTCTGGATCCACAGGAACTGGATATTCTGAAAGCG
TAAAGGAAATCACAGG

SEQ ID NO: 18

Figure 9C

ZAP70

ATGCCAGACCCCGGGGCGCCACCTGCCCTGCCCCTTCTTCTAGCAGCATCTCGCGTGCCGAGGCCGAGGAGCACCTGA
AGCTGGGGCATGGCGGACGGGCTCTTCCTGCTGCGCCAGTGCTGCGCTGCCTGGGCGCTGGGCGCTATGTGCTGTC
GCTCGTGCACGATGTGCGCTTCCACCACTTCCCATCGAGCGCCAGCTCAACGGCACCTACGCCATTGCCGGCG
GCAAAGCCACTGTGGACCGGCAGAGCTCTGCGAGTTCTACTCGCGGACCGGGCTGCCCTGCAACCT
GCGCAAGCCGTGCAACGGCCGTCGGGCGCCTCGGCGCCTCGGGCGCCGGGGTCTTCGACTGCCCTGCGAGACGCCAT
GGTGCCTGACTACCGTGCGCCAGACGTGGAAGCTGGAGGGCGAGGGCAGGGCCATCATCAGCCAGGCC
CCGCAGGTGGGAGAAGCTCATTGCTACGACGGCCCACGAGCGGATGCCCTGGTACCACAGCAGCCTGACGCGTG
AGGAGGCCGAGCGAGCGCAAACTTTACTCTGGGGCGCAGACCGCAAGTTCCTGCTGAGGCCGCGGAAGGAGCA
GGGCACATACGCCCTGTCCCTCATCTATGGGAAGACGGTGTACCACTACCTCATCAGCCAAGACAAGGCGGGCA
AGTACTGCATTCCCGAGGGCACCAAGTTTGACACGCTCTGGCAGCTGGTGGAGTATCTGAAGCTGAAGGCGGAC
GGGCTCATCTACTGCCTGAAGGAGCCTGACTTCCACCATCCACGTTGACTCATCCTCAGAGACGAATCGACACCC
CACTCCAGCCCACCCATCACGTCCCCAGACAAACGTCCCAGACAAGAAGCTCTTCCTGAAGCCGATAACCTCTCATAGCTGACATTGA
CTACAGCGACCCAGAGGAGCTCAAGGACGGCAACTTTGGCTCAGTGCGCCAGGGCGTGTACCGGATGCGCAAGAAGCAGATCGACGTGGCCA
TCAAGGTGCTGAAGCAGGCCACGGAGAAGGCAGACAAGCGGAGGCGAGATCATGCACCA
GCTGGACAACCCCTACATCGTGCGGCTCATTGGGGTCTGCCAGGCCGAGCCCATCTATGGCCGAGCT
CTGGGGGCCGCGCTCACAAGTTCCTGGCGCAGCGGAGGAGAACTTTGCCCTCTCCAAAGCACTGGGTGCCGACGAC
ACGTCCTGCTGGTTAACCGGCACTACCGCCAAGATCAGCGACTCAGTGGTACGCACCCGAATGCATCAACTTCCGCAA
AGCTACTACACTGCCCCCGCTCAGCAGGAAGTGGCCGCTCAAGTGGTACCATGTGGGAGGCCTTGTCCTACGGCC
GTTCTCCAGCGCGGAGATGTCTGGAGCTATGGCCTTCATGAGCCAAGCAAGCAAGCGGATGAGTGCCCACCAGAGTG
ACAAGAAGATGAAAGGCCGGCACTGTACGGACTCATGATGACTGAGTGACTCGATGCCGGAGGATCGCCCGACTTCCTGACCGT
TCCACCCGAACTGTACGCACTCATGAGTACGACCTGTTACTACAGCCTGGCCAGCAAGGTGGAAGGGCCCCAGGCAGCAGCACACAGAAG
GCTGAGGCTGCCTGTGCCTGA

SEQ ID NO:19

Figure 9F

TGATCTGTGGCTTGGCGTAGTGCCGGTTAACGGATTGAGTTTGAACTCGTTAACCCGCACTATGCCGAGTTACATCAGTCGGTTTCG SEQ ID NO:20
TGATCTGTGGCTTGCGTACGACTTGAGCGGCGGATTGAGTTTGAACTCGTCGTCGCTCTAGTGGTGCCGAGTTACATCAGTCGGTTTCG SEQ ID NO:21
TGATCTGTGGCTTGCGGAAGTTGATGCATTCGGATTGAGTTTGAACTCGGATGCAACAACTTCGCGAGTTACATCAGTCGGTTTCG SEQ ID NO:22
TGATCTGTGGCTTGCCGGAGCCAAGTTCAATGGGATTGAGTTTGAACTCGTTGAACATGGGCTGTGGGCGAGTTACATCAGTCGGTTTCG SEQ ID NO:23

Figure 9G

```
                               SEQUENCE LISTING

<160> NUMBER OF SEQ ID NOS: 115

<210> SEQ ID NO 1
<211> LENGTH: 118
<212> TYPE: DNA
<213> ORGANISM: Artificial
<220> FEATURE:
<223> OTHER INFORMATION: Intron

<400> SEQUENCE: 1
caggtaagtt agtagataga tagcgtgcta tttactagtc gtagatctac aatgttgaat      60
tctcacgcgg ccgcttacta acccttcttt tctttctctt cctttcatct ttcaggcg      118

<210> SEQ ID NO 2

<400> SEQUENCE: 2

000

<210> SEQ ID NO 3
<211> LENGTH: 401
<212> TYPE: DNA
<213> ORGANISM: Homo sapiens

<400> SEQUENCE: 3
tcagacccct tacccaccca gcaacccaaa gtctactctc tagtccttag ggaggttgtg      60
ggggcggaaa gggggacggg gctgaatttc ttccttcccc aaccccttc ccttctcctc     120 cagatagatg caaagctgaa tctcccccct gctcctcact gatctgtctt atatttcatg     180
ttgttgggat tgagttttga actcggcaac aagaaactgc ctgagttaca tcagtcgttt     240
tcgtcgagag ccccaaccca cctctcccac tcctacccte cccagtggga ctgccccact     300
gccccctccc agatagggca aagtgggtgc agaccaagga ggacaagctg tgagtgggt     360 tgcagaacaa gtctggagaa ccctgcttta tgccgtcctc t                         401

<210> SEQ ID NO 4
<211> LENGTH: 363
<212> TYPE: DNA
<213> ORGANISM: Homo sapiens

<400> SEQUENCE: 4
tggatacatg tggaatgtca gaggcccaga gagggtgtga gacttgtccc aaagtcacac      60
agaacctcaa gggcttgtgc tgactccaag cctgcagagt gggctcctcc tctaggctcc     120
cccgtgctgt gctccctcgc cccaccctcc cattcccaca agtaattcaw ataggttgtg     180
tgcttccacc tttctccatt acttctcacc aggggctgc ccctggattc ctgcactagg     240
ctgaggttga ggcaggggaa gggattggga attagggacc tcgtgaggta ggactggcca     300
gtggagtgga agttttgatc gttttctggc gggggtggg tacagtttcc ccagcagtgg     360
tca                                                                   363

<210> SEQ ID NO 5
<211> LENGTH: 585
<212> TYPE: DNA
<213> ORGANISM: Homo sapiens

<400> SEQUENCE: 5
```

-continued

```
tgagggtgga ggcaagcaga ggacctcctg atcgtgtatc cataggacag ggtgatggag      60
aggagggtgg ggttggaggc aagcagaggg cctcctgatc atttacccac aggacagggt     120
ggtggagagg agggtgaggg tggaggcaag cagaggacct cctgatcatg tacccatagg     180
acagggtgat ggagaggagg gtggggtgg aggcaagcag aggacctcct gatcatgtac      240
ccataggaca gggtgataaa atgtggacaa aaacttccta tcctacccat tctttcttca     300
tgtgactcgt ggacttccct ttgtcatcct atgcctgaga atatatgaag gaggctggga     360
aggcaaagga cgttcaattg tcatcactgg catcttttt gatcattgca ccatcatcaa      420
atgcattggg ataaccatga catgaaattt tcatattggg ataatgtccc ataagagaga     480
tgaaaaacac tatatgttaa aggtcatagt agaacttcat ccaagcagct ctggaattag     540
gaaggagtga aatatactct caaagactaa tagttctggg tccaa                    585

<210> SEQ ID NO 6
<211> LENGTH: 91
<212> TYPE: RNA
<213> ORGANISM: Artificial
<220> FEATURE:
<223> OTHER INFORMATION: Reporter Silencing miR-26b

<400> SEQUENCE: 6
gcucagcccg ggacccaguu caaguaauuc aggauagguu gugugcuugc cagccuguuc      60
uccauuacuu ggcucgggag ccggagcucu g                                    91

<210> SEQ ID NO 7
<211> LENGTH: 132
<212> TYPE: RNA
<213> ORGANISM: Artificial
<220> FEATURE:
<223> OTHER INFORMATION: Reporter Silencing miR-204

<400> SEQUENCE: 7
gcuuagcuac agucuuucuu caugugacuc guggacuucc cuuugucauc cuaugccuga     60
gaauauauga aggaggcugg gaaggcaaag ggacguucaa uugucaucac uggcaucuuu     120
uuugagcucu gc                                                         132

<210> SEQ ID NO 8
<211> LENGTH: 136
<212> TYPE: RNA
<213> ORGANISM: Artificial
<220> FEATURE:
<223> OTHER INFORMATION: Endogenous B1pI miR-196a-2

<400> SEQUENCE: 8
gaaucucccg cccugcucgc ucagcugauc ucuggauuag guaguuucau guuguuggga      60
uugaguuuug aacucggcaa caagaaacug ccugaucuag aucagucggu uuucgucgag     120
ggccccaacc gagcuc                                                     136

<210> SEQ ID NO 9
<211> LENGTH: 136
<212> TYPE: RNA
<213> ORGANISM: Artificial
<220> FEATURE:
<223> OTHER INFORMATION: Endogenous B1pI miR-196A-2
```

```
<400> SEQUENCE: 9
gaaucucccg cccugcucgc ucagcugauc uguggcuuag guaguuucau guuguuggga      60
uugaguuuug aacucggcaa caagaaacug ccgaguacu aucagucggu uuucgucgag      120
ggccccaacc gagcuc                                                      136

<210> SEQ ID NO 10
<211> LENGTH: 106
<212> TYPE: RNA
<213> ORGANISM: Artificial
<220> FEATURE:
<223> OTHER INFORMATION: Reporter Sequence miR-196-a2
<220> FEATURE:
<221> NAME/KEY: misc_feature
<222> LOCATION: (25)..(43)
<223> OTHER INFORMATION: where x is any combination of A, C, G or T
<220> FEATURE:
<221> NAME/KEY: misc_feature
<222> LOCATION: (59)..(77)
<223> OTHER INFORMATION: where x is any combination of A, C, G or T

<400> SEQUENCE: 10
ugcucgcuca gcugaucugu ggcunnnnnn nnnnnnnnnn nnngauugag uuugaacnn       60 nnnnnnnnnn nnnnnnnagu uacaucaguc gguuucguc gagggc                     106

<210> SEQ ID NO 11
<211> LENGTH: 89
<212> TYPE: RNA
<213> ORGANISM: Artificial
<220> FEATURE:
<223> OTHER INFORMATION: Reporter Sequence miR-204
<220> FEATURE:
<221> NAME/KEY: misc_feature
<222> LOCATION: (18)..(36)
<223> OTHER INFORMATION: where n is any combination of A, C, G or T
<220> FEATURE:
<221> NAME/KEY: misc_feature
<222> LOCATION: (52)..(70)
<223> OTHER INFORMATION: where n is any combination of A, C, G or T

<400> SEQUENCE: 11
ucaugugacu cguggacnnn nnnnnnnnnn nnnnnngaga auauaugaag gnnnnnnnnn      60
nnnnnnnnnn guucaauugu caucacugg                                        89

<210> SEQ ID NO 12
<211> LENGTH: 88
<212> TYPE: RNA
<213> ORGANISM: Artificial
<220> FEATURE:
<223> OTHER INFORMATION: miR-204 scaffold

<400> SEQUENCE: 12
gcuuagcuac agucuuucuu caugugacuc guggagagaa uauaugaagg guucaauugu      60
caucacuggc aucuuuuug agcucugc                                          88

<210> SEQ ID NO 13
<211> LENGTH: 94
<212> TYPE: RNA
<213> ORGANISM: Artificial
<220> FEATURE:
<223> OTHER INFORMATION: miR-196a-2 scaffolds

<400> SEQUENCE: 13
gaaucucccg cccugcucgc ucagcugauc ucuggaugau ugaguuuuga acaucuagau      60
cagucgguuu ucgucgaggg ccccaaccga gcuc                                  94
```

```
<210> SEQ ID NO 14
<211> LENGTH: 94
<212> TYPE: RNA
<213> ORGANISM: Artificial
<220> FEATURE:
<223> OTHER INFORMATION: miR-196a-2 scaffolds

<400> SEQUENCE: 14
gaaucucccg cccugcucgc ucagcugauc uguggcugau ugaguuuuga acaguacuau    60
cagucgguuu ucgucgaggg ccccaaccga gcuc                               94

<210> SEQ ID NO 15
<211> LENGTH: 210
<212> TYPE: DNA
<213> ORGANISM: Artificial
<220> FEATURE:
<223> OTHER INFORMATION: Reporter Insert GAPDH Walk

<400> SEQUENCE: 15
ttcgtcatgg gtgtgaacca tgagaagtat gacaacagcc tcaagatcat cagcaatgcc    60
tcctgcacca ccaactgctt agcacccctg gccaaggtca tccatgacaa ctttggtatc   120
gtggaaggac tcatgaccac agtccatgcc atcactgcca cccagaagac tgtggatggc   180
ccctccggga aactgtggcg tgatggccgc                                    210

<210> SEQ ID NO 16
<211> LENGTH: 563
<212> TYPE: DNA
<213> ORGANISM: Homo sapiens

<400> SEQUENCE: 16
atggaagatt ataccaaaat agagaaaatt ggagaaggta cctatggagt tgtgtataag    60
ggtagacaca aaactacagg tcaagtggta gccatgaaaa aaatcagact agaaagtgaa   120
gaggaagggg ttcctagtac tgcaattcgg gaaatggaag attataccaa aatagagaaa   180
attggagaag gtacctatgg agttgtgtat aagggtagac acaaaactac aggtcaagtg   240
gtagccatga aaaaaatcag actagaaagt gaagaggaag gggttcggat tcagaaattg   300
atcaactctt caactcttca gaggatttgg gcactcccaa taatgaagtg tggccagaag   360
tggaatcttt acaggactat aagaatacat ttcccaaatg gaaaccagga agcctagcat   420
cccatgtcaa aaacttggat gaaaatggct tggatttgct ctcgaaaatg ttaatctatg   480
atccagccaa acgaatttct ggcaaaatgg cactgaatca tccatatttt aatgatttgg   540
acaatcagat taagaagatg tag                                           563

<210> SEQ ID NO 17
<211> LENGTH: 916
<212> TYPE: DNA
<213> ORGANISM: Homo sapiens

<400> SEQUENCE: 17
ctacaccaac ctctcgtaca tcggcgaggg cgcctacggc atggtgtgtc tgcttatgat    60
aatgtcmcaa agttcgagta gctatcaaga aaatcagccc ctttgagcac cagacctact   120
gccagagaac cctgagggag ataaaaatct tactgcgctt cagacatgag aacatcattg   180
gaatcaatga cattattcga gcaccmccat cgagcaaatg aaagatgtat atatagtaca   240
ggacctcatg gaaacagatc tttacaagct cttgaagaca caacacctca gcaatgacca   300
```

```
tatctgctat tttctctacc agatcctcag agggttaaaa tatatccatt cagctaacgt      360
tctgcaccgt gacctcaagc cttccaacct gctgctcmca ccacctgtga tctcaagatc      420
tgtgactttg gcctggcccg tgttgcagat ccagaccatg atcacacagg ttcctgaca       480 gaatatgtgg ccacacgttg gtacagggct ccagaaatta tgttgaattc caagtccatt     540
gatatttggt ctgtaggctg cattctggca gaaatgcttt ctaacaggcc catctttcca      600
gggaagcatt atcttgacca gctgaaccac attttgggta ttcttggatc cccatcacaa     660
gaagacctga attgtataat aaatttattg ctttctcttc cacacaaaaa taaggtgcca     720
tggaacaggc tgttcccaaa tgctgactcc aaagctctgg acttattgga caaaatgttg    780
acattcaacc cacacaagag gattgaagta gaacaggctc tggcccaccc atatctggag    840
cagtattacg acccgagtga cgagcccatc gccgmgcacc attcaagttc gacatggmtt   900
ggatgacttg cctaag                                                    916

<210> SEQ ID NO 18
<211> LENGTH: 1265
<212> TYPE: DNA
<213> ORGANISM: Homo sapiens

<400> SEQUENCE: 18
aatgggtaag tacatcaaga gcttcgtgga gcgcgtgctg aagaacgagc agtaattcta     60
ggcgatcgct cgagagcagc gatgcgaccc tccgggacgg ccggggcagc gctcctggcg   120
ctgctggctg cgctctgccc ggcgagtcgg gctctggagg aaaagaaagt ttgccaaggc    180
acgagtaaca agctcacgca gttgggcact tttgaaggat cattctcagc ctccagagga   240
tgttcaataa ctgtgaggtg gtccttggga atttggaaat tacctatgtg cagaggaatt    300
atgatctttc cttcttaaag accatccagg aggtggctgg ttatgtcctc attgccctca    360
acacagtgga gcgaattcct ttggaaaacc tgcagatcat cagaggaaat atgtactacg    420
aaaattccta tgccttagca gtcttatctm ctatgatgca aataaaaccg gactgaagga  480
gctgcccatg agaaatttac aggmtcctgc atggcgccgt gcggrrcagc aacaaccctg   540
ccctgtgcaa tgtggagagc atccagtggc gggacatagt cagcagtgac rrrctcagca    600
agcatgtcga tggacrrcca gaaccacctg gcagctgcc aaaagtgtga tccaagctgt   660
cccaatggga gctgctgggg tgcaggagag gagaactgcc agaaactgac caaaatcatc    720
tgtgcccagc agtgctccgg gcgctgccgt ggcaagtccc ccagtgactg ctgccacaac   780
cagtgtgctg caggctgcac aggccccggg agagcgact gcctggtctg ccgcaaattc    840
cgagacgmgc cacgtgcaag gacacctgcc ccccactcat gctctacaac cccaccacgt   900
accagatgga tgtgaacccc gagggcaaat acagctggtg ccaccctgcgt gaagaagtgc    960 ccccgtaatt atgtggtgac agatcacggc tcgtgcgtcc gagcctgtgg ggccgacagc   1020
tatgagatgg aggaagacgg cgtccgcaag tgtaagaagt gcgaagggc cttgccgcaa    1080 agtgtgtmcg gaataggtat tggtgaattt aaagactcac tctccataaa tgctacgaat   1140
attaaacact tcaaaaactg cacctccatc agtggcgatc tccacatcct gccggtggca   1200 tagggtggc tccttcacac atactcctcc tctggatcca caggaagcgt aaaggaaatc   1260
acagg                                                               1265

<210> SEQ ID NO 19
<211> LENGTH: 1845
<212> TYPE: DNA
<213> ORGANISM: Homo sapiens
```

<400> SEQUENCE: 19

```
atgccagacc ccgcggcgca cctgcccttc ttctacggca gcatctcgcg tgccgaggcc      60
gaggagcacc tgaagctggc gggcatggcg gacgggctct tcctgctgcg ccagtgcctg     120
cgctcgctgg gcggctatgt gctgtcgctc gtgcacgatg tgcgcttcca ccactttccc     180
atcgagcgcc agctcaacgg cacctacgcc atgccggcgg caaagcgcac tgtggaccgg     240
cagagctctg cgagttctac tcgcgcgacc ccgacgggct gccctgcaac ctgcgcaagc     300
cgtgcaaccg gccgtcgggc ctcgagccgc agccgggggt cttcgactgc tgcgagacg      360
ccatggtgcg tgactacgtg cgccagacgt ggaagctgga gggcgaggcc ctggagcagg     420
ccatcatcag ccaggccccg caggtggaga agctcattgc tacgacggcc acgagcgga     480
tgccctggta ccacagcagc ctgacgcgtg aggaggccga gcgcaaactt tactctgggg     540
cgcagaccga cggcaagtcc tgctgaggcc gcggaaggag cagggcacat acgccctgtc     600
cctcatctat gggaagacgg tgtaccacta cctcatcagc caagacaagg cgggcaagta     660
ctgcattccc gagggcacca gtttgacac gctctggcag ctggtggagt atctgaagct      720
gaaggcggac gggctcatct actgcctgaa ggaggcctgc cccmcagcag tgccagcaac     780
gcctcagggg ctgctgctcc cacactccca gcccacccat ccacgttgac tcatcctcag     840
agacgaatcg acaccctcaa ctcagatgga tacaccctg agccagcacg cataacgtcc      900
ccagacaaac cgcggccgat gcccatggac acgagcgtgt atgagagccc ctacagcgac     960
ccagaggagc tcaaggacaa gaagctcttc ctgmgcgcga taacctcctc atagctgaca    1020
ttgaacttgg ctgcggcaac tttggctcag tgcgccaggg cgtgtaccgc atgcgcaaga    1080
agcagatcga cgtggccatc aaggtgctga agcagggcac ggagaaggca gacacggaag    1140
agatgatgcg cgaggcgcag atcatgcacc agctggacaa ccctacatc gtgcggctca     1200
ttggcgtctg ccaggccgag gccctcatgc tggtcatgga gatggctggg gcgggccgc     1260
tgcacaagtt cctggtcggc aagagggagg agatccctgt gagcaatgtg gccgagctgc    1320
tgcaccaggt gtccatgggg atgaagtacc tggaggagmg mctttgtgca ccgtgacctg    1380
gcggcccgca acgtcctgct ggttaaccgg cactacgcca agatcagcga ctggcctctc    1440
cmgcactggg tgccgacgac agctactaca ctgcccgctc agcagggaag tggccgctca    1500
agtggtacgc acccgaatgc atcaacttcc gcaagttctc cagccgcagc gatgtctgga    1560
gctatggggt caccatgtgg gaggcctgtc ctacggccag mgcctacaa gaagatgaaa     1620
gggccggagg tcatggccrr catcgagcag ggcmgcggat ggagtgccca ccagagtgtc    1680
cacccgaact gtacgcactc atgagtgact gctggatcta cmgtgggagg atcgccccga    1740
cttcctgacc gtggagcagc gcatgcgagc ctgttactac agcctggcca gcaaggtggm    1800
gggcccccag gcagcacaca gaaggctgag gctgcctgtg cctga                    1845
```

<210> SEQ ID NO 20
<211> LENGTH: 90
<212> TYPE: DNA
<213> ORGANISM: Artificial
<220> FEATURE:
<223> OTHER INFORMATION: Zap70

<400> SEQUENCE: 20

```
tgatctgtgg cttggcgtag tgccggttaa cgggattgag ttttgaactc gttaacccgc      60
actatgccga gttacatcag tcggttttcg                                        90
```

<210> SEQ ID NO 21
<211> LENGTH: 90
<212> TYPE: DNA
<213> ORGANISM: Artificial
<220> FEATURE:
<223> OTHER INFORMATION: Zap70

<400> SEQUENCE: 21
tgatctgtgg cttgcgtacc acttgagcgg cgggattgag ttttgaactc gtcgctctag    60
tggtgcgcga gttacatcag tcggttttcg                                     90

<210> SEQ ID NO 22
<211> LENGTH: 91
<212> TYPE: DNA
<213> ORGANISM: Artificial
<220> FEATURE:
<223> OTHER INFORMATION: Zap70

<400> SEQUENCE: 22
tgatctgtgg cttgcggaag ttgatgcatt cgggattgag ttttgaactc ggatgcaaca    60
actttcgcga gttdacatca gtcggttttc g                                   91

<210> SEQ ID NO 23
<211> LENGTH: 90
<212> TYPE: DNA
<213> ORGANISM: Artificial
<220> FEATURE:
<223> OTHER INFORMATION: Zap70

<400> SEQUENCE: 23
tgatctgtgg cttgccgcag ccaagttcaa tgggattgag ttttgaactc gttgaacatg    60
gctgtggcga gttacatcag tcggttttcg                                     90

<210> SEQ ID NO 24
<211> LENGTH: 90
<212> TYPE: DNA
<213> ORGANISM: Artificial
<220> FEATURE:
<223> OTHER INFORMATION: Vector insert
<220> FEATURE:
<221> NAME/KEY: misc_feature
<222> LOCATION: (13)..(31)
<223> OTHER INFORMATION: where n is any combination of A, C, G or T
<220> FEATURE:
<221> NAME/KEY: misc_feature
<222> LOCATION: (51)..(69)
<223> OTHER INFORMATION: where n is any combination of A, C, G or T

<400> SEQUENCE: 24
tgatctgtgg ctnnnnnnnn nnnnnnnnnn ngggattgag ttttgaactc nnnnnnnnnn    60
nnnnnnnnna gttacatcag tcggttttcg                                     90

<210> SEQ ID NO 25

<400> SEQUENCE: 25

000

<210> SEQ ID NO 26
<211> LENGTH: 35
<212> TYPE: DNA
<213> ORGANISM: Artificial
<220> FEATURE:
<223> OTHER INFORMATION: Synthetic Primer SpeImiR338-For -continued

<400> SEQUENCE: 26
tcatactagt gagacagacc ctgcttcgaa ggacc                              35

<210> SEQ ID NO 27
<211> LENGTH: 35
<212> TYPE: DNA
<213> ORGANISM: Artificial
<220> FEATURE:
<223> OTHER INFORMATION: Synthetic Primer BglIImiR338-Rev

<400> SEQUENCE: 27
tcatagatct tgtccctccc cacataaaac ccatg                              35

<210> SEQ ID NO 28
<211> LENGTH: 40
<212> TYPE: DNA
<213> ORGANISM: Artificial
<220> FEATURE:
<223> OTHER INFORMATION: Synthetic Primer SpeImiR30c-1-For

<400> SEQUENCE: 28
tcatactagt ttttactcag ccagcccaag tggttctgtg                         40

<210> SEQ ID NO 29
<211> LENGTH: 38
<212> TYPE: DNA
<213> ORGANISM: Artificial
<220> FEATURE:
<223> OTHER INFORMATION: Synthetic Primer BglIImiR30c-1-Rev

<400> SEQUENCE: 29
tcatagatct acatctggtt ctggttgtac ttagccac                           38

<210> SEQ ID NO 30
<211> LENGTH: 35
<212> TYPE: DNA
<213> ORGANISM: Artificial
<220> FEATURE:
<223> OTHER INFORMATION: Synthetic Primer SpeImiR-26b-For

<400> SEQUENCE: 30
tcatactagt tggatacatg tggaatgtca gaggc                              35

<210> SEQ ID NO 31
<211> LENGTH: 35
<212> TYPE: DNA
<213> ORGANISM: Artificial
<220> FEATURE:
<223> OTHER INFORMATION: Synthetic Primer BglIImiR-26b-Rev

<400> SEQUENCE: 31
tcatagatct tgaccactgc tggggaaact gtacc                              35

<210> SEQ ID NO 32
<211> LENGTH: 36
<212> TYPE: DNA
<213> ORGANISM: Artificial
<220> FEATURE:
<223> OTHER INFORMATION: Synthetic Primer SpeImiR196a-2-For

<400> SEQUENCE: 32
tcatactagt tcagacccct tacccaccca gcaacc                             36

<210> SEQ ID NO 33
<211> LENGTH: 39

<212> TYPE: DNA
<213> ORGANISM: Artificial
<220> FEATURE:
<223> OTHER INFORMATION: Synthetic Primer BglIImiR196a-2-Rev

<400> SEQUENCE: 33
tcatagatct agaggacggc ataaagcagg gttctccag                               39

<210> SEQ ID NO 34
<211> LENGTH: 38
<212> TYPE: DNA
<213> ORGANISM: Artificial
<220> FEATURE:
<223> OTHER INFORMATION: Synthetic Primer SpeImiR196a-1-For

<400> SEQUENCE: 34
tcatactagt tccgatgtgt tgtttagtag caactggg                                38

<210> SEQ ID NO 35
<211> LENGTH: 35
<212> TYPE: DNA
<213> ORGANISM: Artificial
<220> FEATURE:
<223> OTHER INFORMATION: Synthetic Primer BglIImiR196a-1-Rev

<400> SEQUENCE: 35
tcatagatct gacacttccc agatctcttc tctgg                                   35

<210> SEQ ID NO 36
<211> LENGTH: 39
<212> TYPE: DNA
<213> ORGANISM: Artificial
<220> FEATURE:
<223> OTHER INFORMATION: Synthetic Primer SpeImiR30a-For

<400> SEQUENCE: 36
tcatactagt cggtgatgaa taatagacat ccatgagcc                               39

<210> SEQ ID NO 37
<211> LENGTH: 34
<212> TYPE: DNA
<213> ORGANISM: Artificial
<220> FEATURE:
<223> OTHER INFORMATION: Synthetic Primer BglIImiR30a-Rev

<400> SEQUENCE: 37
tcatagatct acctcctcaa tgccctgctg aagc                                    34

<210> SEQ ID NO 38
<211> LENGTH: 32
<212> TYPE: DNA
<213> ORGANISM: Artificial
<220> FEATURE:
<223> OTHER INFORMATION: Synthetic Primer SpeImiR126-For

<400> SEQUENCE: 38
tcatactagt ggcactggaa tctgggcgga ag                                      32

<210> SEQ ID NO 39
<211> LENGTH: 34
<212> TYPE: DNA
<213> ORGANISM: Artificial
<220> FEATURE:
<223> OTHER INFORMATION: Synthetic Primer BglIImiR126-Rev

<400> SEQUENCE: 39
tcatagatct agaagactca ggcccaggcc tctg                               34

<210> SEQ ID NO 40
<211> LENGTH: 35
<212> TYPE: DNA
<213> ORGANISM: Artificial
<220> FEATURE:
<223> OTHER INFORMATION: Synthetic Primer SpeImiR-204-For

<400> SEQUENCE: 40
tcatactagt tgagggtgga ggcaagcaga ggacc                              35

<210> SEQ ID NO 41
<211> LENGTH: 37
<212> TYPE: DNA
<213> ORGANISM: Artificial
<220> FEATURE:
<223> OTHER INFORMATION: Synthetic Primer BglIImiR-204-Rev

<400> SEQUENCE: 41
tcatagatct ttggacccag aactattagt ctttgag                            37

<210> SEQ ID NO 42
<211> LENGTH: 35
<212> TYPE: DNA
<213> ORGANISM: Artificial
<220> FEATURE:
<223> OTHER INFORMATION: Synthetic Primer SpeImiR486-For

<400> SEQUENCE: 42
tcatactagt gcgggccctg attttttgccg aatgc                             35

<210> SEQ ID NO 43
<211> LENGTH: 33
<212> TYPE: DNA
<213> ORGANISM: Artificial
<220> FEATURE:
<223> OTHER INFORMATION: Synthetic Primer BglIImiR486-Rev

<400> SEQUENCE: 43
tcatagatct agcatggggc agtgtggcca cag                                33

<210> SEQ ID NO 44
<211> LENGTH: 40
<212> TYPE: DNA
<213> ORGANISM: Artificial
<220> FEATURE:
<223> OTHER INFORMATION: Synthetic Primer SpeImiR135a-2-For

<400> SEQUENCE: 44
tcatactagt aaatcttgtt aattcgtgat gtcacaattc                         40

<210> SEQ ID NO 45
<211> LENGTH: 36
<212> TYPE: DNA
<213> ORGANISM: Artificial
<220> FEATURE:
<223> OTHER INFORMATION: Synthetic Primer BglIImiR135a-2-Rev

<400> SEQUENCE: 45
tcatagatct cacctagatt tctcagctgt caaatc                             36

<210> SEQ ID NO 46
<211> LENGTH: 37
<212> TYPE: DNA
<213> ORGANISM: Artificial

```
<220> FEATURE:
<223> OTHER INFORMATION: Synthetic Primer SpeImiR374-For

<400> SEQUENCE: 46
tcatactagt caattccgtc tatggccacg ggttagg                              37

<210> SEQ ID NO 47
<211> LENGTH: 36
<212> TYPE: DNA
<213> ORGANISM: Artificial
<220> FEATURE:
<223> OTHER INFORMATION: Synthetic Primer Bg1IImiR374-Rev

<400> SEQUENCE: 47
tcatagatct tgtggagctc actttagcag gcacac                               36

<210> SEQ ID NO 48
<211> LENGTH: 38
<212> TYPE: DNA
<213> ORGANISM: Artificial
<220> FEATURE:
<223> OTHER INFORMATION: Synthetic Primer SpeImiR526a-1-For

<400> SEQUENCE: 48
tcatactagt aatgtaaggt atgtgtagta ggcaatgc                             38

<210> SEQ ID NO 49
<211> LENGTH: 36
<212> TYPE: DNA
<213> ORGANISM: Artificial
<220> FEATURE:
<223> OTHER INFORMATION: Synthetic Primer Bg1IImiR526a-1-Rev

<400> SEQUENCE: 49
tcatagatct agttcctgat actgagctcc agccag                               36

<210> SEQ ID NO 50
<211> LENGTH: 47
<212> TYPE: DNA
<213> ORGANISM: Artificial
<220> FEATURE:
<223> OTHER INFORMATION: Reporter sequence for screening miR-338

<400> SEQUENCE: 50
tcgaatgacc cttcaacaaa atcactgatg ctggagtctc gagctgc                   47

<210> SEQ ID NO 51
<211> LENGTH: 47
<212> TYPE: DNA
<213> ORGANISM: Artificial
<220> FEATURE:
<223> OTHER INFORMATION: Reporter sequence for screening miR-30c-1

<400> SEQUENCE: 51
tcgaatgacc cagctgagag tgtaggatgt ttacacactc gagctgc                   47

<210> SEQ ID NO 52
<211> LENGTH: 46
<212> TYPE: DNA
<213> ORGANISM: Artificial
<220> FEATURE:
<223> OTHER INFORMATION: Reporter sequence for screening miR-26b

<400> SEQUENCE: 52
tcgaatgacc acaacctatc ctgaattact tgaactctcg agctgc                    46
```

<210> SEQ ID NO 53
<211> LENGTH: 45
<212> TYPE: DNA
<213> ORGANISM: Artificial
<220> FEATURE:
<223> OTHER INFORMATION: Reporter sequence for screening miR-196a-2

<400> SEQUENCE: 53
tcgaatgacc tcccaacaac atgaaactac ctaagctcga gctgc    45

<210> SEQ ID NO 54
<211> LENGTH: 45
<212> TYPE: DNA
<213> ORGANISM: Artificial
<220> FEATURE:
<223> OTHER INFORMATION: Reporter sequence for screening miR-196a-1

<400> SEQUENCE: 54
tcgaatgacc gcccaacaac atgaaactac ctaatctcga gctgc    45

<210> SEQ ID NO 55
<211> LENGTH: 46
<212> TYPE: DNA
<213> ORGANISM: Artificial
<220> FEATURE:
<223> OTHER INFORMATION: Reporter sequence for screening miR-30a-5p

<400> SEQUENCE: 55
tcgaatgacc agcttccagt cgaggatgtt tacagtctcg agctgc    46

<210> SEQ ID NO 56
<211> LENGTH: 45
<212> TYPE: DNA
<213> ORGANISM: Artificial
<220> FEATURE:
<223> OTHER INFORMATION: Reporter sequence for screening miR-126

<400> SEQUENCE: 56
tcgaatgacc agcgcgtacc aaaagtaata atgtcctcga gctgc    45

<210> SEQ ID NO 57
<211> LENGTH: 45
<212> TYPE: DNA
<213> ORGANISM: Artificial
<220> FEATURE:
<223> OTHER INFORMATION: Reporter sequence for screening miR-126

<400> SEQUENCE: 57
tcgaatgacc gcgcattatt actcacggta cgagtctcga gctgc    45

<210> SEQ ID NO 58
<211> LENGTH: 46
<212> TYPE: DNA
<213> ORGANISM: Artificial
<220> FEATURE:
<223> OTHER INFORMATION: Reporter sequence for screening miR-204

<400> SEQUENCE: 58
tcgaatgacc tcaggcatag gatgacaaag ggaagtctcg agctgc    46

<210> SEQ ID NO 59
<211> LENGTH: 47
<212> TYPE: DNA
<213> ORGANISM: Artificial
<220> FEATURE:
<223> OTHER INFORMATION: Reporter sequence for screening miR-135a-2

-continued

<400> SEQUENCE: 59
tcgaatgacc tatcacatag gaataaaaag ccataaactc gagctgc        47

<210> SEQ ID NO 60
<211> LENGTH: 46
<212> TYPE: DNA
<213> ORGANISM: Artificial
<220> FEATURE:
<223> OTHER INFORMATION: Reporter sequence for screening miR-374

<400> SEQUENCE: 60
tcgaatgacc aacacttatc aggttgtatt ataatgctcg agctgc          46

<210> SEQ ID NO 61
<211> LENGTH: 45
<212> TYPE: DNA
<213> ORGANISM: Artificial
<220> FEATURE:
<223> OTHER INFORMATION: Reporter sequence for screening miR-526a-1

<400> SEQUENCE: 61
tcgaatgacc acagaaagtg cttccctcta gagggctcga gctgc            45

<210> SEQ ID NO 62
<211> LENGTH: 46
<212> TYPE: DNA
<213> ORGANISM: Artificial
<220> FEATURE:
<223> OTHER INFORMATION: Reporter sequence for screening miR-486

<400> SEQUENCE: 62
tcgaatgacc agctcggggc agctcagtac aggatactcg agctgc          46

<210> SEQ ID NO 63
<211> LENGTH: 25
<212> TYPE: DNA
<213> ORGANISM: Artificial
<220> FEATURE:
<223> OTHER INFORMATION: Reporter sequence for detecting miR-204

<400> SEQUENCE: 63
ggaggctggg aaggcaaagg gacgt                                 25

<210> SEQ ID NO 64
<211> LENGTH: 25
<212> TYPE: DNA
<213> ORGANISM: Artificial
<220> FEATURE:
<223> OTHER INFORMATION: Reporter sequence for detecting miR-26b

<400> SEQUENCE: 64
ccagcctgtt ctccattact tggct                                 25

<210> SEQ ID NO 65
<211> LENGTH: 25
<212> TYPE: DNA
<213> ORGANISM: Artificial
<220> FEATURE:
<223> OTHER INFORMATION: Reporter sequence for detecting miR-196a-2

<400> SEQUENCE: 65
actcggcaac aagaaactgc ctgag                                 25

<210> SEQ ID NO 66

```
<211> LENGTH: 46
<212> TYPE: DNA
<213> ORGANISM: Artificial
<220> FEATURE:
<223> OTHER INFORMATION: Reporter sequence for detecting miR-30a-3p

<400> SEQUENCE: 66
tcgaatgacc cagctgcaaa catccgactg aaagccctcg agctgc                        46

<210> SEQ ID NO 67
<211> LENGTH: 119
<212> TYPE: DNA
<213> ORGANISM: Artificial
<220> FEATURE:
<223> OTHER INFORMATION: Intron

<400> SEQUENCE: 67
caggtaagtt agtagataga tagcgtgcta tttactagtc gtagatctac aatgttgaat         60
tctcacgcgg ccgctctact aaccctctt ttctttctct tcctttcatc tttcaggcg          119

<210> SEQ ID NO 68
<211> LENGTH: 21
<212> TYPE: DNA
<213> ORGANISM: Artificial
<220> FEATURE:
<223> OTHER INFORMATION: Probe sequence for miR-196a-2as

<400> SEQUENCE: 68
ccaacaacat gaaactacct a                                                   21

<210> SEQ ID NO 69
<211> LENGTH: 115
<212> TYPE: DNA
<213> ORGANISM: Homo sapiens

<400> SEQUENCE: 69
tcagctgatc tgtggctttt cgtagtacat atttcctcga ttgagttttg aacgaggaaa         60
taagtactat gaagagttac atcagtcggt tttcgtcgag ggccccaacc gagct             115

<210> SEQ ID NO 70
<211> LENGTH: 115
<212> TYPE: DNA
<213> ORGANISM: Homo sapiens

<400> SEQUENCE: 70
tcagctgatc tgtggctaac tgcgtgagct tgttactcga ttgagttttg aacgagtaac         60
aacctcacgt agttagttac atcagtcggt tttcgtcgag ggccccaacc gagct             115

<210> SEQ ID NO 71
<211> LENGTH: 115
<212> TYPE: DNA
<213> ORGANISM: Homo sapiens

<400> SEQUENCE: 71
tcagctgatc tgtggctcat tgggacagct tggatcacga ttgagttttg aacgtggtcc         60
aacctgtcct aatgagttac atcagtcggt tttcgtcgag ggccccaacc gagct             115

<210> SEQ ID NO 72
<211> LENGTH: 115
<212> TYPE: DNA
<213> ORGANISM: Homo sapiens

<400> SEQUENCE: 72
```

```
tcagctgatc tgtggcttct gtcaccacat aattacggga ttgagttttg aactcgtaat    60
taagtggtgg caggagttac atcagtcggt tttcgtcgag ggccccaacc gagct        115

<210> SEQ ID NO 73
<211> LENGTH: 115
<212> TYPE: DNA
<213> ORGANISM: Homo sapiens

<400> SEQUENCE: 73
tcagctgatc tgtggcttat tccgttacac actttgcgga ttgagttttg aactgtgaag    60
tgagtaacgg aatgagttac atcagtcggt tttcgtcgag ggccccaacc gagct        115

<210> SEQ ID NO 74
<211> LENGTH: 115
<212> TYPE: DNA
<213> ORGANISM: Homo sapiens

<400> SEQUENCE: 74
tcagctgatc tgtggctaat ttctggagcc ctgtaccaga ttgagttttg aactggtaca    60
ggcgtccagg aattagttac atcagtcggt tttcgtcgag ggccccaacc gagct        115

<210> SEQ ID NO 75
<211> LENGTH: 115
<212> TYPE: DNA
<213> ORGANISM: Homo sapiens

<400> SEQUENCE: 75
tcagctgatc tgtggctctt gtaaagatct gtttccatga ttgagttttg aacgtggaaa    60
cacatctttg caagagttac atcagtcggt tttcgtcgag ggccccaacc gagct        115

<210> SEQ ID NO 76
<211> LENGTH: 115
<212> TYPE: DNA
<213> ORGANISM: Homo sapiens

<400> SEQUENCE: 76
tcagctgatc tgtggctaat aagtccagag ctttggagga ttgagttttg aacttttaaa    60
gcactggact tattagttac atcagtcggt tttcgtcgag ggccccaacc gagct        115

<210> SEQ ID NO 77
<211> LENGTH: 115
<212> TYPE: DNA
<213> ORGANISM: Homo sapiens

<400> SEQUENCE: 77
tcagctgatc tgtggctaaa gcaaatagtt cctagcttga ttgagttttg aacgagttag    60
gatctatttg ctttagttac atcagtcggt tttcgtcgag ggccccaacc gagct        115

<210> SEQ ID NO 78
<211> LENGTH: 115
<212> TYPE: DNA
<213> ORGANISM: Homo sapiens

<400> SEQUENCE: 78
tcagctgatc tgtggcttac aattcaggtc ttcttgtgga ttgagttttg aactatgaga    60
agtcctgaat tgtgagttac atcagtcggt tttcgtcgag ggccccaacc gagct        115

<210> SEQ ID NO 79
```

-continued

```
<211> LENGTH: 90
<212> TYPE: DNA
<213> ORGANISM: Homo sapiens

<400> SEQUENCE: 79
tgatctgtgg cttattcgta gcatttatgg agggattgag ttttgaactc ttcataattg    60
ctacgaatga gttacatcag tcggttttcg                                    90

<210> SEQ ID NO 80
<211> LENGTH: 90
<212> TYPE: DNA
<213> ORGANISM: Homo sapiens

<400> SEQUENCE: 80
tgatctgtgg cttcgtagta catatttcct cgggattgag ttttgaactc ggggaaaaat    60
gtactacgga gttacatcag tcggttttcg                                    90

<210> SEQ ID NO 81
<211> LENGTH: 90
<212> TYPE: DNA
<213> ORGANISM: Homo sapiens

<400> SEQUENCE: 81
tgatctgtgg cttcgtctcg gaatttgcgg cgggattgag ttttgaactc gtcgcaattt    60
ccgagacgga gttacatcag tcggttttcg                                    90

<210> SEQ ID NO 82
<211> LENGTH: 90
<212> TYPE: DNA
<213> ORGANISM: Homo sapiens

<400> SEQUENCE: 82
tgatctgtgg cttacggttt tcagaatatc cgggattgag ttttgaactc ggatattgtg    60
aaaatcgtga gttacatcag tcggttttcg                                    90

<210> SEQ ID NO 83
<211> LENGTH: 90
<212> TYPE: DNA
<213> ORGANISM: Homo sapiens

<400> SEQUENCE: 83
tgatctgtgg cttccggttt tatttgcatc agggattgag ttttgaactc tgatgcatat    60
aaaatcggga gttacatcag tcggttttcg                                    90

<210> SEQ ID NO 84
<211> LENGTH: 90
<212> TYPE: DNA
<213> ORGANISM: Homo sapiens

<400> SEQUENCE: 84
tgatctgtgg ctttgctcga tggttggtgc tgggattgag ttttgaactc ggcaccatcc    60
atcgggcaga gttacatcag tcggttttcg                                    90

<210> SEQ ID NO 85
<211> LENGTH: 90
<212> TYPE: DNA
<213> ORGANISM: Homo sapiens

<400> SEQUENCE: 85
tgatctgtgg cttcgaactt gaatggtgct tgggattgag ttttgaactc gggcaccttt    60
```
caagttcgga gttacatcag tcggttttcg                                              90

<210> SEQ ID NO 86
<211> LENGTH: 90
<212> TYPE: DNA
<213> ORGANISM: Homo sapiens

<400> SEQUENCE: 86
tgatctgtgg cttactcgaa ctttgttgac agggattgag ttttgaactc tgtcaactaa             60
gttcgagtga gttacatcag tcggttttcg                                              90

<210> SEQ ID NO 87
<211> LENGTH: 90
<212> TYPE: DNA
<213> ORGANISM: Homo sapiens

<400> SEQUENCE: 87
tgatctgtgg cttcgtaata ctgctccaga tgggattgag ttttgaactc gtctggacca             60
gtattacgga gttacatcag tcggttttcg                                              90

<210> SEQ ID NO 88
<211> LENGTH: 90
<212> TYPE: DNA
<213> ORGANISM: Homo sapiens

<400> SEQUENCE: 88
tgatctgtgg cttccatgag gtcctgtact agggattgag ttttgaactc tggtacacga             60
cctcgtggga gttacatcag tcggttttcg                                              90

<210> SEQ ID NO 89
<211> LENGTH: 22
<212> TYPE: RNA
<213> ORGANISM: Homo sapiens

<400> SEQUENCE: 89
uggaauguaa agaaguaugu au                                                      22

<210> SEQ ID NO 90
<211> LENGTH: 19
<212> TYPE: DNA
<213> ORGANISM: Artificial
<220> FEATURE:
<223> OTHER INFORMATION: Oligo

<400> SEQUENCE: 90
tggaatgtaa agaagtatg                                                          19

<210> SEQ ID NO 91
<211> LENGTH: 21
<212> TYPE: RNA
<213> ORGANISM: Homo sapiens

<400> SEQUENCE: 91
uaaagugcug acagugcaga u                                                       21

<210> SEQ ID NO 92
<211> LENGTH: 19
<212> TYPE: DNA
<213> ORGANISM: Artificial
<220> FEATURE:
<223> OTHER INFORMATION: Oligo -continued

```
<400> SEQUENCE: 92
taaagtgctg acagtgcag                                              19

<210> SEQ ID NO 93
<211> LENGTH: 22
<212> TYPE: RNA
<213> ORGANISM: Homo sapiens

<400> SEQUENCE: 93
uggaguguga cauggguguu ug                                          22

<210> SEQ ID NO 94
<211> LENGTH: 22
<212> TYPE: DNA
<213> ORGANISM: Artificial
<220> FEATURE:
<223> OTHER INFORMATION: Oligo

<400> SEQUENCE: 94
tggagtgtga caatggtgtt tg                                          22

<210> SEQ ID NO 95
<211> LENGTH: 20
<212> TYPE: RNA
<213> ORGANISM: Homo sapiens

<400> SEQUENCE: 95
uaaggcacgc ggugaaugcc                                             20

<210> SEQ ID NO 96
<211> LENGTH: 20
<212> TYPE: DNA
<213> ORGANISM: Artificial
<220> FEATURE:
<223> OTHER INFORMATION: Oligo

<400> SEQUENCE: 96
taaggcacgc ggtgaatgcc                                             20

<210> SEQ ID NO 97
<211> LENGTH: 22
<212> TYPE: RNA
<213> ORGANISM: Homo sapiens

<400> SEQUENCE: 97
uaacagucua cagccauggu cg                                          22

<210> SEQ ID NO 98
<211> LENGTH: 22
<212> TYPE: DNA
<213> ORGANISM: Artificial
<220> FEATURE:
<223> OTHER INFORMATION: Oligo

<400> SEQUENCE: 98
taacagtcta cagccatggt cg                                          22

<210> SEQ ID NO 99
<211> LENGTH: 21
<212> TYPE: RNA
<213> ORGANISM: Homo sapiens

<400> SEQUENCE: 99
uucaaguaau ucaggauagg u                                           21
```

```
<210> SEQ ID NO 100
<211> LENGTH: 21
<212> TYPE: DNA
<213> ORGANISM: Artificial
<220> FEATURE:
<223> OTHER INFORMATION: oligo

<400> SEQUENCE: 100
ttcaagtaat tcaggatagg t                                              21

<210> SEQ ID NO 101
<211> LENGTH: 22
<212> TYPE: RNA
<213> ORGANISM: Homo sapiens

<400> SEQUENCE: 101
cuuucagucg gauguuugca gc                                             22

<210> SEQ ID NO 102
<211> LENGTH: 22
<212> TYPE: DNA
<213> ORGANISM: Artificial
<220> FEATURE:
<223> OTHER INFORMATION: Oligo

<400> SEQUENCE: 102
ttttcagtcg gatgtttgca gc                                             22

<210> SEQ ID NO 103
<211> LENGTH: 22
<212> TYPE: RNA
<213> ORGANISM: Homo sapiens

<400> SEQUENCE: 103
uggcagaguc uuagcugguu gu                                             22

<210> SEQ ID NO 104
<211> LENGTH: 22
<212> TYPE: DNA
<213> ORGANISM: Artificial
<220> FEATURE:
<223> OTHER INFORMATION: Oligo

<400> SEQUENCE: 104
tggcagtgtc ttagctggtt gt                                             22

<210> SEQ ID NO 105
<211> LENGTH: 23
<212> TYPE: RNA
<213> ORGANISM: Homo sapiens

<400> SEQUENCE: 105
ucuuugguua ucuagcugua uga                                            23

<210> SEQ ID NO 106
<211> LENGTH: 23
<212> TYPE: DNA
<213> ORGANISM: Artificial
<220> FEATURE:
<223> OTHER INFORMATION: Oligo

<400> SEQUENCE: 106
tctttggtta tctagctgta tga                                            23
```

```
<210> SEQ ID NO 107
<211> LENGTH: 22
<212> TYPE: RNA
<213> ORGANISM: Homo sapiens

<400> SEQUENCE: 107
auaagacgag caaaaagcuu gu                                              22

<210> SEQ ID NO 108
<211> LENGTH: 22
<212> TYPE: DNA
<213> ORGANISM: Artificial
<220> FEATURE:
<223> OTHER INFORMATION: Oligo

<400> SEQUENCE: 108
ttaagacgag caaaaagctt gt                                              22

<210> SEQ ID NO 109
<211> LENGTH: 22
<212> TYPE: RNA
<213> ORGANISM: Homo sapiens

<400> SEQUENCE: 109
auaagacgaa caaaagguuu gu                                              22

<210> SEQ ID NO 110
<211> LENGTH: 22
<212> TYPE: DNA
<213> ORGANISM: Artificial
<220> FEATURE:
<223> OTHER INFORMATION: Oligo

<400> SEQUENCE: 110
ttaagacgaa caaaaggttt gt                                              22

<210> SEQ ID NO 111
<211> LENGTH: 22
<212> TYPE: RNA
<213> ORGANISM: Homo sapiens

<400> SEQUENCE: 111
aacaucacag caagucugug cu                                              22

<210> SEQ ID NO 112
<211> LENGTH: 22
<212> TYPE: DNA
<213> ORGANISM: Artificial
<220> FEATURE:
<223> OTHER INFORMATION: Oligo

<400> SEQUENCE: 112
tacatcacag caagtctgtg ct                                              22

<210> SEQ ID NO 113
<211> LENGTH: 21
<212> TYPE: RNA
<213> ORGANISM: Homo sapiens

<400> SEQUENCE: 113
uuaagacuug cagugauguu u                                               21

<210> SEQ ID NO 114
<211> LENGTH: 21
```

```
<212> TYPE: DNA
<213> ORGANISM: Artificial
<220> FEATURE:
<223> OTHER INFORMATION: Oligo

<400> SEQUENCE: 114
ttaagacttg cagtgatgtt t                                              21

<210> SEQ ID NO 115
<211> LENGTH: 110
<212> TYPE: RNA
<213> ORGANISM: Homo sapiens

<400> SEQUENCE: 115
ugcucgcuca gcugaucugu ggcuuaggua guuucauguu guugggauug aguuuugaac    60
ucggcaacaa gaaacugccu gaguuacauc agucgguuuu cgucgagggc              110
```

MICRO-RNA SCAFFOLDS AND NON-NATURALLY OCCURRING MICRO-RNAS

RELATED APPLICATION INFORMATION

This application is being filed on 22 May 2008, as a PCT International Patent application in the name of Dharmacon, Inc., a U.S. national corporation, applicant for the designation of all countries except the U.S., and Melissa KELLEY, a citizen of the U.S., Amanda BIRMINGHAM, a citizen of the U.S., Jon KARPILOW, a citizen of the U.S., Anastasia KHVOROVA, a citizen of Russia, Kevin SULLIVAN, a citizen of the U.S., applicants for the designation of the U.S. only, and claims priority to U.S. Provisional Patent Application Ser. No. 60/939,785 filed on 23 May 2007.

FIELD OF THE INVENTION

The present invention relates to the field of RNAi. In particular, the invention describes miRNA-based scaffolds into which targeting sequences can be integrated to form non-naturally occurring miRNAs that effectively mediate gene knockdown.

BACKGROUND

RNA interference (RNAi) is a near-ubiquitous pathway involved in post-transcriptional gene modulation. A key effector molecule of RNAi is the microRNA (miRNA or miR). These small, non-coding RNAs are transcribed as primary miRNAs (pri-miRNA) and processed in the nucleus by Drosha (a Type III ribonuclease) to generate short hairpin structures referred to as pre-miRNAs (FIG. 1). The resulting molecules are transported to the cytoplasm and processed by a second nuclease (Dicer) before being incorporated into the RNA Induced Silencing Complex (RISC). Interactions between the mature miRNA-RISC complex and messenger RNA (mRNA), particularly between the seed region of the miRNA guide strand (nucleotides 2-7) and regions of the 3' UTR of the mRNA, leads to gene knockdown by transcript cleavage and/or translation attenuation.

While study of native substrates (miRNA) has garnered considerable interest in recent years, the RNAi pathway has also been recognized as a powerful research tool. Small double stranded RNAs (referred to as small interfering RNAs or siRNA) generated by synthetic chemistries or enzymatic methods can be introduced into cells by a variety of means (e.g. lipid mediated transfection, electroporation) and enter the pathway to target specific gene transcripts for degradation. As such, the RNAi pathway serves as a potent tool in the investigation of gene function, pathway analysis, and drug discovery, and is envisioned to have future applications as a therapeutic agent.

Though the use of synthetic siRNA serves the needs of most gene knockdown experiments, there are some instances where synthetic molecules are unsuitable. A fraction of the cell types are resilient or highly sensitive to commonly used transfection methods and/or reagents. In still other instances, the needs of the experimental system require that gene knockdown be achieved for periods longer than those provided by synthetic molecules (typically 4-10 days).

Vector-based delivery of silencing reagents has previously been achieved using a range of delivery (e.g., lentiviral) and scaffold (simple hairpins, miRNA-based) configurations (Samakoglu et al., Nature Biotech.; Lei Y. S. et al., 2005; Leirdal and Sioud, 2002; Anderson et al., 2003; Grimm, D. et al., (2006) Nature Letters 441:537-541).

SUMMARY

In one aspect, the present disclosure provides a non-naturally occurring miRNA having a stem-loop structure comprising a scaffold derived from a first endogenous miRNA, a mature strand derived from a second endogenous miRNA, and a star strand sequence that is at least partially complementary to the mature strand sequence.

In another aspect, the present disclosure provides a non-naturally occurring miR-196a-2 miRNA comprising a nucleic acid having a stem-loop structure in which the stem of the stem-loop structure incorporates a mature strand-star strand duplex. The sequence of the mature strand is derived from a mature endogenous miRNA but is distinct from the sequence of the endogenous mature strand of miR-196a-2. The star strand is at least partially complementary to the mature strand. In some embodiments, the mature strand is between about 19 nucleotides and about 25 nucleotides in length. In some embodiments, the nucleotide at position 1 of the mature strand is U. In some embodiments, the nucleotide at position 12 of said mature strand does not form a base pair with the opposite nucleotide position on the star strand.

In another aspect, the present disclosure provides a non-naturally occurring miR-204 miRNA comprising a nucleic acid having a stem-loop structure in which the stem of the stem-loop structure incorporates a mature strand-star strand duplex. The sequence of the mature strand is derived from a mature endogenous miRNA but is distinct from the sequence of the endogenous mature strand of miR-204. The star strand is at least partially complementary to the mature strand.

In another aspect, the present disclosure provides a non-naturally occurring miR-196a-2 miRNA capable of being processed in a cell to yield a mature miRNA that is substantially similar to a mature endogenous miRNA wherein the sequence of the mature endogenous miRNA is different from the sequence of endogenous miR-196a-2 mature miRNA.

In another aspect, the present disclosure provides a non-naturally occurring miR-204 miRNA capable of being processed in a cell to yield a mature miRNA that is substantially similar to a mature endogenous miRNA wherein the sequence of the mature endogenous miRNA is different from the sequence of endogenous miR-204 mature miRNA.

In one aspect, the present disclosure provides a non-naturally occurring miRNA having a stem-loop structure comprising a scaffold derived from an endogenous miRNA (e.g. miR-196a-2 or miR-204), a mature strand that is at least partially complementary to a target RNA (e.g., positions 2-7 of the mature strand are complementary to a target RNA) but is distinct from any endogenous miRNA mature stand, and a star strand sequence that is at least partially complementary to the mature strand sequence.

In another aspect, the disclosure provides cells comprising non-naturally occurring miRNAs, for example non-naturally occurring miR-196a-2 miRNA or non-naturally occurring miR-204 miRNA.

In another aspect, the present disclosure provides a method of lowering the functional capacity of a target RNA in a cell. The method comprises contacting the cell with a vector capable of expressing a non-naturally occurring miRNA (e.g., a non-naturally occurring miR-196a-2 miRNA or non-naturally occurring miR-204 miRNA). The non-naturally occurring miRNA is processed in the cell to yield a miRNA that is substantially similar to an endogenous miRNA.

In another aspect, the present disclosure provides recombinant expression vectors comprising nucleotides sequence that encodes a non-naturally occurring miRNA (e.g., a non-naturally occurring miR-196a-2 miRNA or non-naturally occurring miR-204 miRNA).

In another aspect, the present disclosure provides a pharmaceutical composition comprising a non-naturally occurring miRNA (e.g., a non-naturally occurring miR-196a-2 miRNA or non-naturally occurring miR-204 miRNA) and further comprising at least one pharmaceutically acceptable carrier.

In another aspect, the present disclosure describes the use of a non-naturally miRNA (e.g., a non-naturally occurring miR-196a-2 miRNA or non-naturally occurring miR-204 miRNA) in the manufacture of a medicament for the treatment of a disease characterized by the inappropriate expression of a gene wherein the gene is targeted by the non-naturally occurring miRNA.

Other aspects of the invention are disclosed herein.

DETAILED DESCRIPTION

Figure 1:
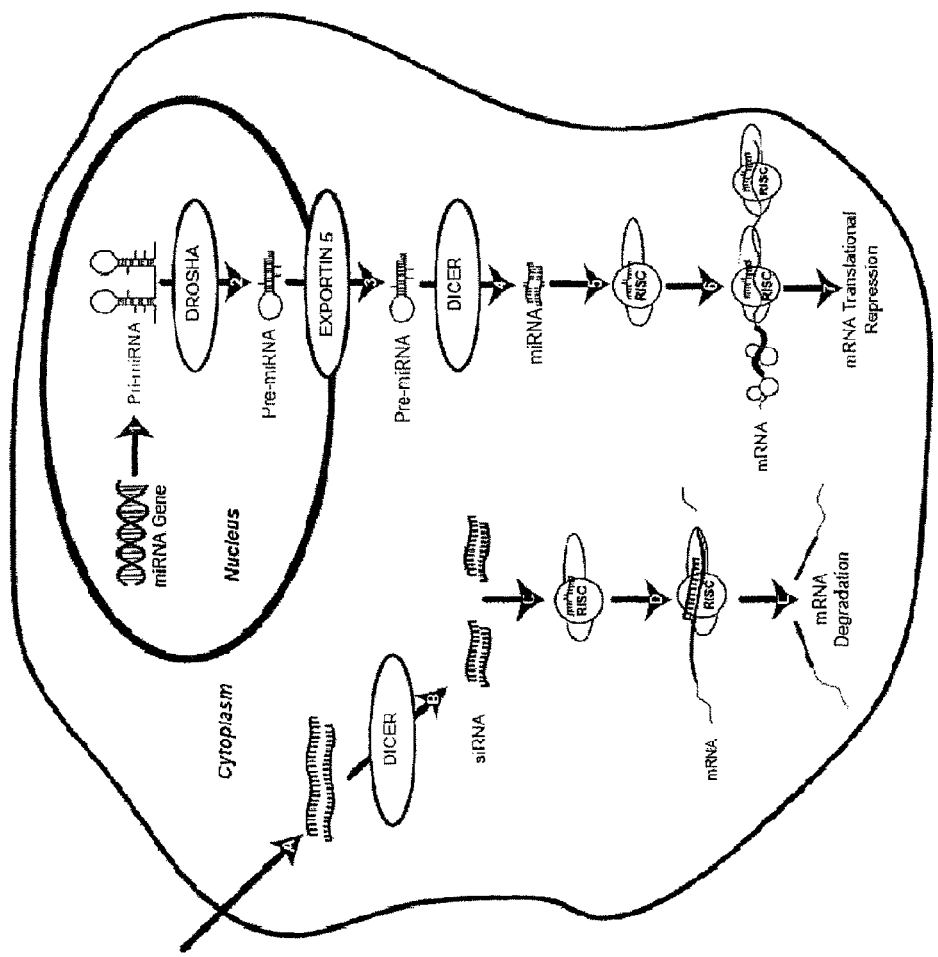
FIG. 1: Schematic drawing of the RNAi pathway. Drawing provides 1) a depiction of the processing of pri-miRNA→pre-miRNA→mature miRNA, and 2) the position where siRNA enter the pathway.

The term "artificial intron" refers to a specific sequence that has been designed to act as an intron (i.e., it has essential splice donor and acceptor sequences and other relevant properties) and has minimal secondary structure.

The term "rational design" refers to the application of a proven set of criteria that enhance the probability of identifying a sequence that will provide highly functional levels of gene silencing.

The term "reporter" or "reporter gene" refers to a gene whose expression can be monitored. For example, expression levels of a reporter can be assessed to evaluate the success of gene silencing by substrates of the RNAi pathway.

The term "RNA Induced Silencing Complex," and its acronym "RISC," refers to the set of proteins that complex with single-stranded polynucleotides such as mature miRNA or siRNA, to target nucleic acid molecules (e.g., mRNA) for cleavage, translation attenuation, methylation, and/or other alterations. Known, non-limiting components of RISC include Dicer, R2D2 and the Argonaute family of proteins, as well as strands of siRNAs and miRNAs.

The term "RNA interference" and the term "RNAi" are synonymous and refer to the process by which a polynucleotide (a miRNA or siRNA) comprising at least one polyribonucleotide unit exerts an effect on a biological process. The process includes, but is not limited to, gene silencing by degrading mRNA, attenuating translation, interactions with tRNA, rRNA, hnRNA, cDNA and genomic DNA, as well as methylation of DNA with ancillary proteins.

The term "gene silencing" refers to a process by which the expression of a specific gene product is lessened or attenuated by RNA interference. The level of gene silencing (also sometimes referred to as the degree of "knockdown") can be measured by a variety of means, including, but not limited to, measurement of transcript levels by Northern Blot Analysis, B-DNA techniques, transcription-sensitive reporter constructs, expression profiling (e.g. DNA chips), qRT-PCR and related technologies. Alternatively, the level of silencing can be measured by assessing the level of the protein encoded by a specific gene. This can be accomplished by performing a number of studies including Western Analysis, measuring the levels of expression of a reporter protein that has e.g. fluorescent properties (e.g., GFP) or enzymatic activity (e.g. alkaline phosphatases), or several other procedures.

The terms "microRNA", "miRNA", or "miR" all refer to non-coding RNAs (and also, as the context will indicate, to DNA sequences that encode such RNAs) that are capable of entering the RNAi pathway and regulating gene expression. "Primary miRNA" or "pri-miRNA" represents the non-coding transcript prior to Drosha processing and includes the stem-loop structure(s) as well as flanking 5' and 3' sequences. "Precursor miRNAs" or "pre-miRNA" represents the non-coding transcript after Drosha processing of the pri-miRNA. The term "mature miRNA" can refer to the double stranded product resulting from Dicer processing of pre-miRNA or the single stranded product that is introduced into RISC following Dicer processing. In some cases, only a single strand of an miRNA enters the RNAi pathway. In other cases, two strands of a miRNA are capable of entering the RNAi pathway.

The term "mature strand" refers to the sequence in an endogenous miRNA or in a non-naturally occurring miRNA that is the full or partial reverse complement (RC) of (i.e., is fully or partially complementary to) a target RNA of interest. The terms "mature sequence," "targeting strand," "targeting sequence" and "guide strand" are synonymous with the term "mature strand" and are often used interchangeably herein.

The term "star strand" refers to the strand that is fully complementary or partially complementary to the mature strand in a miRNA. The terms "passenger strand" and "star strand" are interchangeable.

The term "target sequence" refers to a sequence in a target RNA, or DNA that is partially or fully complementary to the mature strand. The target sequence can be described using the four bases of DNA (A, T, G, and C), or the four bases of RNA (A, U, G, and C). In some cases, the target sequence is the sequence recognized by an endogenous miRNA mature strand. In other cases, target sequences are determined randomly. In some cases, target sequences can be identified using an algorithm that identifies preferred target sequences based on one or more desired traits.

The term "target RNA" refers to a specific RNA that is targeted by the RNAi pathway, resulting in a decrease in the functional activity of the RNA. In some cases, the RNA target is a mRNA whose functional activity is its ability to be translated. In such cases, the RNAi pathway will decrease the functional activity of the mRNA by translational attenuation or by cleavage. In the instant disclosure, target RNAs are targeted by non-naturally occurring miRNAs. The term "target" can also refer to DNA.

The term "endogenous miRNA" refers to a miRNA produced in an organism through transcription of sequences that naturally are present in the genome of that organism. Endogenous miRNA can be localized in, for example introns, open reading frames (ORFs), 5' or 3' untranslated regions (UTRs), or intergenic regions. The organism which produces an endogenous miRNA may be, without limitation, human (and other primates), mouse, rat, fly, worms, fish or other organisms that have an intact RNAi pathway.

The term "complementary" refers to the liability of polynucleotides to form base pairs with one another. Base pairs are typically formed by hydrogen bonds between nucleotide units in antiparallel polynucleotide strands. Complementary polynucleotide strands can base pair in the Watson-Crick manner (e.g., A to T, A to U, C to G), or in any other manner that allows for the formation of duplexes, including the wobble base pair formed between U and G. As persons skilled in the art are aware, when using RNA as opposed to DNA, uracil rather than thymine is the base that is considered to be complementary to adenosine. However, when a U is denoted in the context of the present invention, the ability to substitute a T is implied, unless otherwise stated.

Perfect complementarity or 100% complementarity refers to the situation in which each nucleotide unit of one polynucleotide strand can hydrogen bond with a nucleotide unit of a second polynucleotide strand. Partial complementarity refers to the situation in which some, but not all, nucleotide units of two strands can hydrogen bond with each other. For example, two strands are at least partially complementary when at least 6-7 base pairs can be formed over a stretch of about 19-25 nucleotides. Sequences are said to be "complementary" to one another when each sequence is the (partial or complete) reverse complement (RC) of the other. For example, the sequence 5' GATC 3' is perfectly complementary to its reverse complement sequence 3' CTAG 5'. Sequences can also have wobble base pairing.

The term "duplex" refers to a double stranded structure formed by two complementary or substantially complementary polynucleotides that form base pairs with one another, including Watson-Crick base pairs and U-G wobble pairs, which allows for a stabilized double stranded structure between polynucleotide strands that are at least partially complementary. The strands of a duplex need not be perfectly complementary for a duplex to form i.e. a duplex may include one or more base mismatches.

A single polynucleotide molecule can possess antiparallel and complementary polynucleotide strands capable of forming a duplex with intramolecular base pairs. Such polynucleotides frequently have a stem-loop structure where the strands of the stem are separated by a loop sequence (which is predominantly single stranded) and are thus able to adopt a mutually antiparallel orientation. Stem-loop structures are well known in the art. Pre-miRNAs and pri-miRNAs often have one or more stem-loop structures in which the stem includes a mature strand-star strand duplex.

The term "nucleotide" refers to a ribonucleotide or a deoxyribonucleotide or modified form thereof, as well as an analog thereof. Nucleotides include species that comprise purines, e.g., adenine, hypoxanthine, guanine, and their derivatives and analogs, as well as pyrimidines, e.g., cytosine, uracil, thymine, and their derivatives and analogs. Nucleotide analogs include nucleotides having modifications in the chemical structure of the base, sugar and/or phosphate, including, but not limited to, 5-position pyrimidine modifications, 8-position purine modifications, modifications at cytosine exocyclic amines, and substitution of 5-bromouracil; and 2'-position sugar modifications, including but not limited to, sugar-modified ribonucleotides in which the 2'-OH is replaced by a group such as an H, OR, R, halo, SH, SR, $NH_2$, NHR, $NR_2$, or CN, wherein R is an alkyl moiety. Nucleotide analogs are also meant to include nucleotides with bases such as inosine, queuosine, xanthine, sugars such as 2'-methyl ribose, non-natural phosphodiester linkages such as methylphosphonates, phosphorothioates and peptides.

Modified bases refer to nucleotide bases such as, for example, adenine, guanine, cytosine, thymine, uracil, xanthine, inosine, and queuosine that have been modified by the replacement or addition of one or more atoms or groups. Some examples of types of modifications that can comprise nucleotides that are modified with respect to the base moieties include but are not limited to, alkylated, halogenated, thiolated, aminated, amidated, or acetylated bases, individually or in combination. More specific examples include, for example, 5-propynyluridine, 5-propynylcytidine, 6-methyladenine, 6-methylguanine, N,N,-dimethyladenine, 2-propyladenine, 2-propylguanine, 2-aminoadenine, 1-methylinosine, 3-methyluridine, 5-methylcytidine, 5-methyluridine and other nucleotides having a modification at the 5 position, 5-(2-amino)propyl uridine, 5-halocytidine, 5-halouridine, 4-acetylcytidine, 1-methyladenosine, 2-methyladenosine, 3-methylcytidine, 6-methyluridine, 2-methylguanosine, 7-methylguanosine, 2,2-dimethylguanosine, 5-methylaminoethyluridine, 5-methyloxyuridine, deazanucleotides such as 7-deaza-adenosine, 6-azouridine, 6-azocytidine, 6-azothymidine, 5-methyl-2-thiouridine, other thio bases such as 2-thiouridine and 4-thiouridine and 2-thiocytidine, dihydrouridine, pseudouridine, queuosine, archaeosine, naphthyl and substituted naphthyl groups, any O- and N-alkylated purines and pyrimidines such as N6-methyladenosine, 5-methylcarbonylmethyluridine, uridine 5-oxyacetic acid, pyridine-4-one, pyridine-2-one, phenyl and modified phenyl groups such as aminophenol or 2,4,6-trimethoxy benzene, modified cytosines that act as G-clamp nucleotides, 8-substituted adenines and guanines, 5-substituted uracils and thymines, azapyrimidines, carboxyhydroxyalkyl nucleotides, carboxyalkylamino nucleotides, and alkylcarbonylalkylated nucleotides. Modified nucleotides also include those nucleotides that are modified with respect to the sugar moiety, as well as nucleotides having sugars or analogs thereof that are not ribosyl. For example, the sugar moieties may be, or be based on, mannoses, arabinoses, glucopyranoses, galactopyranoses, 4'-thioribose, and other sugars, heterocycles, or carbocycles.

The term nucleotide is also meant to include what are known in the art as universal bases. By way of example, universal bases include, but are not limited to, 3-nitropyrrole, 5-nitroindole, or nebularine. The term "nucleotide" is also meant to include the N3' to P5' phosphoramidate, resulting from the substitution of a ribosyl 3'-oxygen with an amine group. Further, the term nucleotide also includes those species that have a detectable label, such as for example a radioactive or fluorescent moiety, or mass label attached to the nucleotide.

The term "polynucleotide" refers to polymers of two or more nucleotides, and includes, but is not limited to, DNA, RNA, DNA/RNA hybrids including polynucleotide chains of regularly and/or irregularly alternating deoxyribosyl moieties and ribosyl moieties (i.e., wherein alternate nucleotide units have an —OH, then and —H, then an —OH, then an —H, and so on at the 2' position of a sugar moiety), and modifications of these kinds of polynucleotides, wherein the attachment of various entities or moieties to the nucleotide units at any position are included.

The term "ribonucleotide" and the term "ribonucleic acid" (RNA), refer to a modified or unmodified nucleotide or polynucleotide comprising at least one ribonucleotide unit. A ribonucleotide unit comprises an hydroxyl group attached to the 2' position of a ribosyl moiety that has a nitrogenous base attached in N-glycosidic linkage at the 1' position of a ribosyl moiety, and a moiety that either allows for linkage to another nucleotide or precludes linkage.

In one aspect, the present disclosure provides non-naturally occurring miRNAs (also sometimes referred to herein as "artificial miRNAs") that are capable of reducing the functional activity of a target RNA. By "non-naturally occurring miRNA" (where miRNA in this context refers to a specific endogenous miRNA) is meant a pre-miRNA or pri-miRNA comprising a stem-loop structure(s) derived from a specific endogenous miRNA in which the stem(s) of the stem-loop structure(s) incorporates a mature strand-star strand duplex where the mature strand sequence is distinct from the endogenous mature strand sequence of the specific referenced endogenous miRNA. The sequence of the star strand of a non-naturally occurring miRNA of the disclosure is also distinct from the endogenous star strand sequence of the specific referenced endogenous miRNA.

The sequences of a non-naturally occurring miRNA outside of the mature strand-star strand duplex (i.e., the loop and the regions of the stem on either side of the mature strand-star strand duplex, and optionally including flanking sequences, as detailed below) are referred to herein as "miRNA scaffold," "scaffold portion," or simply "scaffold." Thus, in another aspect, the disclosure provides miRNA scaffolds useful for the generation of non-naturally occurring miRNAs. A non-naturally occurring miRNA of the disclosure comprises a miRNA scaffold derived from (i.e. at least 60% identical to, up to and including 100% identical to) a specific endogenous miRNA and further comprises a mature strand-star strand duplex that is not derived from that same specific endogenous miRNA. A single miRNA scaffold of the disclosure can be used to provide an almost unlimited number of different non-naturally occurring miRNAs, each having the same miRNA scaffold sequence but different mature strand and star strand sequences.

Note that one skilled in the art will appreciate that the term "a non-naturally occurring miRNA" may refer not only to a RNA molecule, but also in certain contexts to a DNA molecule that encodes such an RNA molecule.

Endogenous miRNAs from which the miRNA scaffold sequences of the disclosure are derived include, but are not limited to, miR-26b, miR-196a-2, and miR-204, from humans (miRNA Accession numbers MIMAT0000083, MIMAT0000226, MIMAT0000265 respectively available and at the http site for microrna.sanger.ac.uk/sequences/index.shtml), as well as miR-26b, miR-196a-2 and miR-204 from other species. In this context, two miRNAs are judged to be equivalent if the mature strand of each sequence is identical or nearly identical. Hence, the term "a non-naturally occurring miR-196-a-2 miRNA" refers to a pre-miRNA or pri-miRNA comprising a miR-196a-2 miRNA scaffold (i.e. a miRNA scaffold derived from miR-196a-2 or an equivalent sequence) and further comprising a mature strand and star strand sequence that is distinct from the endogenous mature strand and star strand sequences of endogenous miR-196a-2. A non-naturally occurring miR-196a-2 miRNA thus comprise a stem-loop structure(s) derived from miR-196a-2 (from any species) in which the stem(s) of the stem-loop structure(s) incorporates a mature strand-star strand duplex where the mature strand sequence is distinct from the endogenous mature strand sequence of miR-196a-2. Similarly, the term "a non-naturally occurring miR-204 miRNA" refers to a pre-miRNA or pri-miRNA comprising a miR-204 miRNA scaffold (i.e. a miRNA scaffold derived from miR-204) and a mature strand and star strand sequence that is not derived from miR-204. A non-naturally occurring miR-204 miRNA thus comprises a stem-loop structure(s) derived from miR-204 (from any species) in which the stem(s) of the stem-loop structure(s) incorporates a mature strand-star strand duplex where the mature strand sequence is distinct from the endogenous mature strand sequence of miR-204.

The miRNA scaffold sequence may be the same as the specifically referenced endogenous miRNA (e.g., miR-196a-2 or miR-204), or it may be different from the specifically referenced endogenous miRNA by virtue of the addition, substitution, or deletion of one or more nucleotides relative to the endogenous miRNA sequence. Such modifications can enhance the functionality of the miRNA scaffold by, for example, introducing restriction sites. Restriction sites can facilitate cloning strategies e.g. by allowing the introduction of mature strand and star strand sequences into the miRNA scaffold, and by allowing introduction of the non-naturally occurring miRNA into a vector construct so that it may be expressed in a cell. In addition, modifications in the miRNA scaffold may be made in order to minimize the functionality of the star strand of a non-naturally occurring miRNA in the RNAi machinery. In addition, nucleotide changes can be made in the miRNA scaffold to minimize the length of the mature strand and the star strand, and yet still yield efficient and specific gene silencing activity. Sequence modifications can also be made to the miRNA scaffold in order to minimize the ability of the star strand in the resulting non-naturally occurring miRNA to interact with RISC. In still another example, the number of nucleotides present in loop of the miRNA scaffold can be reduced to improve manufacturing efficiency.

The miRNA scaffold may also include additional 5' and/or 3' flanking sequences (for example, where it is desired to provide non-naturally occurring miRNA as a pri-miRNA that is first processed by Drosha to yield a pre-miRNA). Such flanking sequences flank the 5' and/or 3' ends of the stem-loop and range from about 5 nucleotides in length to about 600 nucleotides in length, preferably from about 5 nucleotides to about 150 nucleotides in length. The flanking sequences may be the same as the endogenous sequences that flank the 5' end and/or the 3' of the stem-loop structure of endogenous miRNA from which the miRNA scaffold is derived or they may be different by virtue of the addition, deletion, or substitution of one or more base pairs. For example, a miR-196a-2 miRNA scaffold (and a non-naturally occurring miR-196a-2 miRNA obtained by cloning a mature strand sequence and a star strand sequence thereinto) may include 5' and/or 3' flanking sequence which is the same as the endogenous sequences that flank the 5' end and/or the 3' of the stem-loop structure of endogenous miR-196a-2 miRNA.

Figure 4B:
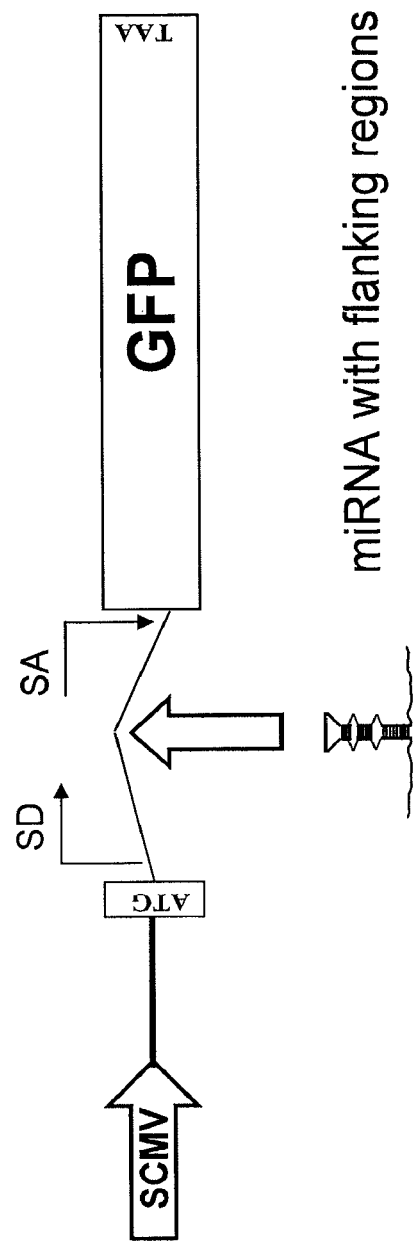
FIG. 4: (A) provides the sequence, restriction sites, and important attributes (e.g., 5' and 3' splice sites, branch points, polypyrimidine tracts) of the artificial intron used in these studies. (B) provides a schematic of the position of the artificial intron in GFP (Green Fluorescent Protein). SD=splice donor, SA=splice acceptor. (C-E) provides the targeting and flanking sequences associated with miR-196a-2, -26b, and -204, respectively. Sequence provided in the 5→3' orientation. The underlined portions of the sequences are illustrated in detail in FIG. 6. (F) diagram of the dual luciferase reporter construct. Schematic diagram of psiCHECK-2 vector (Promega) used to construct cleavage-based reporter plasmids. Vector includes firefly (hluc) and *Renilla* (hRluc) luciferase genes. Target sequence is inserted in the 3' UTR of hRluc.

The 5' and 3' flanking sequences can also be derived from the endogenous sequences that flank the 5' end and/or the 3' of the stem-loop structure of an endogenous miRNA other than the specifically referenced miRNA. For example, in some embodiments a miR-196a-2 miRNA scaffold includes 5' and/or 3' flanking sequences that are derived from the endogenous sequences that flank the 5' end and/or the 3' end of the stem-loop structure of another miRNA, such as miR-204. In other examples, the 5' and/or 3' flanking sequences may be artificial sequences designed or demonstrated to have minimal effects on miRNA folding or processing or functionality. In other examples, the 5' and/or 3' flanking sequences are natural sequences that enhance or do not interfere with the folding or processing of the non-naturally occurring miRNA by Drosha, Dicer, or other components of the RNAi pathway. In addition, flanking sequences can be designed or selected to have one or more nucleotide motifs and/or secondary structures that enhance processing of the non-naturally occurring miRNA to generate the mature miRNA. Thus for instance, if the non-naturally occurring miRNA is intended to be located within an intron for expression purposes, the flanking sequences in the miRNA scaffold can be modified to contain, for instance, splice donor and acceptor sites that enhance excision of the non-naturally occurring miRNA from the expressed gene. Alternatively, if a unique sequence or sequences are identified that enhance miRNA processing, such sequences can be inserted into the 5' and/or 3' flanking sequences. Such sequences might include AU-rich sequences, and sequences that have affinity with one or more components of the RNAi machinery, and sequences that form secondary structures that enhance processing by the RNAi machinery. In one embodiment, the flanking sequence comprises the artificial intron sequence in FIG. 4.

In still other embodiments, the 5' and/or 3' flanking sequences in the miRNA scaffold may be derived from a different species than the other portions of the miRNA scaffold. For example, the 5' and/or 3' flanking sequences in a miR-196a-2 miRNA scaffold may be derived from the flanking regions of rat miR-196a-2 (or indeed from the flanking regions of another rat miR) whereas the remainder of the miR-196a-2 miRNA scaffold is derived from human miR-196a-2.

The miRNA scaffolds of the disclosure 1) contain well-defined stem and loop structures, 2) have minimal secondary structures, 3) are modifiable to facilitate cloning, 4) permit a non-naturally occurring miRNA to be expressed from a Pol II or Pol III promoter, 5) are amenable to changes that alter loop size and sequence, 6) permit a non-naturally occurring miRNA to function when maintained epigenetically (i.e. as plasmids) or are inserted into the host genome, and 7) are amenable to insertion or substitution of foreign sequences at the position of the endogenous mature miRNA sequence in order to generate a non-naturally occurring miRNA. In cases where the scaffold is associated with e.g. a reporter gene (such as GFP) or selectable marker gene (such as puromycin), or both, preferred miRNA scaffolds can perform regardless of whether they are inserted in the 5' UTR, 3' UTR, intronic sequences or ORF of said genes. In one preferred configuration, a fusion construct comprising the gene encoding GFP is functionally fused to a gene encoding puromycin with the sequence encoding Peptide 2A functionally separating the two coding sequences, and the artificial miRNA-196a-2 inserted in the 3' UTR of the fusion construct. FIG. 6F and FIG. 6G illustrate non-limiting examples of miR-204 and miR-196a-2 scaffolds, respectively, in which the site of mature strand and the star strand insertion is depicted schematically. Nucleotide substitutions (relative to endogenous miR-204 and miR-196a-2) are indicated by use of upper case format; such substitutions introduce restriction sites (indicated) to facilitate cloning.

As disclosed above, a non-naturally occurring miRNA of the disclosure comprises a miRNA scaffold derived from a specific endogenous miRNA and further comprises a mature strand-star strand duplex that is not derived from that same specific endogenous miRNA. The mature strand of the non-naturally occurring miRNAs of the disclosure can be the same length, longer, or shorter than the endogenous miRNA from which the scaffold is derived. The exact length of the mature strand of a non-naturally occurring miRNA of the disclosure is not important so long as the resulting non-naturally occurring miRNA is capable of being processed by Drosha and/or Dicer.

The nucleotide sequence of the mature strand of a non-naturally occurring miRNA of the disclosure can be 1) the same as, or derived from, a mature strand from another endogenous miRNA; 2) selected based on a target mRNA sequence; or 3) rationally selected based on a target mRNA sequence. These three sources of mature strand sequences will now be discussed in turn.

Embodiments where the Mature Strand is from Another Endogenous miRNA (shMIMICS)

In a first series of embodiments, the sequence of the mature strand of a non-naturally occurring miRNA is derived from (i.e. at least 60% identical to, up to and including 100% identical to) the sequence of the mature strand of another endogenous miRNA distinct from the miRNA from which the miRNA scaffold portion of the non-naturally occurring miRNA is derived. We sometimes refer to such a non-naturally occurring miRNA as a "shMIMIC." Such shMIMICs thus have a stem-loop structure comprising a scaffold derived from a first endogenous miRNA, a mature strand derived from a second endogenous miRNA, and a star strand sequence that is at least partially complementary to the mature strand sequence.

Figure 11:
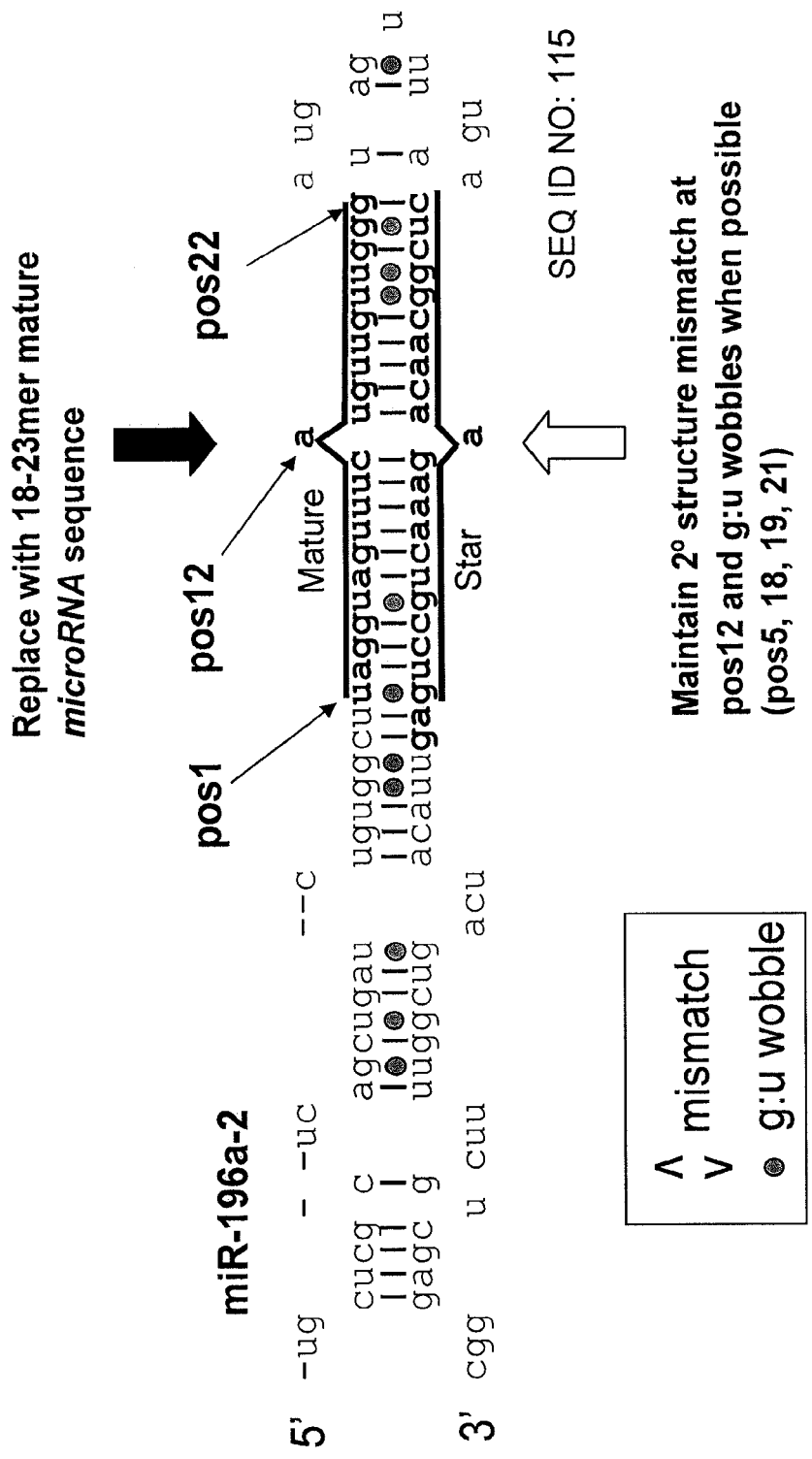
FIG. 11 shows the overall design strategy for a miR-196a-2 shMIMIC. The endogenous 22 nucleotide mature strand and star strand sequences are indicated (as discussed in the description of FIG. 6 and below there is also evidence that miR-196a-2 has a 21 nucleotide mature strand which would not include the base at pos 22 (which corresponds to the base marked with an * in FIG. 6)). The endogenous mature strand sequence is replaced with, for example, an 18-23 nucleotide sequence derived from another endogenous miR. The endogenous star strand sequence is replaced with a sequence that is for the most part the reverse complement of the new mature strand, but contains some local sequence modifications in order to mimic the secondary structure of endogenous miR-196a-2. These modifications include the introduction of a mismatch between the nucleotide at position 12 of the mature strand and the opposite position on the star strand, and g:u wobble pairs between nucleotides at positions 5, 18, 19 (if present) and 21 (if present) on the mature strand and the opposite positions on the star strand. Note that a 23 nucleotide mature strand (or longer) may be provided by adding additional nucleotide(s) after (i.e. 3' of) position 22, along with additional nucleotide(s) opposite that position on the star strand (preferably so that Watson-Crick base pairs are formed).

For example, a miR-196a-2 shMIMIC has a miRNA scaffold structure derived from miR-196a-2 but has a mature strand derived from the mature strand of an endogenous miRNA other than miR-196a-2. Preferably, the mature strand sequence of a miR-196a-2 shMIMIC is about 18 to about 23 nucleotides in length, for example 18, 19, 20, 21, 22, or 23 nucleotides in length. However, the length of the mature strand sequence is not critical so long as the shMIMIC is recognized and processed by Drosha and Dicer. Accordingly, mature strand sequences shorter than 18 nucleotides and longer than 23 nucleotides may also be accommodated within a miR-196a-2 scaffold. FIG. 11 provides general design considerations for shMIMICs based on the miR-196a-2 scaffold.

In one series of embodiments, a miR-196a-2 shMIMIC has a mature strand sequence derived from the sequence of the mature strand of any of the following miRNAs from *Homo sapiens* (hsa): hsa-let-7a-1, hsa-let-7a-2, hsa-let-7a-3, hsa-let-7b, hsa-let-7c, hsa-let-7d, hsa-let-7e, hsa-let-7f-1, hsa-let-7f-2, hsa-let-7g, hsa-let-7i, hsa-mir-1-1, hsa-mir-1-2, hsa-mir-7-1, hsa-mir-7-2, hsa-mir-7-3, hsa-mir-9-1, hsa-mir-9-2, hsa-mir-9-3, hsa-mir-10a, hsa-mir-10b, hsa-mir-15a, hsa-mir-15b, hsa-mir-16-1, hsa-mir-16-2, hsa-mir-17, hsa-mir-18a, hsa-mir-18b, hsa-mir-19a, hsa-mir-19b-1, hsa-mir-19b-2, hsa-mir-20a, hsa-mir-20b, hsa-mir-21, hsa-mir-22, hsa-mir-23a, hsa-mir-23b, hsa-mir-24-1, hsa-mir-24-2, hsa-mir-25, hsa-mir-26a-1, hsa-mir-26a-2, hsa-mir-26b, hsa-mir-27a, hsa-mir-27b, hsa-mir-28, hsa-mir-29a, hsa-mir-29b-1, hsa-mir-29b-2, hsa-mir-29c, hsa-mir-30a, hsa-mir-30b, hsa-mir-30c-1, hsa-mir-30c-2, hsa-mir-30d, hsa-mir-30e, hsa-mir-31, hsa-mir-32, hsa-mir-33a, hsa-mir-33b, hsa-mir-34a, hsa-mir-34b, hsa-mir-34c, hsa-mir-92a-1, hsa-mir-92a-2, hsa-mir-92b, hsa-mir-93, hsa-mir-95, hsa-mir-96, hsa-mir-98, hsa-mir-99a, hsa-mir-99b, hsa-mir-100, hsa-mir-101-1, hsa-mir-101-2, hsa-mir-103-1, hsa-mir-103-2, hsa-mir-105-1, hsa-mir-105-2, hsa-mir-106a, hsa-mir-106b, hsa-mir-107, hsa-mir-122, hsa-mir-124-1, hsa-mir-124-2, hsa-mir-124-3, hsa-mir-125a, hsa-mir-125b-1, hsa-mir-125b-2, hsa-mir-126, hsa-mir-127, hsa-mir-128-1, hsa-mir-128-2, hsa-mir-129-1, hsa-mir-129-2, hsa-mir-130a, hsa-mir-130b, hsa-mir-132, hsa-mir-133a-1, hsa-mir-133a-2, hsa-mir-133b, hsa-mir-134, hsa-mir-135a-1, hsa-mir-135a-2, hsa-mir-135b, hsa-mir-136, hsa-mir-137, hsa-mir-138-1, hsa-mir-138-2, hsa-mir-139, hsa-mir-140, hsa-mir-141, hsa-mir-142, hsa-mir-143, hsa-mir-144, hsa-mir-145, hsa-mir-146a, hsa-mir-146b, hsa-mir-147, hsa-mir-147b, hsa-mir-148a, hsa-mir-148b, hsa-mir-149, hsa-mir-150, hsa-mir-151, hsa-mir-152, hsa-mir-153-1, hsa-mir-153-2, hsa-mir-154, hsa-mir-155, hsa-mir-181a-1, hsa-mir-181a-2, hsa-mir-181b-1, hsa-mir-181b-2, hsa-mir-181c, hsa-mir-181d, hsa-mir-182, hsa-mir-183, hsa-mir-184, hsa-mir-185, hsa-mir-186, hsa-mir-187, hsa-mir-188, hsa-mir-190, hsa-mir-190b, hsa-mir-191, hsa-mir-192, hsa-mir-193a, hsa-mir-193b, hsa-mir-194-1, hsa-mir-194-2, hsa-mir-195, hsa-mir-196a-1, hsa-mir-196b, hsa-mir-197, hsa-mir-198, hsa-mir-199a-1, hsa-mir-199a-2, hsa-mir-199b, hsa-mir-200a, hsa-mir-200b, hsa-mir-200c, hsa-mir-202, hsa-mir-203, hsa-mir-204, hsa-mir-205, hsa-mir-206, hsa-mir-208a, hsa-mir-208b, hsa-mir-210, hsa-mir-211, hsa-mir-212, hsa-mir-214, hsa-mir-215, hsa-mir-216a, hsa-mir-216b, hsa-mir-217, hsa-mir-218-1, hsa-mir-218-2, hsa-mir-219-1, hsa-mir-219-2, hsa-mir-220a, hsa-mir-220b, hsa-mir-220c, hsa-mir-221, hsa-mir-222, hsa-mir-223, hsa-mir-224, hsa-mir-296, hsa-mir-297, hsa-mir-298, hsa-mir-299, hsa-mir-300, hsa-mir-301a, hsa-mir-301b, hsa-mir-302a, hsa-mir-302b, hsa-mir-302c, hsa-mir-302d, hsa-mir-302e, hsa-mir-302f, hsa-mir-320a, hsa-mir-320b-1, hsa-mir-320b-2, hsa-mir-320c-1, hsa-mir-320c-2, hsa-mir-320d-1, hsa-mir-320d-2, hsa-mir-323, hsa-mir-324, hsa-mir-325, hsa-mir-326, hsa-mir-328, hsa-mir-329-1, hsa-mir-329-2, hsa-mir-330, hsa-mir-331, hsa-mir-335, hsa-mir-337, hsa-mir-338, hsa-mir-339, hsa-mir-340, hsa-mir-342, hsa-mir-345, hsa-mir-346, hsa-mir-361, hsa-mir-362, hsa-mir-363, hsa-mir-365-1, hsa-mir-365-2, hsa-mir-367, hsa-mir-369, hsa-mir-370, hsa-mir-371, hsa-mir-372, hsa-mir-373, hsa-mir-374a, hsa-mir-374b, hsa-mir-375, hsa-mir-376a-1, hsa-mir-376a-2, hsa-mir-376b, hsa-mir-376c, hsa-mir-377, hsa-mir-378, hsa-mir-379, hsa-mir-380, hsa-mir-381, hsa-mir-382, hsa-mir-383, hsa-mir-384, hsa-mir-409, hsa-mir-410, hsa-mir-411, hsa-mir-412, hsa-mir-421, hsa-mir-422a, hsa-mir-423, hsa-mir-424, hsa-mir-425, hsa-mir-429, hsa-mir-431, hsa-mir-432, hsa-mir-433, hsa-mir-448, hsa-mir-449a, hsa-mir-449b, hsa-mir-450a-1, hsa-mir-450a-2, hsa-mir-450b, hsa-mir-451, hsa-mir-452, hsa-mir-453, hsa-mir-454, hsa-mir-455, hsa-mir-483, hsa-mir-484, hsa-mir-485, hsa-mir-486, hsa-mir-487a, hsa-mir-487b, hsa-mir-488, hsa-mir-489, hsa-mir-490, hsa-mir-491, hsa-mir-492, hsa-mir-493, hsa-mir-494, hsa-mir-495, hsa-mir-496, hsa-mir-497, hsa-mir-498, hsa-mir-499, hsa-mir-500, hsa-mir-501, hsa-mir-502, hsa-mir-503, hsa-mir-504, hsa-mir-505, hsa-mir-506, hsa-mir-507, hsa-mir-508, hsa-mir-509-1, hsa-mir-509-2, hsa-mir-509-3, hsa-mir-510, hsa-mir-511-1, hsa-mir-511-2, hsa-mir-512-1, hsa-mir-512-2, hsa-mir-513a-1, hsa-mir-513a-2, hsa-mir-513b, hsa-mir-513c, hsa-mir-514-1, hsa-mir-514-2, hsa-mir-514-3, hsa-mir-515-1, hsa-mir-515-2, hsa-mir-516a-1, hsa-mir-516a-2, hsa-mir-516b-1, hsa-mir-516b-2, hsa-mir-517a, hsa-mir-517b, hsa-mir-517c, hsa-mir-518a-1, hsa-mir-518a-2, hsa-mir-518b, hsa-mir-518c, hsa-mir-518d, hsa-mir-518e, hsa-mir-518f, hsa-mir-519a-1, hsa-mir-519a-2, hsa-mir-519b, hsa-mir-519c, hsa-mir-519d, hsa-mir-519e, hsa-mir-520a, hsa-mir-520b, hsa-mir-520c, hsa-mir-520d, hsa-mir-520e, hsa-mir-520f, hsa-mir-520g, hsa-mir-520h, hsa-mir-521-1, hsa-mir-521-2, hsa-mir-522, hsa-mir-523, hsa-mir-524, hsa-mir-525, hsa-mir-526a-1, hsa-mir-526a-2, hsa-mir-526b, hsa-mir-527, hsa-mir-532, hsa-mir-539, hsa-mir-541, hsa-mir-542, hsa-mir-543, hsa-mir-544, hsa-mir-545, hsa-mir-548a-1, hsa-mir-548a-2, hsa-mir-548a-3, hsa-mir-548b, hsa-mir-548c, hsa-mir-548d-1, hsa-mir-548d-2, hsa-mir-548e, hsa-mir-548f-1, hsa-mir-548f-2, hsa-mir-548f-3, hsa-mir-548f-4, hsa-mir-548f-5, hsa-mir-548g, hsa-mir-548h-1, hsa-mir-548h-2, hsa-mir-548h-3, hsa-mir-548h-4, hsa-mir-548i-1, hsa-mir-548i-2, hsa-mir-548i-3, hsa-mir-548i-4, hsa-mir-548j, hsa-mir-548k, hsa-mir-548l, hsa-mir-548m, hsa-mir-548n, hsa-mir-548o, hsa-mir-548p, hsa-mir-549, hsa-mir-550-1, hsa-mir-550-2, hsa-mir-551a, hsa-mir-551b, hsa-mir-552, hsa-mir-553, hsa-mir-554, hsa-mir-555, hsa-mir-556, hsa-mir-557, hsa-mir-558, hsa-mir-559, hsa-mir-561, hsa-mir-562, hsa-mir-563, hsa-mir-564, hsa-mir-566, hsa-mir-567, hsa-mir-568, hsa-mir-569, hsa-mir-570, hsa-mir-571, hsa-mir-572, hsa-mir-573, hsa-mir-574, hsa-mir-575, hsa-mir-576, hsa-mir-577, hsa-mir-578, hsa-mir-579, hsa-mir-580, hsa-mir-581, hsa-mir-582, hsa-mir-583, hsa-mir-584, hsa-mir-585, hsa-mir-586, hsa-mir-587, hsa-mir-588, hsa-mir-589, hsa-mir-590, hsa-mir-591, hsa-mir-592, hsa-mir-593, hsa-mir-595, hsa-mir-596, hsa-mir-597, hsa-mir-598, hsa-mir-599, hsa-mir-600, hsa-mir-601, hsa-mir-602, hsa-mir-603, hsa-mir-604, hsa-mir-605, hsa-mir-606, hsa-mir-607, hsa-mir-608, hsa-mir-609, hsa-mir-610, hsa-mir-611, hsa-mir-612, hsa-mir-613, hsa-mir-614, hsa-mir-615, hsa-mir-616, hsa-mir-617, hsa-mir-618, hsa-mir-619, hsa-mir-620, hsa-mir-621, hsa-mir-622, hsa-mir-623, hsa-mir-624, hsa-mir-625, hsa-mir-626, hsa-mir-627, hsa-mir-628, hsa-mir-629, hsa-mir-630, hsa-mir-631, hsa-mir-632, hsa-mir-633, hsa-mir-634, hsa-mir-635, hsa-mir-636, hsa-mir-637, hsa-mir-638, hsa-mir-639, hsa-mir-640, hsa-mir-641, hsa-mir-642, hsa-mir-643, hsa-mir-644, hsa-mir-645, hsa-mir-646, hsa-mir-647, hsa-mir-648, hsa-mir-649, hsa-mir-650, hsa-mir-651, hsa-mir-652, hsa-mir-653, hsa-mir-654, hsa-mir-655, hsa-mir-656, hsa-mir-657, hsa-mir-658, hsa-mir-659, hsa-mir-660, hsa-mir-661, hsa-mir-662, hsa-mir-663, hsa-mir-663b, hsa-mir-664, hsa-mir-665, hsa-mir-668, hsa-mir-671, hsa-mir-675, hsa-mir-708, hsa-mir-720, hsa-mir-744, hsa-mir-758, hsa-mir-760, hsa-mir-765, hsa-mir-766, hsa-mir-767, hsa-mir-768, hsa-mir-769, hsa-mir-770, hsa-mir-802, hsa-mir-873, hsa-mir-874, hsa-mir-875, hsa-mir-876, hsa-mir-877, hsa-mir-885, hsa-mir-886, hsa-mir-887, hsa-mir-888, hsa-mir-889, hsa-mir-890, hsa-mir-891a, hsa-mir-891b, hsa-mir-892a, hsa-mir-892b, hsa-mir-920, hsa-mir-921, hsa-mir-922, hsa-mir-923, hsa-mir-924, hsa-mir-933, hsa-mir-934, hsa-mir-935, hsa-mir-936, hsa-mir-937, hsa-mir-938, hsa-mir-939, hsa-mir-940, hsa-mir-941-1, hsa-mir-941-2, hsa-mir-941-3, hsa-mir-941-4, hsa-mir-942, hsa-mir-943, hsa-mir-944, hsa-mir-1178, hsa-mir-1179, hsa-mir-1180, hsa-mir-1181, hsa-mir-1182, hsa-mir-1183, hsa-mir-1184, hsa-mir-1185-1, hsa-mir-1185-2, hsa-mir-1197, hsa-mir-1200, hsa-mir-1201, hsa-mir-1202, hsa-mir-1203, hsa-mir-1204, hsa-mir-1205, hsa-mir-1206, hsa-mir-1207, hsa-mir-1208, hsa-mir-1224, hsa-mir-1225, hsa-mir-1226, hsa-mir-1227, hsa-mir-1228, hsa-mir-1229, hsa-mir-1231, hsa-mir-1233, hsa-mir-1234, hsa-mir-1236, hsa-mir-1237, hsa-mir-1238, hsa-mir-1243, hsa-mir-1244, hsa-mir-1245, hsa-mir-1246, hsa-mir-1247, hsa-mir-1248, hsa-mir-1249, hsa-mir-1250, hsa-mir-1251, hsa-mir-1252, hsa-mir-1253, hsa-mir-1254, hsa-mir-1255a, hsa-mir-1255b-1, hsa-mir-1255b-2, hsa-mir-1256, hsa-mir-1257, hsa-mir-1258, hsa-mir-1259, hsa-mir-1260, hsa-mir-1261, hsa-mir-1262, hsa-mir-1263, hsa-mir-1264, hsa-mir-1265, hsa-mir-1266, hsa-mir-1267, hsa-mir-1268, hsa-mir-1269, hsa-mir-1270, hsa-mir-1271, hsa-mir-1272, hsa-mir-1273, hsa-mir-1274a, hsa-mir-1274b, hsa-mir-1275, hsa-mir-1276, hsa-mir-1277, hsa-mir-1278, hsa-mir-1279, hsa-mir-1280, hsa-mir-1281, hsa-mir-1282, hsa-mir-1283-1, hsa-mir-1283-2, hsa-mir-1284, hsa-mir-1285-1, hsa-mir-1285-2, hsa-mir-1286, hsa-mir-1287, hsa-mir-1288, hsa-mir-1289-1, hsa-mir-1289-2, hsa-mir-1290, hsa-mir-1291, hsa-mir-1292, hsa-mir-1293, hsa-mir-1294, hsa-mir-1295, hsa-mir-1296, hsa-mir-1297, hsa-mir-1298, hsa-mir-1299, hsa-mir-1300, hsa-mir-1301, hsa-mir-1302-1, hsa-mir-1302-2, hsa-mir-1302-3, hsa-mir-1302-4, hsa-mir-1302-5, hsa-mir-1302-6, hsa-mir-1302-7, hsa-mir-1302-8, hsa-mir-1303, hsa-mir-1304, hsa-mir-1305, hsa-mir-1306, hsa-mir-1307, hsa-mir-1308, hsa-mir-1321, hsa-mir-1322, hsa-mir-1323, hsa-mir-1324, hsa-mir-1825, hsa-mir-1826, or hsa-mir-1827.

Similarly, a miR-204 shMIMIC has a miRNA scaffold structure derived from miR-204 but has a mature strand derived from the mature strand of an endogenous miRNA other than miR-204 (including miR-196a-2 and any of the miRs in the preceding paragraph).

The sequence of the mature strand of a shMIMIC may be identical to the endogenous sequence, or it may be modified relative to the endogenous sequence in order to optimize the functional activity of the mature strand in the particular miRNA scaffold. For example, the inventors have shown that a U is preferred at position 1 of the mature strand for efficient targeting to occur using the miR-196a-2 scaffold. In cases where the mature strand sequence to be inserted into the miR-196a-2 scaffold has a nucleotide other than a U at position 1, preferably that sequence will be altered so that a U occurs at the first position. Without being bound by theory or mechanism, it is believed that mature strands anneal to their target mRNA primarily through positions 2-7. For this reason, changing position 1 of a mature strand of a particular miRNA in a shMIMIC is unlikely to change the target specificity of that miRNA.

Figure 3:
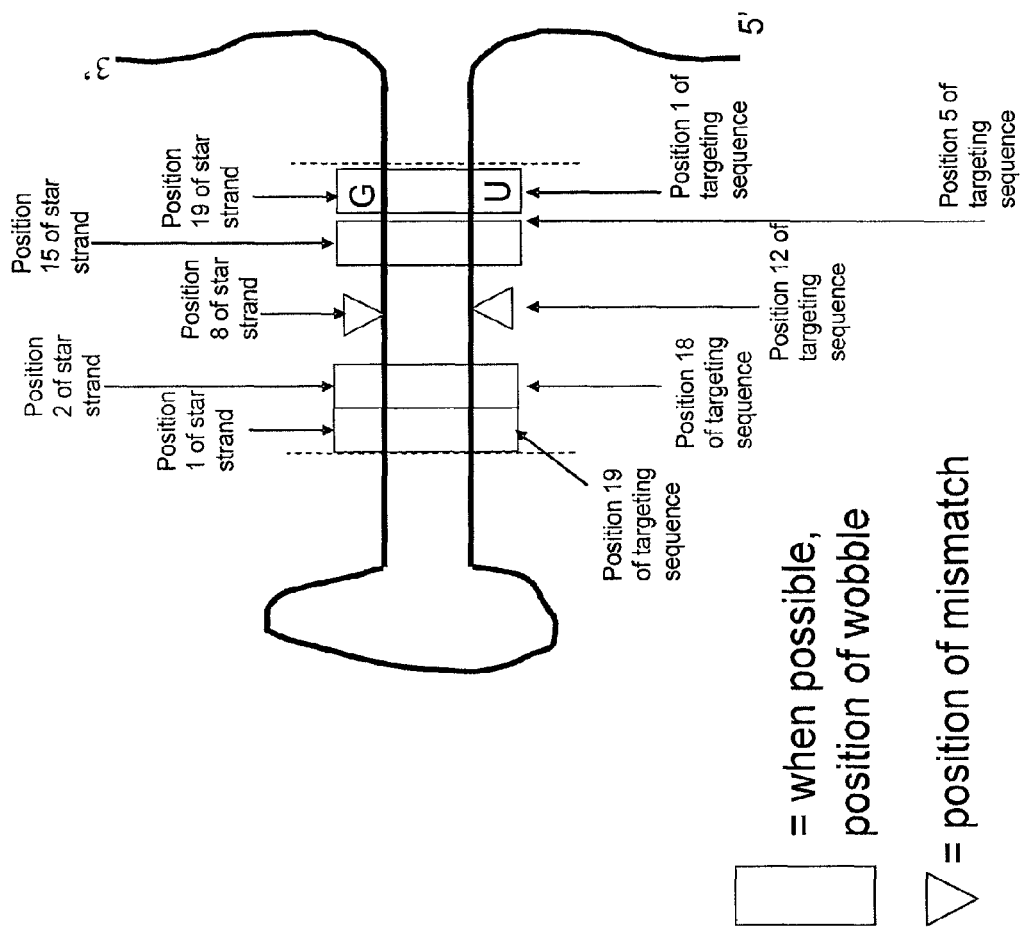
FIG. 3: Schematic drawing identifying several of the key positions in the miR-196a-2 scaffold that can contain secondary structure and non-Watson-Crick base pairing. Positions in both the mature (targeting) and star strand are indicated.

The star strand of a shMIMIC is (for the most part) the reverse complement of the mature strand, but preferably has some alterations to create local structure to mimic the structure of the endogenous mature strand-star strand duplex of the miRNA from which the scaffold is derived. Star strand attributes for a miR-196a-2 shMIMIC, for example, preferably include one or more of the following shown in FIG. 3 and described in detail below.

1. When position 1 of the mature strand is a U (which, as discussed above, is preferable but not mandatory), the star strand position opposite is preferably a G to ensure it will always wobble pair
2. If position 5 of the mature strand is G or T (U), then the star strand position opposite it is preferably altered to be T(U) or G (respectively) to create a wobble pair.
3. If the mature strand has something other than G or T at position 5, then the star strand position opposite is designed to generate a standard Watson-Crick pair.
4. A mismatch is preferably created between position 12 of the mature strand and the opposite position of the star strand. This can be achieved by the relevant position of the star strand having the same base as position 12 of the mature strand.
5. If the mature strand is 18 nucleotides or longer in length, then same criteria that are applied to positions 5 of the mature strand and the opposite position of the star strand are similarly applied to positions 18 of the mature strand and the opposite position of the star strand. Specifically, if position 18 of the mature strand is G or T (U), then the star strand position opposite it is altered to be T(U) or G, respectively, to create a wobble pair. If the mature strand has something other than G or T at position 18, then the star strand position opposite this position is designed to generate a standard Watson-Crick pair
6. If the mature strand is 19 nucleotides or longer in length, then the same criteria that are applied to positions 5 of the mature strand and the opposite position of the star strand are similarly applied to positions 19 of the mature strand and the opposite position of the star strand. Specifically, if position 19 of the mature strand is G or T (U), then the star strand position opposite it is altered to be T(U) or G (respectively) to create a wobble pair. If the mature strand has something other than G or T(U) at position 19, then the star strand is designed to generate a standard Watson-Crick pair.
7. If the mature strand is 21 nucleotides or longer in length, then the same criteria that are applied to positions 5 of the mature strand and the opposite position of the star strand are similarly applied to positions 21 of the mature strand and the opposite position of the star strand. Specifically, if position 21 of the mature strand is G or T (U), then the star strand position opposite it is altered to be T(U) or G (respectively) to create a wobble pair. If the mature strand has something other than G or T(U) at position 21, then the star strand is designed to generate a standard Watson-Crick pair.

The shMIMICS of the instant disclosure are particularly useful for standardizing the expression and activity level of different mature strands. If a plurality of shMIMICS all share the same scaffold sequence, and differ only in the sequence of the mature strand (and star strand) then it can be assumed that each will be expressed and processed by Dicer and RISC to the same extent. Thus, side-by-side comparisons of the effects of expressing different endogenous mature strands in cells can be made. If the endogenous pri-miRNAs corresponding to each mature strand were expressed in cells, such comparisons would be difficult as each pri-miRNA would be processed by Dicer and RISC to a different extent. Moreover, the star strand has varying levels of functionality for each of the endogenous pri-miRNAs. If one is looking at the function of the mature strand in the context of it's endogenous scaffold, it is not possible to distinguish the effects, perhaps minor, of the mature strand from the star strand. In the case of expressing miRNAs from a non-endogenous scaffold (i.e. as a shMIMIC), the star strand is modified to maintain the secondary structure of the scaffold, and therefore the sequence of the star strand is not the same as the endogenous star strand. Therefore, the observed functionality is only for the mature strand and does not include functionality of the star strand of the shMIMIC.

Embodiments where the Mature Strand is Rationally Selected

In another series of embodiments, the mature strand sequences inserted into the miRNA scaffolds of the disclosure are rationally designed. Designing sequences for a miRNA scaffold includes two steps: identification of preferred target sites in the gene to be targeted, and optimizing the scaffold around the selected sequences to ensure structural elements are preserved in the expressed molecule. Identifying target sites can be achieved by several methods. According to one embodiment, the disclosure provides a method for identifying attributes that are 1) important for and/or 2) detrimental to functionality of a targeting sequence embedded in a scaffold. The method comprises: (a) selecting a set of randomly-selected sequences targeting a gene (i.e. mature strand sequences that are at least partially complementary to a target RNA); (b) incorporating those sequences into the scaffold of choice, (c) determining the relative functionality of each sequence in the context of the scaffold, (d) determining how the presence or absence of at least one variable affect functionality, and (e) developing an algorithm for selecting functional sequences using the information of step (d).

Methods for detecting the efficiency of target knockdown (step (c)) by sequences include quantitating target gene mRNA and/or protein levels. For mRNA, standard techniques including PCR-based methods, northern blots, and branched DNA can be applied. For protein quantitation, methods based on ELISA, western blotting, and the like can be used to assess the functionality of sequences. One preferred protein detection assay is based on a reporter system such as the dual-luciferase reporter vector system (e.g. psiCheck, Promega) containing short target sequences for each targeting sequence that can be used to assess the functionality of each sequence.

Side-by-side analysis of functional and non-functional sequences can identify positions or regions where particular nucleotides, thermodynamic profiles, secondary structures, and more, enhance or negatively affect functionality. By merging these elements (both positive and negative) in a weighted fashion, a selection algorithm can be assembled.

In one embodiment, the present disclosure provides a method for identifying functional target sites for the miR-196a-2 scaffold. The method comprises applying selection criteria (identified by bioinformatic analysis of functional and non-functional sets of sequences) to a set of potential sequences that comprise about 18-23 base pairs (although longer or shorter sequences are also specifically contemplated), where the selection criteria are non-target specific criteria and species independent. Preferred selection criteria include both positively and negatively weighted elements associated with 1) nucleotides at particular positions, 2) regiospecific thermodynamic profiles at particular positions, 3) elimination or incorporation of possible secondary structures within the targeting sequence, and other factors. Application of one or more of these selection criteria allow rational design of sequences to be inserted into the miR-196a-2 scaffold.

In one embodiment, the selection criteria are embodied in a formula. For example, formula I provided below may be used to determine nucleotides 1-19 (numbered in the 5' to 3' direction) of the mature strand (which may be a 19 nucleotide to, for example, a 25 nucleotide mature strand) of highly functional non-naturally occurring miR-196a-2 gene targeting sequences.

Figure 2:
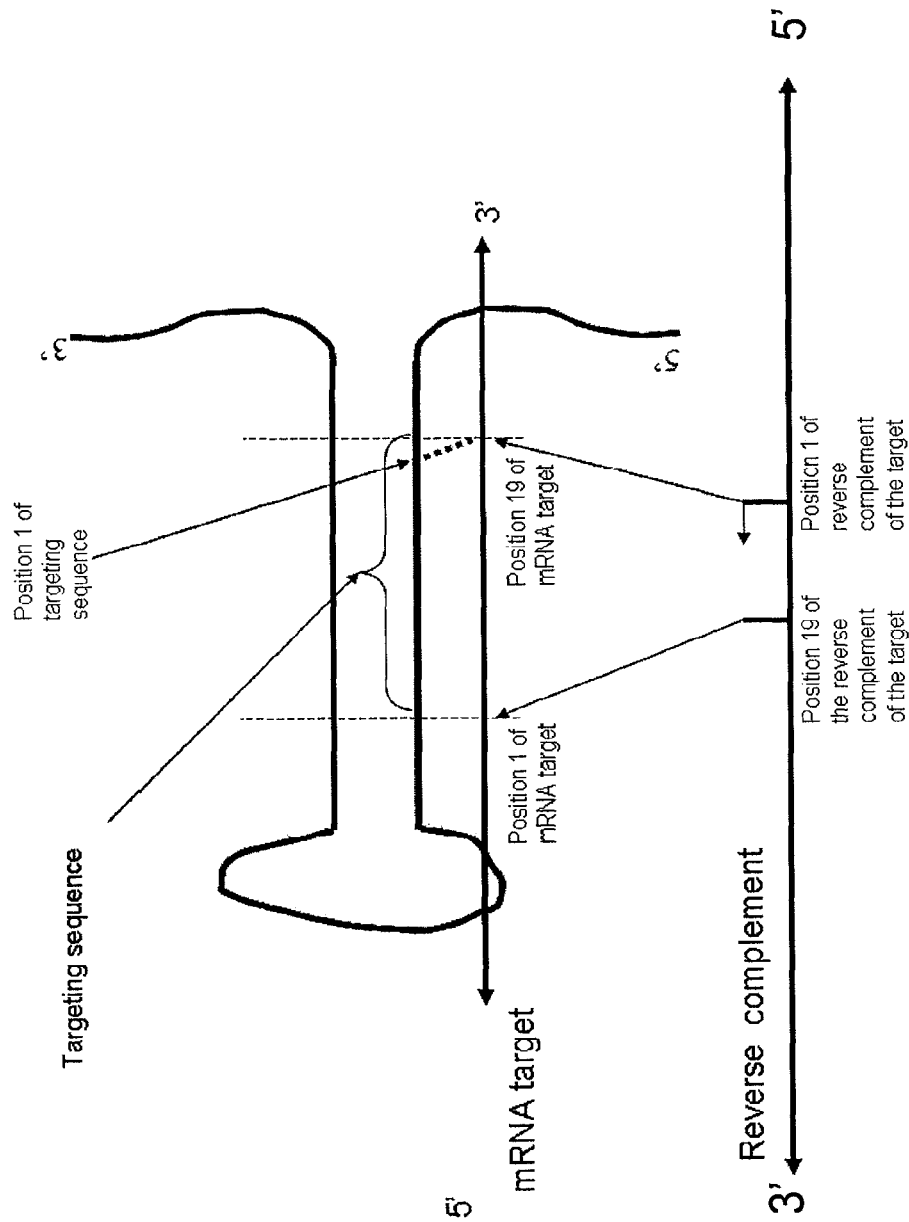
FIG. 2: Schematic drawing demonstrating the relative orientation of the targeting sequence (in the scaffold) with respect to the target sequence (mRNA) and the reverse complement.

Formula I: for nucleotides 1-19 of the reverse complement of the target sequence.

$$\begin{aligned}\text{Score}=&(-500)*A1+(43.8)*T1+(-21.3)*C1+\\&(-500)*G1+(21.3)*T5+(18.8)*A6+(-3)*T6+\\&(25)*A7+(-41.3)*G7+(21.3)*T8+(-16.3)*C8+\\&(37.5)*T12+(-18.8)*G12+(27.5)*T13+\\&(-22.5)*C13+(21.3)*T15+(-17.5)*G15+\\&(-18.8)*G16+(-18.8)*G17+(16.3)*T18+\\&(-17.5)*G18+(21.3)*T19+(28.8)*C19+\\&(-35)*G19\end{aligned}$$

where "A" represents an adenine, "G" represents a guanine, "T" represents a thymine, and "C" represents a cytosine. In addition, the number following the symbol for each base (e.g. A1) refers to the position of the base. in the reverse complement of the target mRNA. As such, the reverse complement (RC) nucleotide 1 in the algorithm is the complement of nucleotide 19 in the target mRNA (see FIG. 2). Furthermore, nucleotide 19 of the target mRNA base pairs or wobble pairs with nucleotide 1 of the mature strand which is inserted into the miRNA scaffold. Table 1 below indicates the aligned nucleotide positions, where $M_1$-$M_{19}$ are nucleotides 1-19 of the mature strand; $R_1$-$R_{19}$ are nucleotides 1-19 of the target RNA, and nucleotides $S_1$-$S_{19}$ are nucleotides 1-19 of the star strand:

TABLE 1

| 3' | $S_{19}$ | $S_{18}$ | $S_{17}$ | $S_{16}$ | $S_{15}$ | $S_{14}$ | $S_{13}$ | $S_{12}$ | $S_{11}$ | $S_{10}$ | $S_9$ | $S_8$ | $S_7$ | $S_6$ | $S_5$ | $S_4$ | $S_3$ | $S_2$ | $S_1$ | 5' |
|---|---|---|---|---|---|---|---|---|---|---|---|---|---|---|---|---|---|---|---|---|
| 5' | $M_1$ | $M_2$ | $M_3$ | $M_4$ | $M_5$ | $M_6$ | $M_7$ | $M_8$ | $M_9$ | $M_{10}$ | $M_{11}$ | $M_{12}$ | $M_{13}$ | $M_{14}$ | $M_{15}$ | $M_{16}$ | $M_{17}$ | $M_{18}$ | $M_{19}$ | 3' |
| 3' | $R_{19}$ | $R_{18}$ | $R_{17}$ | $R_{16}$ | $R_{15}$ | $R_{14}$ | $R_{13}$ | $R_{12}$ | $R_{11}$ | $R_{10}$ | $R_9$ | $R_8$ | $R_7$ | $R_6$ | $R_5$ | $R_4$ | $R_3$ | $R_2$ | $R_1$ | 5' |

Detailed studies of functional and non-functional sequences identified a preference for a "U" at position 1 of the mature strand of non-naturally occurring miR-196a-2 miRNAs. Therefore, a U at position 1 of the mature strand is highly desirable. Taking this into account, an "A" or "G." at position 1 of the reverse complement of the target is highly negatively weighted (−500). A "C" at position 1 is also selected against (−21.3) albeit the weighting is less severe because a "C" at this position still allows a GU wobble to occur in the mature-target duplex. In contrast, a "T" at position 1 of the RC of the target is highly desirable (+43.8). (Note: "U" refers to the nucleotide as it appears in the RNA molecule, "T" refers to the nucleotide as it appears in the cDNA of the RNA molecule)

Note that there is evidence to support both a 21 nucleotide endogenous mature strand (with the 3' terminus being GG) and a 22 nucleotide endogenous mature strand (with the 3' terminus being GGG) for miR-196a-2. If the mature strand of a non-naturally occurring miR-196a-2 is longer than 19 nucleotides (with additional nucleotides added to the 3' end), then the star strand will also include additional nucleotides at its 5' end such that the star strand and the mature strand are the same length. For example, if the mature strand is 21 nucleotides long, then the star strand will be 21 nucleotides in length also, with two extra bases appearing 5' of $S_1$ in the alignment above. In embodiments where the algorithm of Formula I is used and where the mature strand is a 21 nucleotide sequence, bases 2-19 of the mature strand (nucleotide 1 of the mature is preferably a U) are determined by the algorithm of Formula I, and bases 20 and 21 may be (but need not be) Gs to mimic the endogenous miR-196a-2 mature strand sequence. If bases 20-21 of the mature strand are GG, then bases at the opposite position on the star strand can be CC, UU, UC (as in the endogenous mature strand-star strand sequence), or CU (thus forming a base pair, either Watson-Crick or wobble). Alternatively, positions 20 and 21 can be GG and these nucleotides can be mismatched with nucleotides at opposing positions in the star strand (e.g. G-G mismatches or G-A mismatches). Alternatively positions 20 and 21 can consist of sequences that base pair with the target RNA. In this case the nucleotides on the opposing star strand can generate Watson-Crick pairings, wobble pairings, or mismatches.

Similarly, if the mature strand is 22 nucleotides long (as noted above, there is evidence to support the existence of both 21 nucleotide and 22 nucleotide endogenous mature strands for miR-196a-2), then the star strand will be 22 nucleotides in length also, with three extra bases appearing 5' of $S_1$ in the alignment above. In embodiments where the algorithm of Formula I is used and where the mature strand is a 22 nucleotide sequence, bases 2-19 of the mature strand (nucleotide 1 of the mature is preferably a U) are determined by the algorithm of Formula I, and bases 20, 21, and 22 may be (but need not be) Gs to mimic the endogenous miR-196a-2 mature strand sequence. If bases 20-22 of the mature strand are GGG, then bases at the opposite position on the star strand can be form either Watson-Crick base pairs or wobble pairs. For example, if bases 20-22 of the mature strand are GGG, then the star strand sequence opposite this sequence could be CUC which mimics the endogenous mature strand-star strand duplex at this position. Alternatively, positions 20, 21, and 22 can be GGG and these nucleotides can be mismatched with nucleotides at opposing positions in the star strand (e.g. G-G mismatches or G-A mismatches). Alternatively positions 20-22 can consist of sequences that base pair with the target RNA. In this case the nucleotides on the opposing star strand can generate Watson-Crick pairings, wobble pairings, or mismatches.

Formula I refers to the reverse complement of the target sequence nucleotide position preferences. As such, Formula I is applied, for example, by: (1) determining the sequence that is the reverse complement of a target RNA; and (2) applying the algorithm to this sequence to identify the 19 nucleotide sub-sequence(s) with a desirable score in the algorithm (e.g. with the highest, or one of the highest scores relative to other sub-sequences). The identified sequences are then introduced into a miR-196a-2 miRNA scaffold to yield non-naturally occurring miR-196a-2 miRNAs.

Formula I can also be expressed as a series of criteria, where each criterion represents the rank order preference for a base of the RC of the target sequence:
criterion 1: at position 1 of the RC of the target sequence, T is favored over C, and G and A are each disfavored
criterion 2: at position 5 of the RC of the target sequence, T is favored over each of G, C, and A
criterion 3: at position 6 of the RC of the target sequence, A is favored over each of G and C; and each of G and C is favored over T
criterion 4: at position 7 of the RC of the target sequence, A is favored over each of C and T; and each of C and T is favored over G
criterion 5: at position 8 of the RC of the target sequence, T is favored over each of A and G; and each of A and G is favored over C
criterion 6: at position 12 of the RC of the target sequence, T is favored over each of A and C; and each of A and C is favored over G
criteria 7: at position 13 of the RC of the target sequence, T is favored over each of A and G; and each of A and G is favored over C
criterion 8: at position 15 of the RC of the target sequence, T is favored over each of A and C; and each of A and C is favored over G
criterion 9: at position 16 of the RC of the target sequence, each of A, C, and T is favored over
criterion 10: at position 17 of the RC of the target sequence, each of A, C, and T is favored over G
criterion 11: at position 18 of the RC of the target sequence, T is favored over each of A and C; and each of A and C is favored over G
criterion 12: at position 19 of the RC of the target sequence, C is favored over T; T is favored over A; A is favored over G In some embodiments, one or more (or all) of the criteria are applied to identify mature strand sequences. For example, the criteria are applied by (1) determining the sequence that is the reverse complement of a target RNA; and (2) applying one or more of the criteria to identify a 19 nucleotide sub-sequence(s). The identified sequences are then introduced into a miR-196a-2 miRNA scaffold to yield non-naturally occurring miR-196a-2 miRNAs. In preferred embodiments, the mature position 1 is a T/U.

One skilled in the art will appreciate that Formula I can also be equivalently expressed so that it refers directly to target RNA nucleotide preferences ($R_1$-$R_{19}$ in table 1). This is done simply by replacing each nucleotide preference in Formula I with the opposite complementary nucleotide in the target RNA (see table 1). Once a desirable target RNA sequence is identified, its reverse complement (preferably with a T/U at position 1) is introduced into an miR-196a-2 miRNA scaffold where it forms the mature strand. Therefore if the original version of Formula I referred to a "G" at $M_2$, then the reformulated version would refer to a "C" at $R_{18}$.

Similarly, when Formula I is used to describe the target site, it can also be expressed as a series of criteria, where each criterion represents the rank order preference for a base of the target RNA (i.e. bases $R_1$-$R_{19}$ in the table above):
criterion 1: at $R_1$, G is favored over A, A is favored over U, and U is favored over C
criterion 2: at $R_2$, A is favored over each of U and G, and each of U and G is favored over C;
criterion 3: at $R_3$, each of U, G, and A is favored over C
criterion 4: at $R_4$, each of U, G, and A is favored over C
criterion 5: at $R_5$, A is favored over each of U and G, and each of U and G is favored over C
criterion 6: at $R_7$, A is favored over each of U and C, and each of U and C is favored over G
criterion 7: at $R_9$, A is favored over each of U and G, and each of U and G is favored over C
criterion 8: at $R_{12}$, A is favored over each of U and C, and each of U and C is favored over G
criterion 9: at $R_{13}$, U is favored over each of G and A, and each of G and A is favored over C
criterion 10: at $R_{14}$, U is favored over each of C and G, and each of C and G is favored over A;
criterion 11: at $R_{15}$, A is favored over each of C, G, and U;
criterion 12: at $R_{19}$, A is favored over G, and each of C and U are disfavored.

One or more (or all) of the criteria may be applied to determine a desirable target RNA sequence. For example, one or more of the criteria are applied to a target RNA sequence to identify a 19 nucleotide sub-sequence(s); the reverse complement of the identified sub-sequence (preferably with a "T" at position 1) is then introduced into a miR-196a-2 miRNA scaffold as a mature strand to yield non-naturally occurring miR-196a-2 miRNA. In preferred embodiments, at least criterion 12 is selected such that $R_{19}$ is A.

In another embodiment, the disclosure provides another algorithm for determining bases 1-21 (numbered in the 5' to 3' direction) of the mature strand (which may be a 21-25 nucleotide mature strand) of a highly functional non-naturally occurring miR-196a-2 miRNA, see Formula II below:

Formula II: for nucleotides 1-21 of a reverse complement of a target sequence.

Score=(−500)*$A1$+(43.75)*$T1$+(−21.25)*$C1$+
(−500)*$G1$+(−36.7)*$C3$+(−33.3)*$A5$+(50)*$T5$+
(−46.7)*$C5$+(37.5)*$A6$+(25)*$A7$+(29.2)*$T7$+(−41.25)*$G7$+(21.25)*$T8$+(−16.25)*$C8$+
(45.8)*$T12$+(−18.75)*$G12$+(58.3)*$T13$+
(−37.5)*$C13$+(−36.7)*$C14$+(21.25)*$T15$+
(−17.5)*$G15$+(−36.7)*$C16$+(−18.75)*$G16$+
(40)*$T17$+(−18.75)*$G17$+(16.25)*$T18$+
(−17.5)*$G18$+(−33.3)*$A19$+(21.25)*$T19$+
(28.75)*$C19$+(−35)*$G19$+(−23.3)*$C20$+
(50)*$T21$ where "A" represents an adenine, "G" represents a guanine, "T" represents a thymine, and "C" represents a cytosine. In addition, the number following the symbol for each base (e.g. A1) refers to the position of the base in the reverse complement of the target mRNA. As such the reverse complement nucleotide 1 in the algorithm is the complement of nucleotide 21 in the target mRNA (see FIG. 2). Table 2 below indicates the aligned nucleotide positions, where $M_1$-$M_{21}$ are nucleotides 1-21 of the mature strand; $R_1$-$R_{21}$ are nucleotides 1-21 of the target RNA, and nucleotides $S_1$-$S_{21}$ are nucleotides 1-21 of the star strand

TABLE 2

| 3' | $S_{21}$ | $S_{20}$ | $S_{19}$ | $S_{18}$ | $S_{17}$ | $S_{16}$ | $S_{15}$ | $S_{14}$ | $S_{13}$ | $S_{12}$ | $S_{11}$ | 5' |
|---|---|---|---|---|---|---|---|---|---|---|---|---|
| 5' | $M_1$ | $M_2$ | $M_3$ | $M_4$ | $M_5$ | $M_6$ | $M_7$ | $M_8$ | $M_9$ | $M_{10}$ | $M_{11}$ | 3' |
| 3' | $R_{21}$ | $R_{20}$ | $R_{19}$ | $R_{18}$ | $R_{17}$ | $R_{16}$ | $R_{15}$ | $R_{14}$ | $R_{13}$ | $R_{12}$ | $R_{11}$ | 5' |
| | 3' | $S_{10}$ | $S_9$ | $S_8$ | $S_7$ | $S_6$ | $S_5$ | $S_4$ | $S_3$ | $S_2$ | $S_1$ | 5' |
| | 5' | $M_{12}$ | $M_{13}$ | $M_{14}$ | $M_{15}$ | $M_{16}$ | $M_{17}$ | $M_{18}$ | $M_{19}$ | $M_{20}$ | $M_{21}$ | 3' |
| | 3' | $R_{10}$ | $R_9$ | $R_8$ | $R_7$ | $R_6$ | $R_5$ | $R_4$ | $R_3$ | $R_2$ | $R_1$ | 5' |

Note that if the mature strand is longer than 21 nucleotides (for example, 22 or 23 nucleotide in length), then the star strand will also include additional nucleotides at its 5' end such that the star strand and the mature strand are the same length. For example, if the mature strand is 22 nucleotides long (which may be the length of the endogenous miR-196a-2 mature strand), then the star strand will be 22 nucleotides in length also, with one extra bases appearing 5' of $S_1$ in the alignment above. In embodiments where the algorithm of Formula II is used and where the mature strand is a 22 nucleotide sequence, bases 2-21 of the mature strand sequence (nucleotide 1 of the mature is preferably a U) are determined by the algorithm of Formula II and bases 22 may be, for example, G (which is the same nucleotide in the endogenous 22 nucleotide mature strand of miR-196a-2). If base 22 of the mature strand is G, then the base at the opposing position on the star strand can be C (as in the endogenous miR-196a-2) or U (thus forming a base pair, either Watson-Crick or wobble). Alternatively, position 22 can be G and can be mismatched with the nucleotide a the opposing position in the star strand (e.g. a G-G mismatches or a G-A mismatch). Alternatively position 22 can be a nucleotide that base pairs with the target RNA. In this case the nucleotide on the opposing star strand can generate Watson-Crick pairings, wobble pairings, or mismatches.

As with Formula I, Formula II refers to the reverse complement of the target sequence nucleotide position preferences. As such, Formula II is applied, for example, by: (1) determining the sequence that is the reverse complement of a target RNA; and (2) applying the algorithm to this sequence to identify the 21 nucleotide sub-sequence(s) with a desirable scores in the algorithm (e.g. with the highest, or one of the highest scores relative to other sub-sequences). The identified sequences are then introduced into a miR-196a-2 miRNA scaffold to yield non-naturally occurring miR-196a-2 miRNAs.

Formula II can also be expressed as a series of criteria, where each criterion represents the rank order preference for a base of the reverse complement of the target sequence e.g:

criterion 1: at position 1 of the reverse complement of the target sequence, T>C, and each of A and G are disfavored criterion 2: at position 3 of the reverse complement of the target sequence, A, T, G>C criterion 3: at position 5 of the reverse complement of the target sequence, T>G>A>C criterion 4: at position 6 of the reverse complement of the target sequence, A>G, C, T criterion 5: at position 7 of the reverse complement of the target sequence, T>A>C>G criterion 6: at position 8 of the reverse complement of the target sequence, T>A, G>C criterion 7: at position 12 of the reverse complement of the target sequence, T>A, C>G criterion 8: at position 13 of the reverse complement of the target sequence, T>A, G>C criterion 9: at position 14 of the reverse complement of the target sequence, A, G, T>C criterion 10: position 15 of the reverse complement of the target sequence, T>A, C>G criterion 11: at position 16 of the reverse complement of the target sequence, A, T>G>C criterion 12: at position 17 of the reverse complement of the target sequence, T>A, C>G criterion 13: at position 18 of the reverse complement of the target sequence, T>A, C>G criterion 14: at position 19 of the reverse complement of the target sequence, C>T>A>G criterion 15: at position 20 of the reverse complement of the target sequence, A, G, T>C criterion 16: at position 21 of the reverse complement of the target sequence, T>A, G, C where > indicates that one base is preferred over another e.g. W>X, Y>Z indicates that W is favored over each of X and Y; and each of X and Y is favored over Z. In some embodiments, one or more (or all) of the criteria are applied to identify mature strand sequences.

For example, the criteria are applied by (1) determining the sequence that is the reverse complement of a target RNA; and (2) applying one or more of the criteria to identify a 21 nucleotide sub-sequence(s). The identified sequences are then introduced into a miR-196a-2 miRNA scaffold to yield non-naturally occurring miR-196a-2 miRNAs. In preferred embodiments, position 1 of the mature strand is a "T".

As with Formula I, Formula II can also be equivalently expressed so that it refers directly to target RNA nucleotide preferences ($R_1$-$R_{21}$ in Table 2). This is done simply by replacing each nucleotide preference in Formula II with the complementary nucleotide in the target RNA (see Table 2).

Similarly, Formula II can also be expressed as a series of criteria, where each criterion represents the rank order preference for a base of the target RNA (i.e. bases $R_1$-$R_{21}$ in the table above):

criterion 1: at $R_1$, A is favored over each of U, C, and G
criterion 2: at $R_2$, each of U, C, and A are favored over G;
criterion 3: at $R_3$, G is favored over A, A is favored over U, and U is favored over C;
criterion 4: at $R_4$, A is favored over each of U and G, and each of U and G is favored over C;
criterion 5: at $R_5$, A is favored over each of U and G, and each of U and G is favored over C;
criterion 6: at $R_6$, each of U and A is favored over C, and C is favored over G;
criterion 7: at $R_7$, is A is favored over each of U and G, and each of U and G is favored over C;
criterion 8: at $R_8$, each of U, C, and A is favored over G;
criterion 9: at $R_9$, A is favored over each of U and C, and each of U and C is favored over G;
criterion 10: at $R_{10}$, A is favored over each of U and G, and each of U and G is favored over C;
criterion 11: at $R_{14}$, A is favored over each of U and C, and each of U and C is favored over G;
criterion 12: at $R_{15}$, A is favored over U, U is favored over G, and G is favored over C;
criterion 13: at $R_{16}$, U is favored over each of C, G, and A;
criterion 14: at $R_{17}$, A is favored over C, C is favored over U, and U is favored over G;
criterion 15: at $R_{19}$, each of U, A, and C is favored over G;
criterion 16: at $R_{21}$, A is preferred over G, and each of U and C are disfavored One or more (or all) of the criteria may be applied to determine a desirable target sequence. For example, the criteria are applied by applying one or more of the criteria to a target RNA sequence to identify a nucleotide sub-sequence(s); the reverse complement of the identified sequence (preferably with a T/U at position 1) is then introduced into a miR-196a-2 miRNA scaffold as a mature strand to yield non-naturally occurring miR-196a-2 miRNA. Again, in preferred embodiments position 1 of the mature strand is a "T/U".

Additional weighted elements that focus on regiospecific factors, particularly overall GC content, GC content in the seed region, and the appearance of tetranucleotides, can be added to further enhance the functionality of Formulas I, II, or derivatives thereof. For example, these include any of the following elements in the mature strand:

a. −3* (# GCs)
b. −100 IF AT LEAST 1 "AAAA"
c. −100 IF AT LEAST 1 "TTTT"
d. −100 IF AT LEAST 1 "GGGG"
e. −100 IF AT LEAST 1 "CCCC"
f. −100 IF >4 GCs IN 2-8
g. −100 IF >10 GCs

Where:
"# of GCs" refers to the number of G and C nucleotides in the reverse complement of the target (or in the target RNA when Formula I or II is expressed as target RNA preferences)
"AAAA" refers to a tetranucleotide containing all As in the reverse complement of the target (equivalent to "UUUU" in the target RNA when Formula I or II is expressed as target RNA preferences)
"TTTT" refers to a tetranucleotide containing all Ts (equivalent to "AAAA" in the target RNA when Formula I or II is expressed as target RNA preferences)
"GGGG" refers to a tetranucleotide containing all Gs (equivalent to "CCCC" in the target RNA when Formula I or II is expressed as target RNA preferences)
"CCCC" refers to a tetranucleotide containing all Cs (equivalent to "GGGG" in the target RNA when Formula I or II is expressed as target RNA preferences)
">4 GCs in 2-8 of mature" refers to more than four G and/or C nucleotides anywhere in positions 2-8 of the mature strand (i.e. the seed region), (equivalent to more than four G and/or C nucleotides anywhere in positions $R_{14}$-$R_{20}$ when Formula II is expressed as RNA target preferences, or in positions $R_{12}$-$R_{18}$ when Formula I is expressed as RNA target preferences).
">10 GCs" refers to more than ten G and/or C nucleotides anywhere in the reverse complement of the target (equivalent to more than ten G and/or C nucleotides anywhere in the target RNA when Formula I or II is expressed as RNA target preferences).

Similarly, when Formula I and Formula II are expressed as a series of criteria (as described above), these additional weighted elements may also be expressed as additional criteria. For example, when Formula I or Formula II is expressed as a series of criteria, the additional weighted elements may be expressed as the following additional criteria, one or more (or all) of which may be applied to select desirable sequences:

A) the reverse complement of the target does not include a tetranucleotide sequence selected from the group consisting of AAAA, UUUU, GGGG, and CCCC (or, equivalently, the target RNA subsequence does not include AAAA, UUUU, GGGG, or CCCC);
B) the reverse complement of the target has a total G+C content of not more than 10 (or, equivalently, the target RNA subsequences does not have a total G+C content of more than 10)
C) the mature strand has a G+C content of not more than 4 in the seed region (or, equivalently, the bases of the target RNA subsequence that are opposite the seed region of the mature strand has a G+C content of not more than 4)

It should be noted that when describing the mature strand, the nucleotide U can be used to describe the RNA sequence, or the nucleotide T can be used to describe the cDNA sequence for the RNA.

Additional weighted factors that focus on eliminating target sequences that can have secondary structures (e.g. hairpins) can also be added to selection algorithms.

Furthermore, any of the methods of selecting sequences can further comprise selecting either for or against sequences that contain motifs that induce cellular stress. Such motifs include, for example, toxicity motifs (see US2005/0203043, published Sep. 15, 2005). The above-described algorithms may be used with or without a computer program that allows for the inputting of the sequence of the target and automatically outputs the optimal targeting sequences. The computer program may, for example, be accessible from a local terminal or personal computer, over an internal network or over the Internet.

Furthermore, any of the methods of selecting sequences can further comprise selecting for or against targeting sequences that have particular seed region (positions 2-7 or 2-8 of the mature strand) sequences. In one non-limiting example, targeting sequences that have seeds that show complete identity to one of the seeds of one or more endogenously expressed microRNAs can be eliminated. In another example, seeds that have medium or high seed complement frequencies can be eliminated. Full descriptions of the importance of seeds having medium or high seed complement frequencies can be found in U.S. Ser. No. 11/724,346, filed Mar. 15, 2007.

Once optimal mature strand sequences have been obtained, they are introduced in miR-196a-2 scaffolds as described above. The star strand is (for the most part) the reverse complement of the mature strand, but preferably has some alterations to create local structure to mimic the structure of the endogenous mature strand-star strand of endogenous miR-196a-2. Star strand attributes, for example, may include one or more of the following shown in FIG. 3 and described in detail below:

1. When position 1 of the mature strand is a U (which, as discussed above, is preferable but not mandatory), the star strand position opposite is preferably a G to ensure it will always wobble pair
2. If position 5 of the mature strand is G or T (U), then the star strand position opposite it is preferably altered to be T(U) or G (respectively) to create a wobble pair.
3. If the mature strand has something other than G or T at position 5, then the star strand position opposite is designed to generate a standard Watson-Crick pair.
4. A mismatch is preferably created between position 12 of the mature strand and the opposite position of the star strand. This can be achieved by the relevant position of the star strand having the same base as position 12 of the mature strand.
5. If the mature strand is 18 nucleotides or longer in length, then same criteria that are applied to positions 5 of the mature strand and the opposite position of the star strand are similarly applied to positions 18 of the mature strand and the opposite position of the star strand. Specifically, if position 18 of the mature strand is G or T (U), then the star strand position opposite it is altered to be T(U) or G, respectively, to create a wobble pair. If the mature strand has something other than G or T at position 18, then the star strand position opposite this position is designed to generate a standard Watson-Crick pair
6. If the mature strand is 19 nucleotides or longer in length, then the same criteria that are applied to positions 5 of the mature strand and the opposite position of the star strand are similarly applied to positions 19 of the mature strand and the opposite position of the star strand. Specifically, if position 19 of the mature strand is G or T (U), then the star strand position opposite it is altered to be T(U) or G (respectively) to create a wobble pair. If the mature strand has something other than G or T(U) at position 19, then the star strand is designed to generate a standard Watson-Crick pair.
7. If the mature strand is 21 nucleotides or longer in length, then the same criteria that are applied to positions 5 of the mature strand and the opposite position of the star strand are similarly applied to positions 21 of the mature strand and the opposite position of the star strand. Specifically, if position 21 of the mature strand is G or T (U), then the star strand position opposite it is altered to be T(U) or G (respectively) to create a wobble pair. If the mature strand has something other than G or T(U) at position 21, then the star strand is designed to generate a standard Watson-Crick pair.

The star strand positions opposite the referenced mature strand positions are provided in Tables 1-2 above. One or more of these additional criteria can be combined with Formulas I or II to enhance the performance of the targeting sequence inserted into the e.g. miR-196a-2, scaffold.

It is important to note that in many cases, the order at which some of the steps described above are performed is not critical. Thus, for instance, sequences can be scored by the algorithm(s) and subsequently, high scoring sequences can be screened to eliminate seeds with undesirable properties. Alternatively, a list of potential sequences can be generated and screened to eliminate undesirable seeds, and the remaining sequences can then be evaluated by the algorithm(s) to identify functional targets.

Each formula produces a different range of possible raw scores. In order to make scores from different formulas more comparable and easier to evaluate, mathematical methods can be employed to normalize raw scores derived from each formula. Different normalization equations can exist for each formula. Preferably, the normalization equation is chosen to produce scores in the 0-100 range for all (or almost all) design sequences. When planning to conduct gene silencing, one should choose sequences by comparing the raw scores generated by a formula, or comparing the normalized scores between formulas. In general a higher scored sequence should be used.

Embodiments where the Target Sequence of the Target RNA is Selected without Using an Algorithm The embodiments described immediately above use an algorithm to, for example, scan a target RNA for a subsequence that meets various criteria that are specific to a particular miRNA scaffold. A mature strand that has full reverse complementarity to the sequence identified by the algorithm is then introduced into the scaffold. The algorithms thus select those sequences that are likely to be the most functional in a particular scaffold. In another series of embodiments, the target RNA subsequence is chosen without using such an algorithm. In one such embodiment, a mature strand is designed that is the full reverse complement of the chosen target RNA subsequence. This mature strand is then inserted into a miRNA scaffold to form a non-naturally occurring miRNA. It is believed (without being limited by theory or mechanism) that expression of a mature strand that is the full reverse complement of a target RNA sequence will lead to the target RNA being cleaved by RISC.

In another embodiment, a mature strand is designed that is only a partial reverse complement of the chosen target RNA subsequence. This mature strand is then inserted into a miRNA scaffold to form a non-naturally occurring miRNA. Preferably, the seed region of such a mature strand (positions 2-7) is fully complementary to one or more regions of the target RNA subsequence(s), but the remainder of the mature strand includes one or more bases that are not complementary to the target RNA subsequence. Without being limited by theory or mechanism, it is believed that when such a mature strand anneals to its target RNA, translational attenuation rather than cleavage occurs.

Previous studies have demonstrated that complementarity between the seed region of the mature strand and region(s) the target mRNA(s) (preferably the 3' UTR) is desired to effectively modulate gene expression by the translation attenuation pathway. One or more additional parameters that might also be considered include 1) selecting target RNA sequences where a particular short sequence (e.g. 6 nucleotides) is repeated two or more times, preferably about 10-50 nucleotides apart and preferably in the 3' UTR of the target mRNA. This allows the design of a mature strand sequence with a seed region (positions 2-7) that has two or more complements in the target mRNA, (i.e. a single mature strand can target two or more sites of a single 3' UTR); 2) selecting target RNA sequences in the target gene that are operationally linked with additional sites that enhance gene modulation by RNAi mediated translation attenuation (e.g., AU rich sequences); and 3) selecting a target RNA sequence that can form an AU basepair with position 1 of a mature strand and a Watson-Crick basepair with position of the mature strand. These and other design considerations can greatly facilitate gene modulation by the translation attenuation mechanism.

Expression and Use of Non-Naturally Occurring miRNAs

Non-naturally occurring miRNAs of the disclosure (including those where the mature strand is rationally designed according to Formula I or Formula II, also including those where the mature strand sequence is not selected using Formula I or Formula II, and also including shMIMICs) can be expressed in a variety of vector construct systems including plasmids and viral vectors that maintain sequences either epigenetically or insert into the host genome. By way of example, a 21 nucleotide mature strand sequence where (A) bases 2-19 are determined by Formula I (position $M_1$ of the mature strand is preferably a T/U) or are derived from the mature strand sequence of another miR other than miR-196a-2; and (B) bases 20-21 are each G (which is the endogenous sequence for the 21 nucleotide mature strand of miR-196a-2) may be introduced into a miR-196a-2 miRNA scaffold, along with a 21 nucleotide star strand (TC-$S_1$-$S_{19}$), to yield a vector insert having the following sequence:

```
                                          SEQ ID NO: 24
5' TGATCTGTGGCT + [M1-M19-GG] +

GATTGAGTTTTGAAC + [TC-S1-S19] +

AGTTACATCAGTCGGTTTTCG 3'.
```

The reverse complement of this sequence can be annealed, cloned into the appropriate vectors, and expressed to lower the functional capacity of the target RNA e.g. to provide long term silencing of a gene of interest. Note that as there is evidence to support the existence of both a 21 nucleotide and 22 nucleotide endogenous miR-196a-2 mature strand, then it is possible that the aforementioned sequence, when expressed in cells, will be processed to yield a 21 nucleotide mature strand ($M_1$-$M_{19}$-GG) and/or a 22 nucleotide mature strand ($M_1$-$M_{19}$-GGG). Thus the G that is underlined in the aforementioned sequence may be either be part of the miR-196a-2 scaffold or part of the mature strand.

Preferred viral vectors include but are not limited to lentiviral vectors (e.g. HIV, FIV), retroviral vectors, adenoviral vectors, adeno-associated virus, and rabies vectors. In all of these cases, non-naturally occurring miRNAs can be transcribed as non-coding RNAs (e.g. from a pol III promoter) or can be associated with a messenger RNA transcribed by a pol II promoter. In one embodiment, the promoter is a tissue-specific promoter. In another embodiment, the promoter is a regulatable promoter (e.g. a tet promoter or a Reoswitch™). The promoter sequence can be derived from the host being targeted or can be taken from the genome(s) of another organism. Thus for instance, the promoter can be a viral promoter such as a CMV, HIV, FIV, or RSV promoter sequence (such as a promoter found in a Long Terminal Repeat (LTR)). The sequences encoding the non-naturally occurring miRNA can be positioned in a variety of positions with regard to other elements associated with the vector system. For instance, the sequences encoding the non-naturally occurring miRNA can be associated with a gene that is expressed from a pol II promoter and inserted in the 5' and/or 3' UTR of a gene, or in one or more introns of a gene. In one preferred embodiment, the sequence encoding a non-naturally occurring miRNA is associated with a marker and/or reporter gene, including but not limited to a fluorescent reporter (e.g. GFP, YFP, RFP, and BFP), an enzymatic reporter (e.g. luciferase) or a drug resistant marker (e.g. puromycin) or other genes whose expression does not significantly alter the physiological properties of the cell. In another instance, expression of the non-naturally occurring miRNA can be unrelated to the expression of a gene (i.e. transcribed as a non-coding sequence from a pol III promoter). In some instances, the regulation can incorporate multiple elements described above, for instance combining a regulatable promoter (e.g. $P_{tet}$) with a tissue specific promoter to provide a tissue-specific regulatable expression system.

The number of non-naturally occurring miRNAs associated with a particular vector construct can also vary. In one embodiment, a single non-naturally occurring miRNA is expressed from a vector. In another embodiment, two or more non-naturally occurring miRNAs (i.e. a pool) are expressed from a vector. Where two or more non-naturally occurring miRNAs are expressed, they need not be related and can be associated with a single transcript (e.g. two non-naturally occurring miRNAs present in the same 3' UTR) or two separate transcripts (i.e., two non-naturally occurring miRNAs can be associated with and expressed from two unrelated transcripts). In cases where multiple non-naturally occurring miRNAs are expressed from a single vector, the non-naturally occurring miRNAs can be identical (e.g. two copies of a non-naturally occurring miR 196a-2 miRNA) or dissimilar (e.g. one copy of a non-naturally occurring miR 196a-2 miRNA and one copy of a non-naturally occurring miR-204 miRNA; or two shMIMICS, both with the same scaffold but with different mature stands; or two shMIMICS with the same mature strands but different scaffolds; or a shMIMIC and another non-naturally occurring miRNA with either a randomly selected mature strand or a rationally selected mature strand etc). Furthermore, the non-naturally occurring miRNAs can target a single target RNA (thus effectively having a pool of sequences targeting one gene product) or can target multiple genes (i.e. multigene targeting). Both pooling and multigene targeting can be achieved with the non-naturally occurring miRNAs of the disclosure by another means. Specifically, multiple non-naturally occurring miRNAs targeting one or more target RNAs can be inserted into multiple vectors and then combined (mixed) and 1) transfected, or 2) transduced into the cell type of interest.

Vector constructs that encode non-naturally occurring miRNAs may be introduced into a cell by any method that is now known or that comes to be known and that from reading this disclosure, persons skilled in the art would determine would be useful in connection with the present disclosure. These methods include, but are not limited to, any manner of transfection, such as for example transfection employing DEAE-Dextran, calcium phosphate, cationic lipids/liposomes, micelles, manipulation of pressure, microinjection, electroporation, immunoporation, use of viral vectors, cosmids, bacteriophages, cell fusions, and coupling to specific conjugates or ligands.

In cases where the a non-naturally occurring miRNA is delivered to a cell using a virus, the vector construct can be maintained in the cytoplasm or can be integrated into and expressed from the host genome (e.g. lentiviral). Such vectors frequently include sequences necessary for packaging such viruses, but lack functions that are provided by "helper" plasmids to avoid the generation of infectious particles. Furthermore, when viral systems are being used, the level of expression of the construct can be manipulated by altering the promoter driving the expression of the construct (thus altering the level of expression of the construct). Alternatively, the expression levels can be altered by adjusting the multiplicity of infection (MOI), effectively altering the number of copies of the expression cassette that are placed in each cell.

According to another embodiment, the present disclosure provides a kit comprised of at least one non-naturally occurring miRNA.

According to another embodiment, the present disclosure provides a kit comprised of at least one vector construct that encodes a non-naturally occurring miRNA.

According to another embodiment, the present disclosure provides a kit comprised of at least one miRNA scaffold. The miRNA scaffold can then be used to generate a plurality of different non-naturally occurring miRNAs (including shMIMICS) by cloning mature strand and star strand sequences into the miRNA scaffold, and then expressing the resulting non-naturally occurring miRNAs in a cell.

The miRNA scaffolds, non-naturally occurring miRNAs, and methods of the disclosure may be used in a diverse set of applications, including but not limited to basic research, drug discovery and development, diagnostics, and therapeutics. In each case, the non-naturally occurring miRNA produced by introducing a mature strand sequence into a miRNA scaffold is used to lower the functional capacity of a target RNA such as an mRNA produced by a gene of interest. In research settings, the compositions and methods of the disclosure may be used to validate whether a gene product is a target for drug discovery or development.

Because the ability of the mature strand sequences embedded in the non-naturally occurring miRNA of the disclosure to function in the RNAi pathway is dependent on the sequence of the target RNA (e.g., an mRNA produced by a particular gene) and not the species into which it is introduced, the methods and compositions of the disclosure may be used to target genes across a broad range of species, including but not limited to all mammalian species, such as humans, dogs, horses, cats, cows, mice, hamsters, chimpanzees and gorillas, as well as other species and organisms such as bacteria, viruses, insects, plants and worms.

The methods and compositions of the disclosure are also applicable for use for silencing a broad range of genes, including but not limited to the roughly 45,000 genes of a human genome, and has particular relevance in cases where those genes are associated with diseases such as diabetes, Alzheimer's, cancer, as well as all genes in the genomes of the aforementioned organisms.

In yet another application, non-naturally occurring miRNAs directed against a particular family of genes (e.g., kinases), genes associated with a particular pathway(s) (e.g., cell cycle regulation), or entire genomes (e.g., the human, rat, mouse, C. elegans, or Drosophila genome) are provided. Knockdown of each gene of the collection with non-naturally occurring miRNAs that comprise mature strand sequences at least partially complementary to an RNA product of the genes would enable researchers to quickly assess the contribution of each member of a family of genes, or each member of a pathway, or each gene in a genome, to a particular biological function.

The methods and compositions of the disclosure may be employed in RNA interference applications that require induction of transient or permanent states of disease or disorder in an organism by, for example, attenuating the activity of a target RNA of interest believed to be a cause or factor in the disease or disorder of interest. Increased activity of the target RNA of interest may render the disease or disorder worse, or tend to ameliorate or to cure the disease or disorder of interest, as the case may be. Likewise, decreased activity of the target nucleic acid of interest may cause the disease or disorder, render it worse, or tend to ameliorate or cure it, as the case may be. Target RNA of interest can comprise genomic or chromosomal nucleic acids or extrachromosomal nucleic acids, such as viral nucleic acids.

Still further, the methods and compositions of the disclosure may be used in RNA interference applications, such as prophylactics, and therapeutics. For these applications, an organism suspected of having a disease or disorder that is amenable to modulation by manipulation of a particular target RNA of interest is treated by administering targeting sequences embedded in preferred scaffold expression systems. Results of the treatment may be ameliorative, palliative, prophylactic, and/or diagnostic of a particular disease or disorder. Preferably, the targeting sequence is administered in a pharmaceutically acceptable manner with a pharmaceutically acceptable carrier, diluent, or delivery system (e.g. a virus).

Further, the mature non-naturally occurring miRNAs of the disclosure can be administered by a range of delivery routes including intravenous, intramuscular, dermal, subdermal, cutaneous, subcutaneous, intranasal, oral, rectal, by eye drops, by tissue implantation of a device that releases the agent at an advantageous location, such as near an organ or tissue or cell type harboring a target nucleic acid of interest.

Further, the disclosure discloses the use of a non-naturally miRNA in the manufacture of a medicament for the treatment of a disease characterized by the inappropriate expression of a gene wherein the gene is targeted by the non-naturally occurring miRNA.

The illustrative preferred embodiments of the present invention are explained in the drawings and described in detail, with varying modifications and alternative embodiments being taught. While the invention has been so shown, described and illustrated, it should be understood by those skilled in the art that equivalent changes in form and detail may be made therein without departing from the true spirit and scope of the invention, and that the scope of the invention is to be limited only to the claims except as precluded by the prior art. Moreover, the invention as disclosed herein, may be suitably practiced in the absence of the specific elements which are disclosed herein.

All references cited in the present application are incorporated in their entirety herein by reference to the extent not inconsistent herewith.

The following examples are for illustrative purposes only and are not intended to limit the scope of the invention.

EXAMPLES

The following system of nomenclature was used to compare and report siRNA-silencing functionality: "F" followed by the degree of minimal knockdown. For example, F50 signifies at least 50% knockdown, F80 means at least 80% knockdown, and so forth. For this study, all sub-F50 RNAs were considered nonfunctional.

General Techniques

Total genomic DNA extraction: Total HeLa genomic DNA was extracted using a DNeasy Genomic DNA isolation kit (Qiagen). Overall integrity of the DNA was verified on a 0.8% agarose gel stained with Ethidium Bromide.

PCR Amplification of miRNAs from Genomic DNA:

PCR was used to amplify various miRNAs for testing in the dual luciferase system. Natural miRNAs were amplified from 10-100 ng HeLa genomic DNA with Qiagen Taq PCR Master Mix (Cat No 201443) and 10 μM of each primer. The PCR parameters were: 4 min at 94° C. for initial denaturation, 15 seconds at 94° C., 30 seconds at 50-60° C., and 45 seconds at 72° C. for 30 cycles, 2 min at 72° C. for final extension. Sequences used for amplification are provided in Table 3 below.

psiCheck Dual-Luc Reporter Constructs:

The dual-luciferase plasmid, psiCHECK™-2 Vector, containing both the humanized firefly luciferase gene (hluc) and the humanized *Renilla* luciferase gene (hRluc), each with its own promoter and poly(A)-addition sites, was obtained from Promega (Cat.# C8021). Reverse complement target sequences were inserted between the XhoI-Not I restriction sites in the multiple cloning site in the 3' UTR of the hRluc gene. Insert sequences were ordered from Operon to make an

TABLE 3

SpeI and BglII represent restriction sites that were incorporated into the primer sequences. "For" = forward primer. "Rev" = reverse primer. All sequences provided in 5' → 3' orientation.

| Primer | Sequence of Primer, 5' → 3' | SEQ ID NO: |
|---|---|---|
| SpeImiR338-For | TCATACTAGTGAGACAGACCCTGCTTCGAAGGACC | 26 |
| BglIImiR338-Rev | TCATAGATCTTGTCCCTCCCCACATAAAACCCATG | 27 |
| SpeImiR30c-1-For | TCATACTAGTTTTTACTCAGCCAGCCCAAGTGGTTCTGTG | 28 |
| BglIImiR30c-1-Rev | TCATAGATCTACATCTGGTTCTGGTTGTACTTAGCCAC | 29 |
| SpeImiR-26b-For | TCATACTAGTTGGATACATGTGGAATGTCAGAGGC | 30 |
| BglIImiR-26b-Rev | TCATAGATCTTGACCACTGCTGGGGAAACTGTACC | 31 |
| SpeImiR196a-2-For | TCATACTAGTTCAGACCCCTTACCCACCCAGCAACC | 32 |
| BglIImiR196a-2-Rev | TCATAGATCTAGAGGACGGCATAAAGCAGGGTTCTCCAG | 33 |
| SpeImiR196a-1-For | TCATACTAGTTCCGATGTGTTGTTTAGTAGCAACTGGG | 34 |
| BglIImiR196a-1-Rev | TCATAGATCTGACACTTCCCAGATCTCTTCTCTGG | 35 |
| SpeImiR30a-For | TCATACTAGTCGGTGATGAATAATAGACATCCATGAGCC | 36 |
| BglIImiR30a-Rev | TCATAGATCTACCTCCTCAATGCCCTGCTGAAGC | 37 |
| SpeImiR126-For | TCATACTAGTGGCACTGGAATCTGGGCGGAAG | 38 |
| BglIImiR126-Rev | TCATAGATCTAGAAGACTCAGGCCCAGGCCTCTG | 39 |
| SpeImiR-204-For | TCATACTAGTTGAGGGTGGAGGCAAGCAGAGGACC | 40 |
| BglIImiR-204-Rev | TCATAGATCTTTGGACCCAGAACTATTAGTCTTTGAG | 41 |
| SpeImiR486-For | TCATACTAGTGCGGGCCCTGATTTTTGCCGAATGC | 42 |
| BglIImiR486-Rev | TCATAGATCTAGCATGGGCAGTGTGGCCACAG | 43 |
| SpeImiR135a-2-For | TCATACTAGTAAATCTTGTTAATTCGTGATGTCACAATTC | 44 |
| BglIImiR135a-2-Rev | TCATAGATCTCACCTAGATTTCTCAGCTGTCAAATC | 45 |
| SpeImiR374-For | TCATACTAGTCAATTCCGTCTATGGCCACGGGTTAGG | 46 |
| BglIImiR374-Rev | TCATAGATCTTGTGGAGCTCACTTTAGCAGGCACAC | 47 |
| SpeImiR526a-1-For | TCATACTAGTAATGTAAGGTATGTGTAGTAGGCAATGC | 48 |
| BglIImiR526a-1-Rev | TCATAGATCTAGTTCCTGATACTGAGCTCCAGCCAG | 49 |

Two of the primer sets (for miR 338 and miR 135a-2) failed to amplify the respective sites. For the remaining scaffolds, the PCR product was gel-purified, treated with SpeI/BglII (NEB) and cloned into the MCS of a highly modified pCMV-Tag4 with GFP containing an artificial intron. Successful cloning was confirmed by sequencing. As a result of these procedures, the miRNAs are localized as within an artificial intron downstream of the ATG start site of GFP. (See FIG. 4).

insert compatible with the restriction sites. Firefly and *Renilla* luciferase activities were measured using the Dual-Glo™ Luciferase Assay System (Promega, Cat.#E2980) according to manufacturer's instructions with slight modification. When lysing cells, growth media was aspirated from the cells prior to adding 50 uL of firefly luciferase substrate and 50 uL *Renilla* luciferase substrate.

Cell viability was determined on a duplicate plate using the AlamarBlue® assay (BioSource Intl, Inc). Cell viabilities for control and experimentally treated cells were always within 15%.

For experiments requiring the quantitative determination of mRNA, cells were lysed in 1× lysis mixture and mRNA quantitation was performed by the branched DNA (bDNA) assay (QuantiGene® Screen Kit, Cat.# QG-000-050, Panomics). Branched DNA probes for targeted genes were designed by Panomics and in-house.

The Luciferase, alamarBlue and bDNA assays were all scanned with a Wallac Victor 1420 multilabel counter (Perkin Elmer) using programs as recommended by the manufacturers.

Cell Culture and Transfection:

One day prior to transfection, HeLacells were plated in a 96-well plate at cell density of at about 10,000 cells per well in Dulbecco's modified Eagle medium (DMEM) supplemented with 10% fetal bovine serum (FBS) without antibiotics. On the day of transfection, the appropriate mixtures were prepared (e.g. psiCheck dual luciferase plasmid containing the appropriate target sequences; plasmids (control and experimental) expressing the scaffold construct; siRNAs (100 nM) targeting the target sequence; Lipid delivery reagents (e.g. Lipofectamine 2000)). The mixtures were then introduced into cells using art-recognized transfection conditions.

Experimental Design and Data Analysis

All treatments were run in triplicate. To account for non-specific effects on reporter plasmids, experimental results are expressed as a normalized ratio $(Rluc/Fluc)_{norm}$: the ratio of Renilla luciferase expression to firefly luciferase expression for a given miRNA reporter plasmid $(Rluc/Fluc)_{miRNA}$ divided by the $(Rluc/Fluc)_{control}$ for a non-targeting sequence co-transfected with the reporter plasmid. The maximum values obtained from the reporter plasmid vary due to sequence; ideally values around 1 indicate low miRNA function, while values close to zero indicate high miRNA function. Data are reported as the average of the three wells and the error bars are the standard deviation of the three $(Rluc/Fluc)_{miRNA}$ ratios from the experimental treatment, scaled by the normalizing factor (the average of $(Rluc/Fluc)_{control}$). We recognize that ratios do not follow a normal distribution, but believe that the standard deviation values give a good sense of the variability of the data.

Example 1

Identification of High Performance miRNA Scaffolds

Figure 4F:
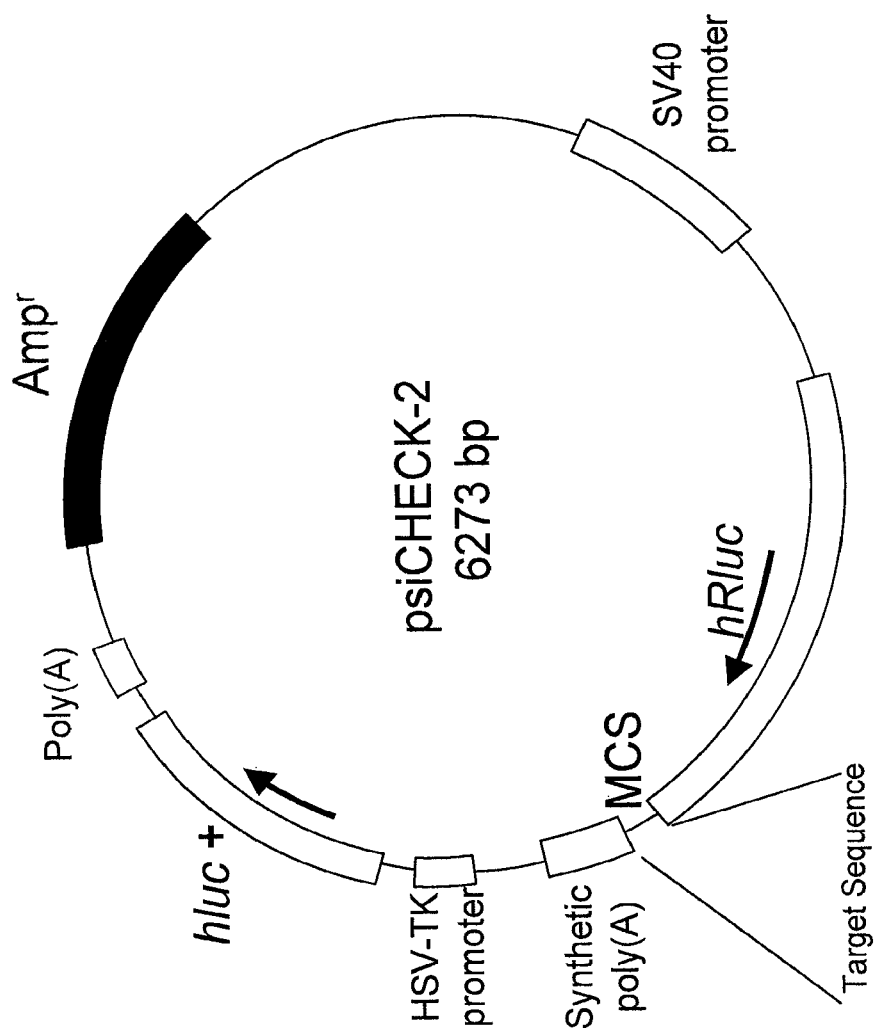

To identify highly functional miRNA scaffolds, ten separate miRNAs (including miR-126, 204, -196a2, -30c-1, -26b, -30a, -374, -196a1, -526, and -486) were PCR amplified from genomic DNA, and cloned into the SpeI/BglII sites of the artificial intron of GFP (see FIG. 4A-E). In parallel, dual-luciferase reporter plasmids containing the appropriate (reverse complement) target site in the 3' UTR of hRluc were constructed (FIG. 4F and Table 4). Plasmids encoding both constructs (both the artificial miRNA expression vector and the dual-luciferase reporter vector) were co-transfected into HeLa cells (10K cells per well in a 96-well plate) using Lipofectamine 2000 (Invitrogen, 0.2 μl per well) by standard forward transfection techniques, and assessed 48 hours later to determine the level of knockdown of the luciferase reporter.

Figure 5:
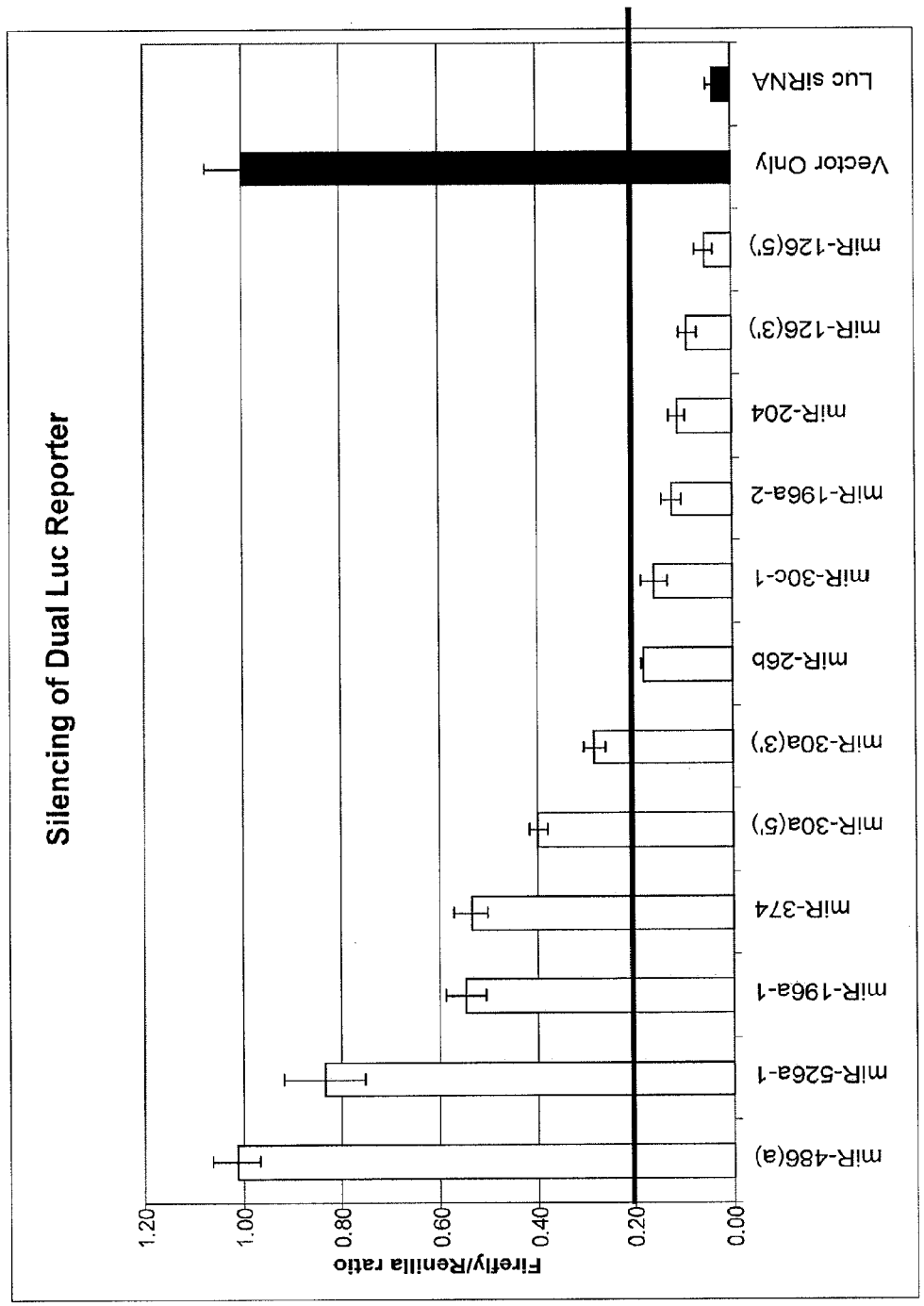
FIG. 5: Screening of Ten Distinct miRNA Scaffolds. A screen of multiple miRNA scaffolds using the dual luciferase reporter construct identified three miRNAs (miR-204, miR-26b, and miR-196a-2) that exhibited high activity in the reporter assay. Horizontal line represents 80% knockdown.

Results of these studies are presented in FIG. 5 and demonstrate that some miRNA scaffolds are more functional than others. Half of the constructs were eliminated from further study due to their inability to significantly silence the reporter construct (see miR-30a, -374, -196a1, -526, and -486, all showed less than 80% silencing of the reporter construct). In addition, further studies of miR-126 found that both strands of the hairpin (the mature and the star strand, referred to as the 5' and 3' strands respectively) were functional. Although having both star strand and the mature strand activity may be desirable in some applications (for example, to silence two different target genes), further studies of this construct were canceled. The three remaining miR scaffolds (-204, -26b, and -196a2) were identified as being highly functional, providing >80% silencing of the dual luciferase reporter construct. Interestingly, miR-196a-1, which has the same mature sequence as miR-196a-2 was identified as one of the less optimal scaffolds, suggesting that the sequence that surrounds the mature miR sequence may play an important role in Drosha/Dicer processing and that these effects may have a significant impact on miR functionality.

Example 2

Modifying miR Scaffold Sequences to Enable Cloning of Foreign Sequences

A key attribute of a miRNA scaffold for delivery of targeting sequences is the ability to introduce (clone) sequences into the scaffold and retain functionality. To achieve this, the three top performing scaffolds identified in Example 1 (miR-26b, -196a2, and -204) were modified to incorporate restriction sites into the constructs using standard molecular biology techniques. Subsequently, each construct was tested using the appropriate dual luciferase reporter construct containing the reverse complement to the mature targeting strand, to determine whether the changes altered either mature or star strand activity. For miR-26b and miR-204, nucleotide changes were made to introduce a BlpI and SacI restriction site into the construct (see FIGS. 6 A,B, top). For miR-196a-2, a natural BlpI site was already present in the construct, and therefore second restriction sites (including SacI, ScaI, and XbaI) were tested in combination (FIG. 6C, top and bottom).

Figure 6A:
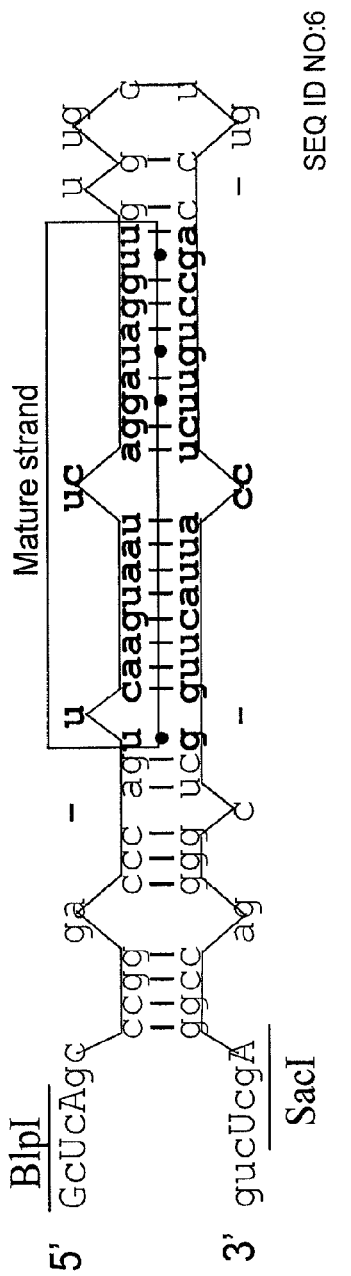
FIG. 6: Diagram of the Changes Placed in the miRNA scaffolds. Wobble base pairs are indicated by •. (A) example of a miR-26b construct. Top: Box indicates position of the mature strand sequence (which is shown here as the endogenous mature strand sequence). Nucleotides in upper case format are substitutions that introduce BlpI and SacI restriction sites. Bottom: bar graph shows the effects of incorporating restriction sites on mature and star strand functionality. (B) example of a miR-204 construct. Top: box indicates position of the mature strand sequence (which is shown here as the endogenous mature strand sequence). Nucleotides in upper case format are substitutions that introduce BlpI and SacI restriction sites. Bottom: bar graph demonstrates the effects of incorporating restriction sites on mature and star strand functionality. (C) examples of miR-196a-2 constructs. Box indicates position of the mature strand sequence which is shown here as the endogenous 21 nucleotide mature strand sequence. Note, however, that endogenous mature strand sequence of miR-196a-2 may actually be 22 nucleotides in length, and would thus extend one nucleotide (the g nucleotide indicated by *) further at the 3' end than the sequence indicated in the box. Thus, the g indicated by the * may either be part of the mature strand or part of the scaffold (and the opposite nucleotide c may be part of the star strand or part of the scaffold) depending on how the scaffold is processed by Drosha and/or Dicer. BlpI site is a natural component of the scaffold. Nucleotides in upper case format are substitutions that introduce XbaI, ScaI, and SacI restriction sites. (D) bar graph demonstrates the effects of incorporating restriction sites on mature and star strand functionality. ScaI=mismatches in the scaffold structure, ScaI+, base pair changes have been introduced to eliminate mismatches; XbaI=introduces mismatches in the structure; XbaI+=base pair changes have been introduced to eliminate mismatches. All experiments associated with assessing activity of modified constructs were performed using the dual luciferase reporter constructs. (E) Examples of the stem-loop regions of miR-196a-2 and miR-204 scaffolds (M=mature strand, S=star strand). Note that the g indicated by * in the miR-196a-2 example may also be considered to be part of the mature strand sequence (F) Example of a miR-204 scaffold. The site of mature strand and the star strand insertion is depicted schematically. Nucleotide substitutions (relative to endogenous miR-204) are indicated by use of upper case format. (G) Examples of miR-196a-2 scaffolds. The site of mature strand and the star strand insertion is depicted schematically. Nucleotide substitutions (relative to endogenous miR-196a-2) are indicated by use of upper case format. Note that the nucleotide g indicated by * may also be considered to be part of the mature strand sequence (and thus the opposite position c may also be considered to be part of the star strand sequence).
Figure 6A:
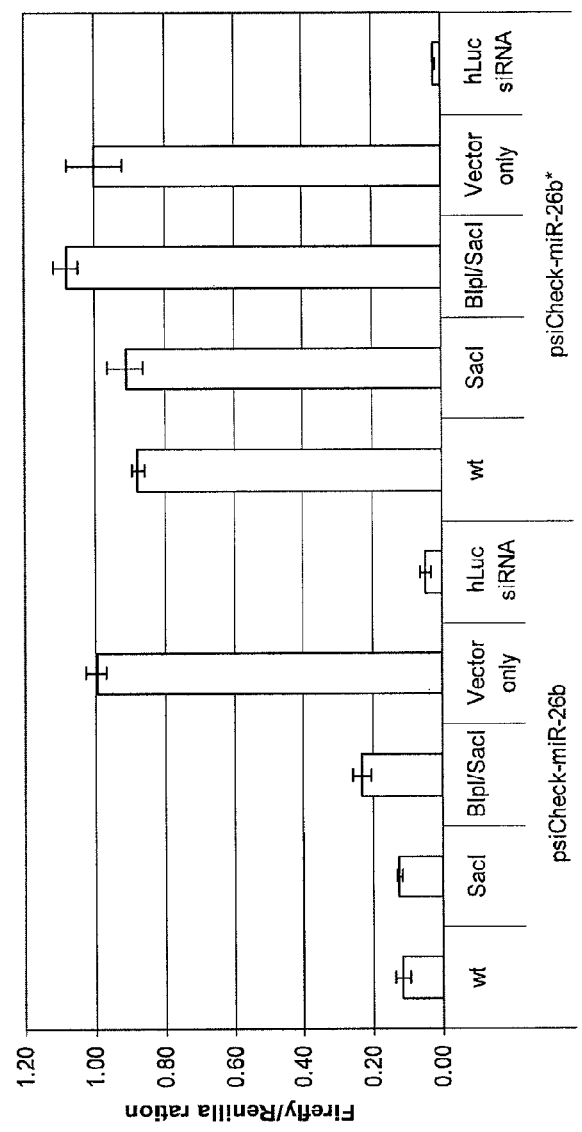

For miR-26b, incorporation of the Sac1 site had little or no effect on overall functionality of the mature strand (FIG. 6A, bottom, ~85-90% functionality). Further modification with the additional Blp1 site (BlpI/SacI) had a small effect on overall functionality, reducing silencing by the mature strand to about 80%. The combined BlpI/SacI modification further limited star strand activity. As a result of these studies, a complementary pair of restriction sites (BlpI/SacI) that could be used for cloning foreign sequences into the miR-26b scaffold had been identified.

Figure 6B:
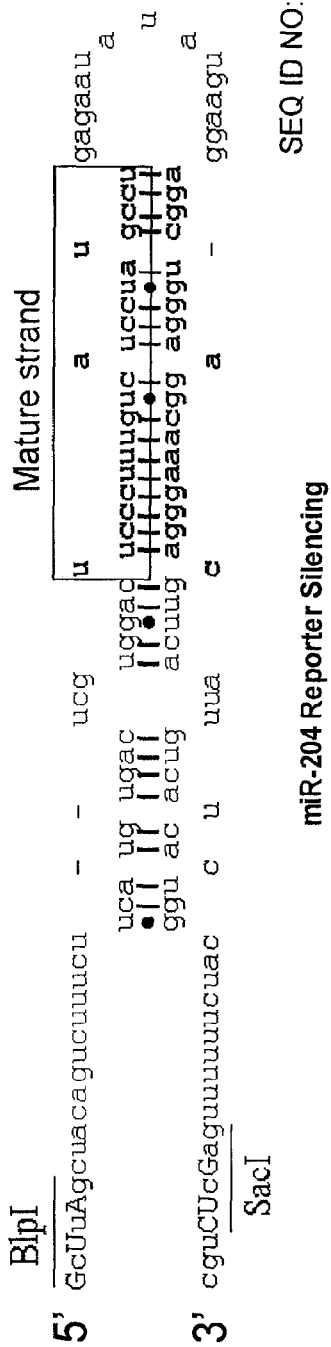
Figure 6B:
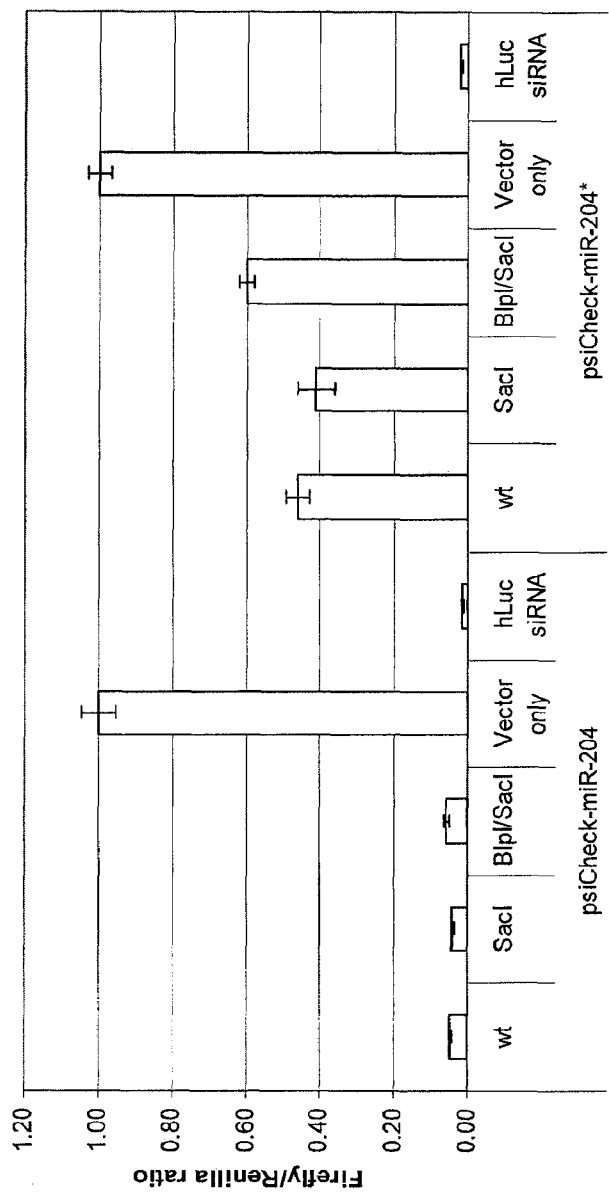
Figure 6C:
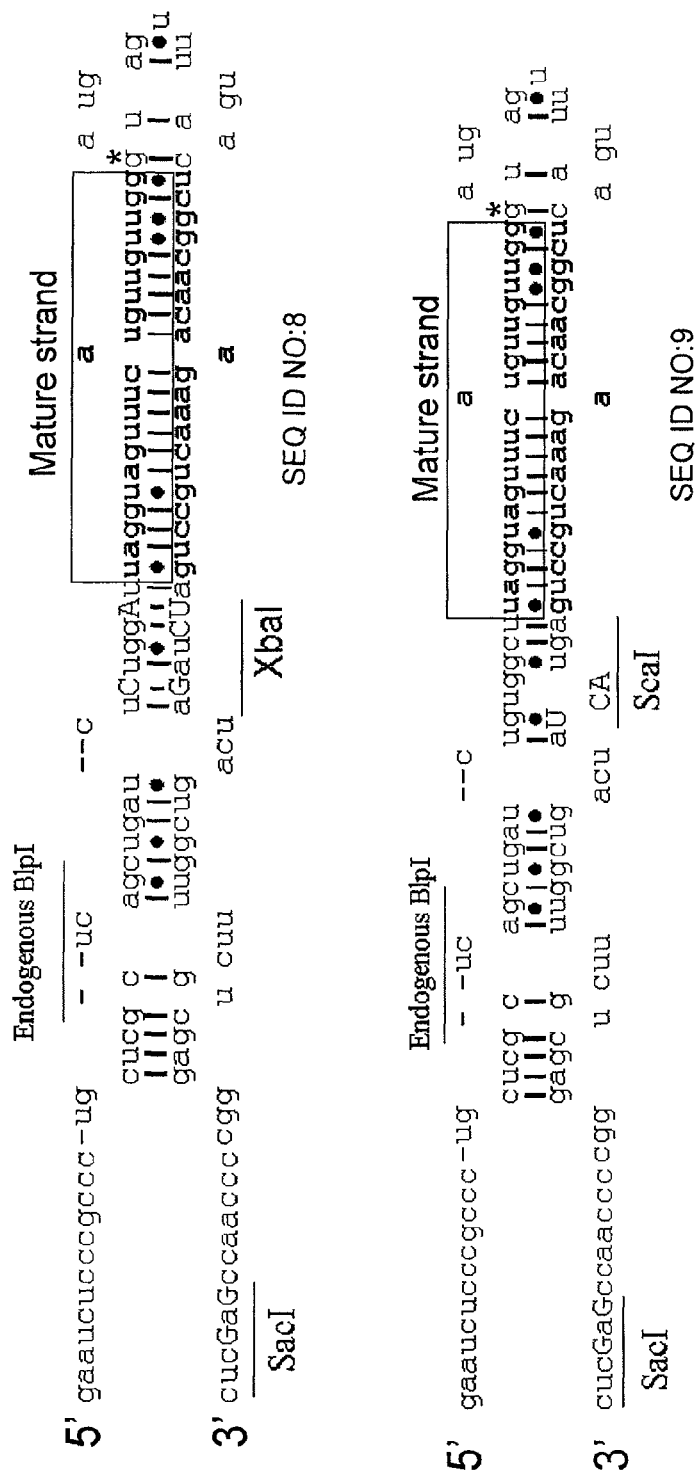

For miR-204, neither the incorporation of the SacI site or the combined SacI/BlpI sites affected mature strand activity (FIG. 6B, bottom). As was observed with the miR-26b construct, modification of the scaffold to incorporate both restriction sites suppressed functionality of the star strand (~60% silencing→~40% silencing). Thus, as a result of these studies, two goals were achieved. First, a complementary pair of restriction sites that could be used for cloning foreign sequences into the miR-204 scaffold had been identified. Secondly, modifications had been identified that further limited the functionality of the miR-204 star strand.

Figure 6D:
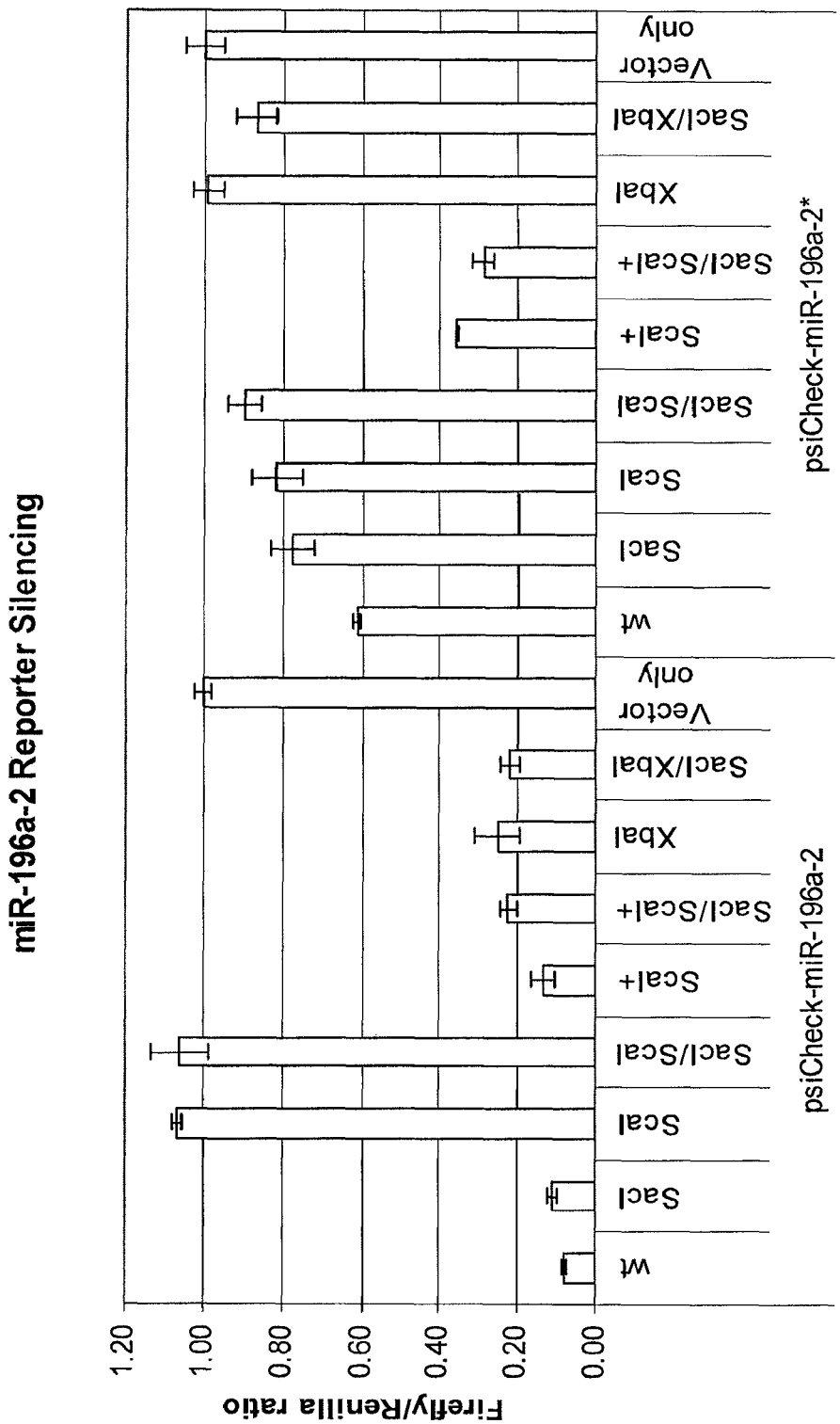
Figure 6E:
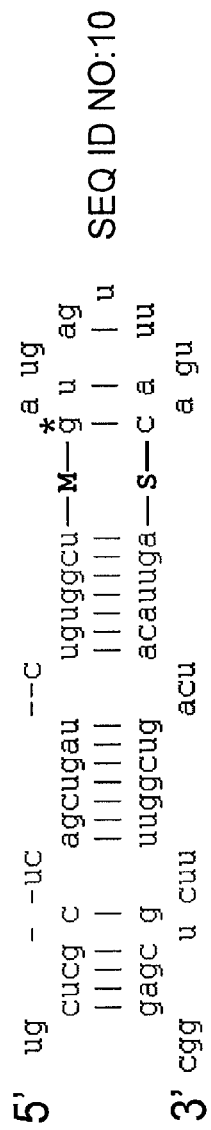
Figure 6E:
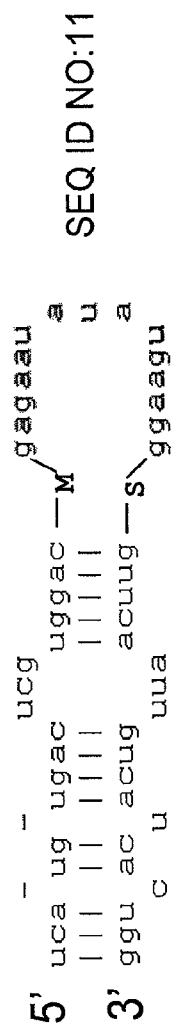
Figure 6G:
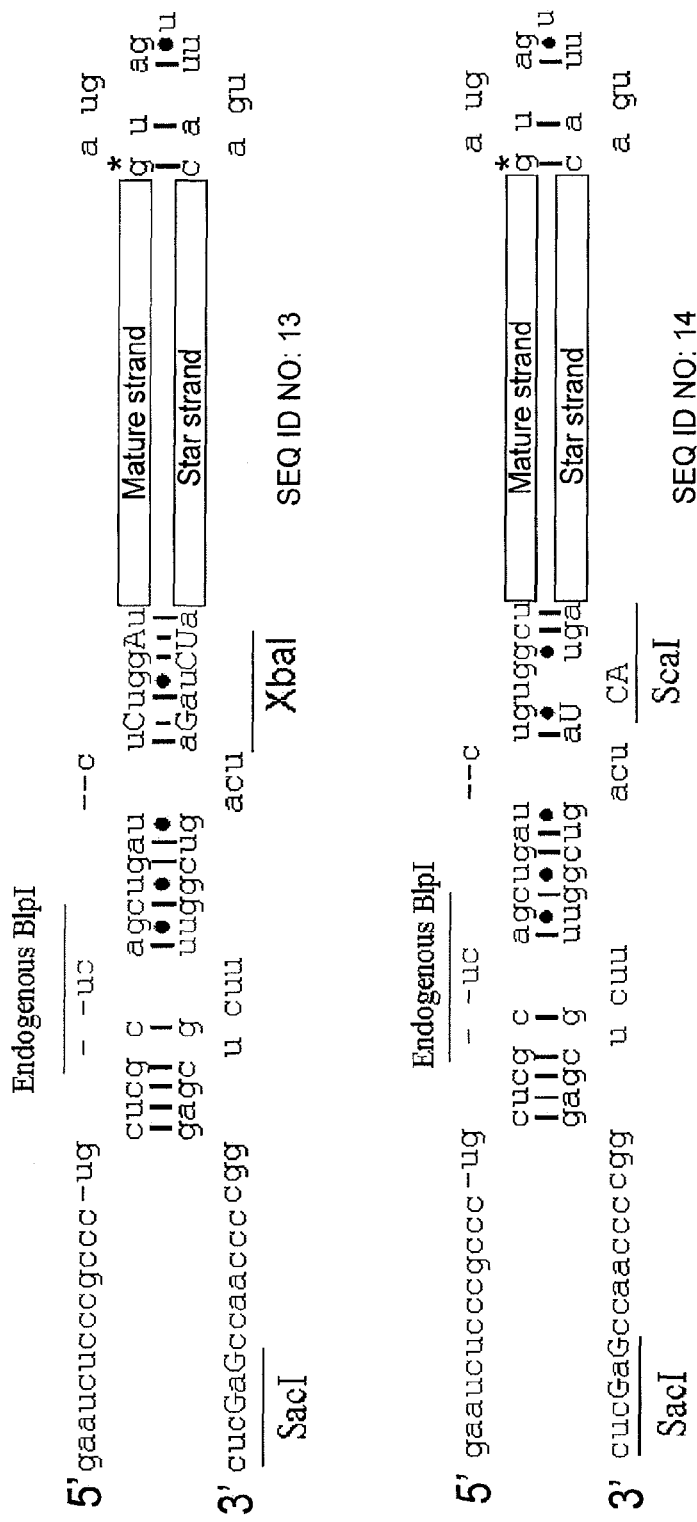

Identifying a combination of restriction sites that were compatible with the miR-196a-2 scaffold (FIG. 6C) was found to be more problematic. As shown in FIG. 6D, addition of a ScaI site (or combination of a ScaI site with a SacI site) significantly decreased the mature strand activity, and both ScaI+ and ScaI+/SacI+ constructs exhibited enhanced activity of the star strand. As enhanced star strand activity is deemed undesirable, this restriction site combination was abandoned.

Fortuitously, incorporation of the SacI site alone had little affect on mature strand activity and further crippled the functionality of the star strand (FIG. 6D, 40% silencing→20% silencing). Thus, as was the case with miR-204, two separate goals were achieved. First, a complementary pair of restriction sites that could be used for cloning foreign sequences into the miR-196a2 scaffold had been identified (Blp1, SacI). Secondly, modifications had been identified that further limited the functionality of the miR-196a-2 star strand.

Example 3

Identifying an miRNA Scaffold that Readily Accepted Foreign Sequences

To determine which of the three preferred miRNA scaffolds most readily accepted foreign sequences, a "walk" of sequences targeting GAPDH were embedded into each of the scaffolds under study and cloned into an artificial intron in GFP. The walk consists of sequences that are 21 bp in length, with the 5' terminus of each consecutive sequence shifted by 2 bp (FIG. 7A). In the case of all three vectors, inserts were (to the best of our abilities) designed to preserve natural secondary structures (e.g. bulges, mismatches) that were present in each of the endogenous scaffolds. In addition, a fourth walk consisting of each sequence embedded in the miR-196a-2 scaffold without secondary structure (i.e. simple hairpins) was performed to better understand the importance of secondary structure in functionality. The results of each of these was compared with results obtained when equivalent synthetic siRNA were transfected into the cells. In addition, the GAPDH target sequence that was embedded into the psiCheck (dual luciferase) reporter is provided in FIG. 7B.

Figure 7C:
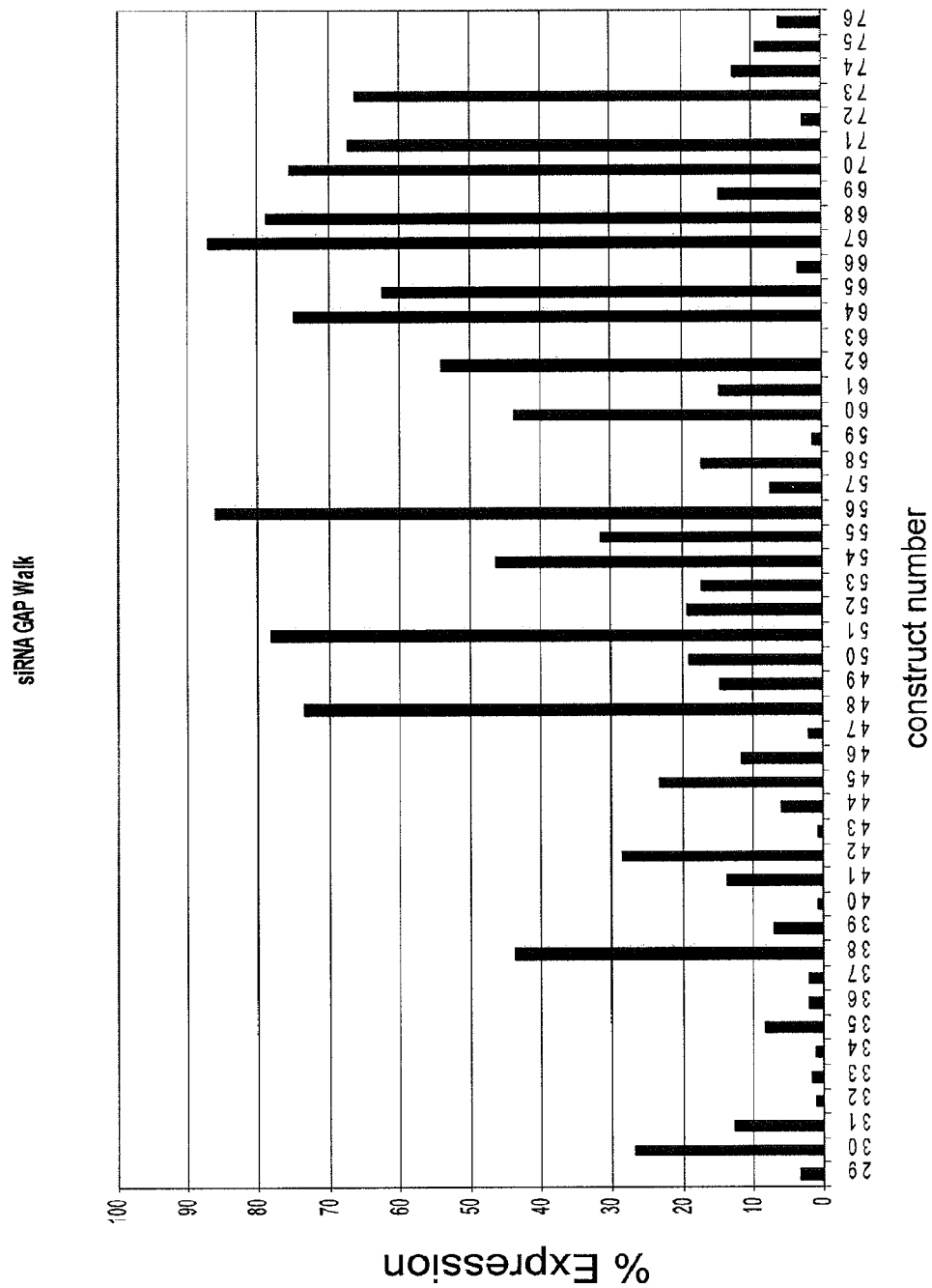
FIG. 7: (A) schematic of sequences used in the GAPDH walk. Sequences used in the GAPDH walk targeted a defined region in the GAPDH gene and represented sequential 2 nt steps across the target region. The sequences representing each target position were synthesize and cloned into the miR-26b, -204, and -196a-2 scaffolds. Note: secondary structure that mimicked the native construct was incorporated into design when possible. (B) GAPDH target sequence that was inserted into the 3'UTR of the hRluc reporter to assess functionality of various sequences. Upper case letters represent the actual targeted sequence. (C) silencing efficiency of the GAPDH walk when sequences are delivered as siRNA. (D) silencing efficiency of each sequence in the GAPDH walk when delivered in the miR-26b scaffold. (E) silencing efficiency of each sequence in the GAPDH walk when delivered in the miR-204 scaffold. (F) silencing efficiency of each sequence in the GAPDH walk when delivered in the miR-196a-2 scaffold. (G) silencing efficiency of each sequence in the GAPDH walk when delivered in the miR-196a-2 scaffold. Secondary structures were not preserved. (H) Bar graph showing the number of sequences that induced knockdown at each level in each backbone. Note: miR-196a-2 hp represents sequences that did not have secondary structure preserved.
Figure 7D:
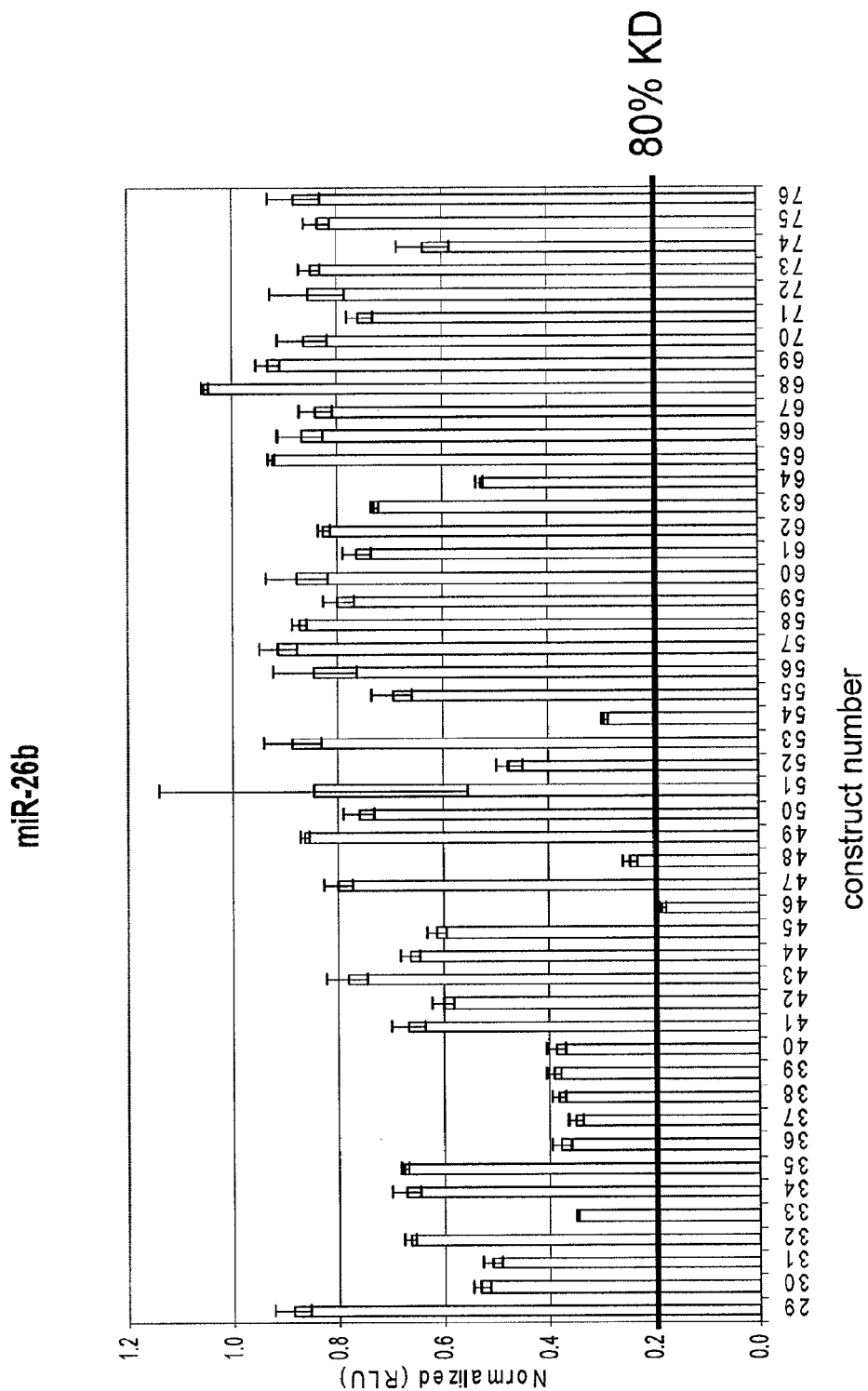
Figure 7E:
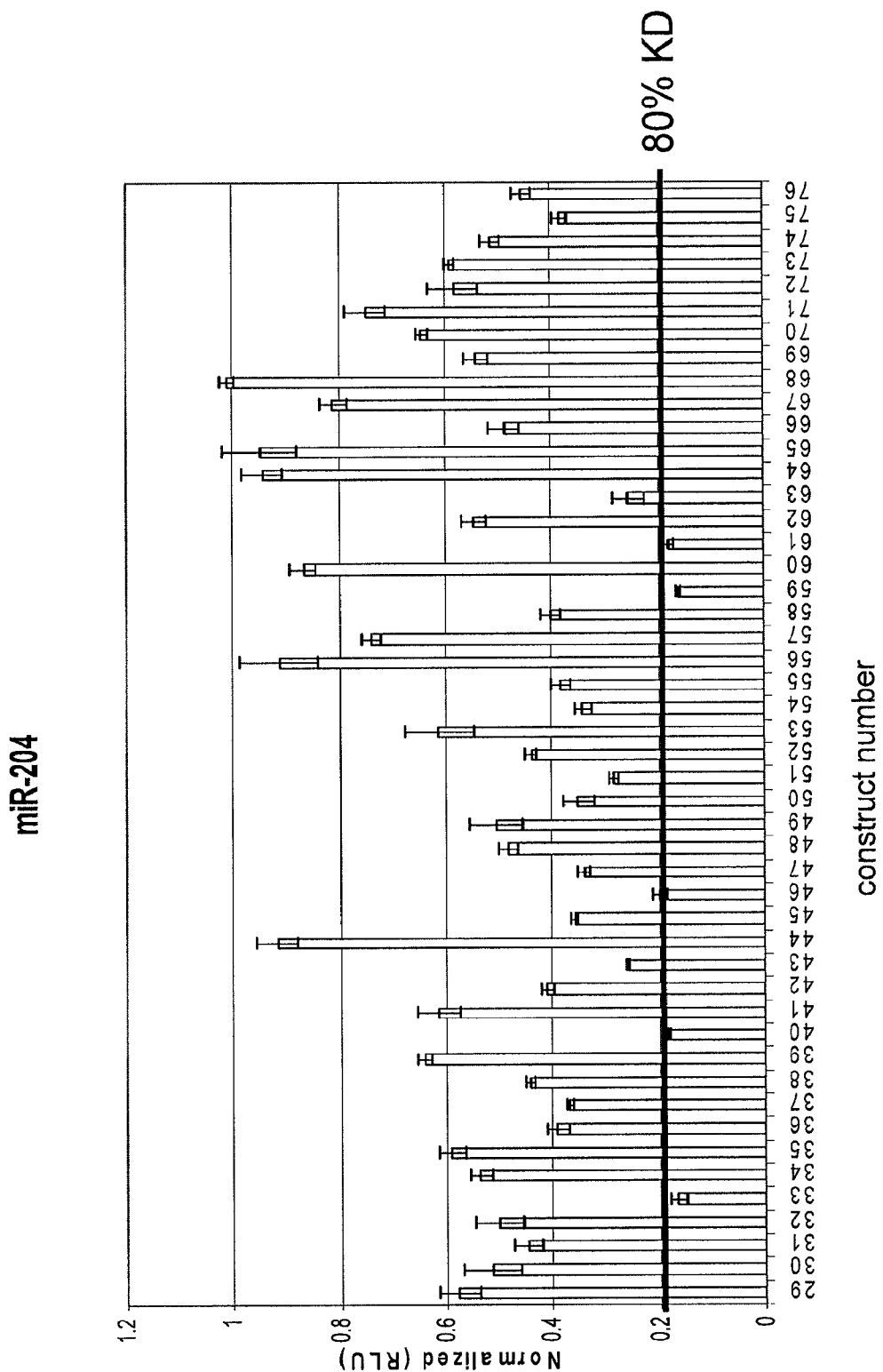
Figure 7F:
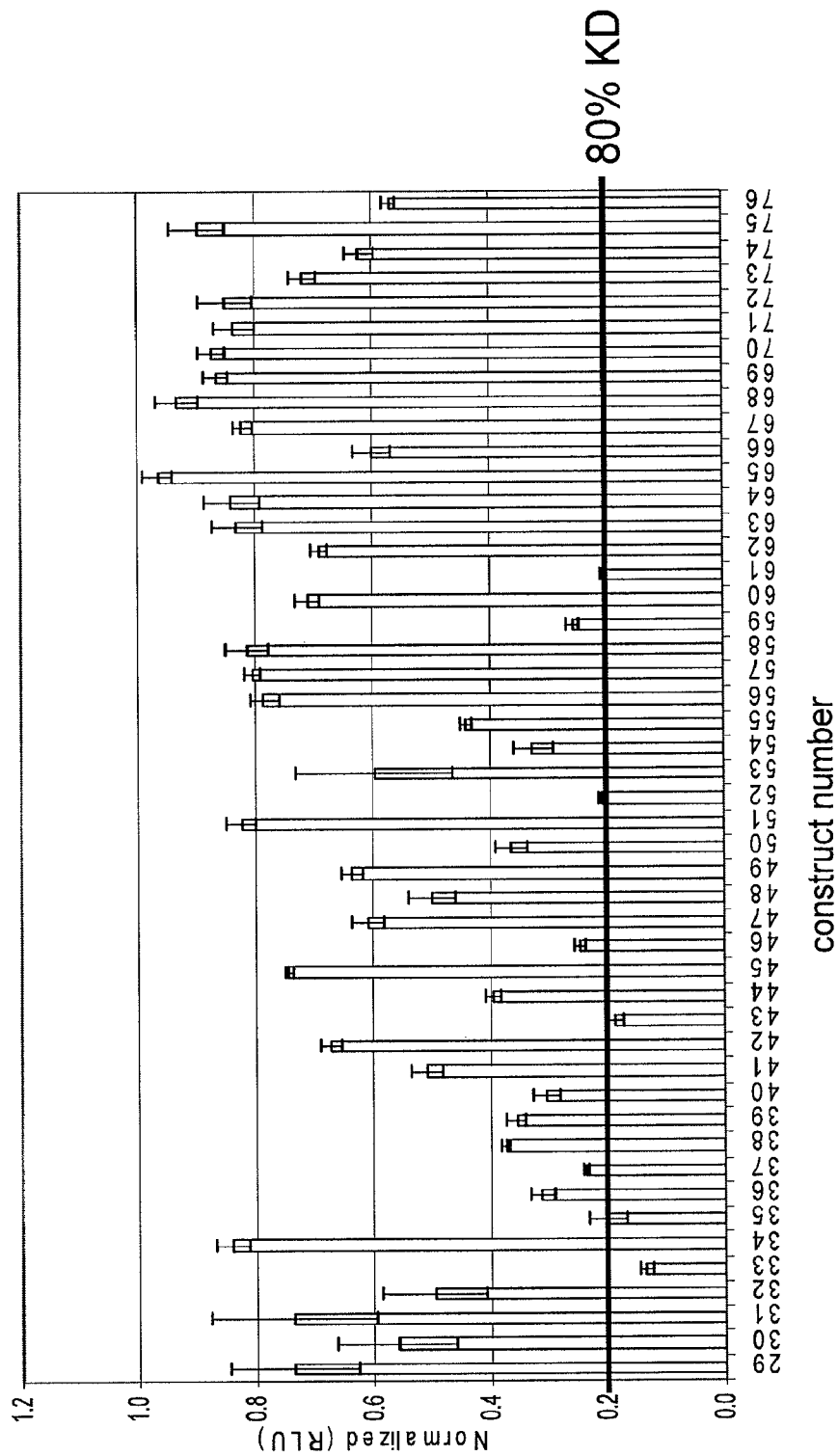
Figure 7G:
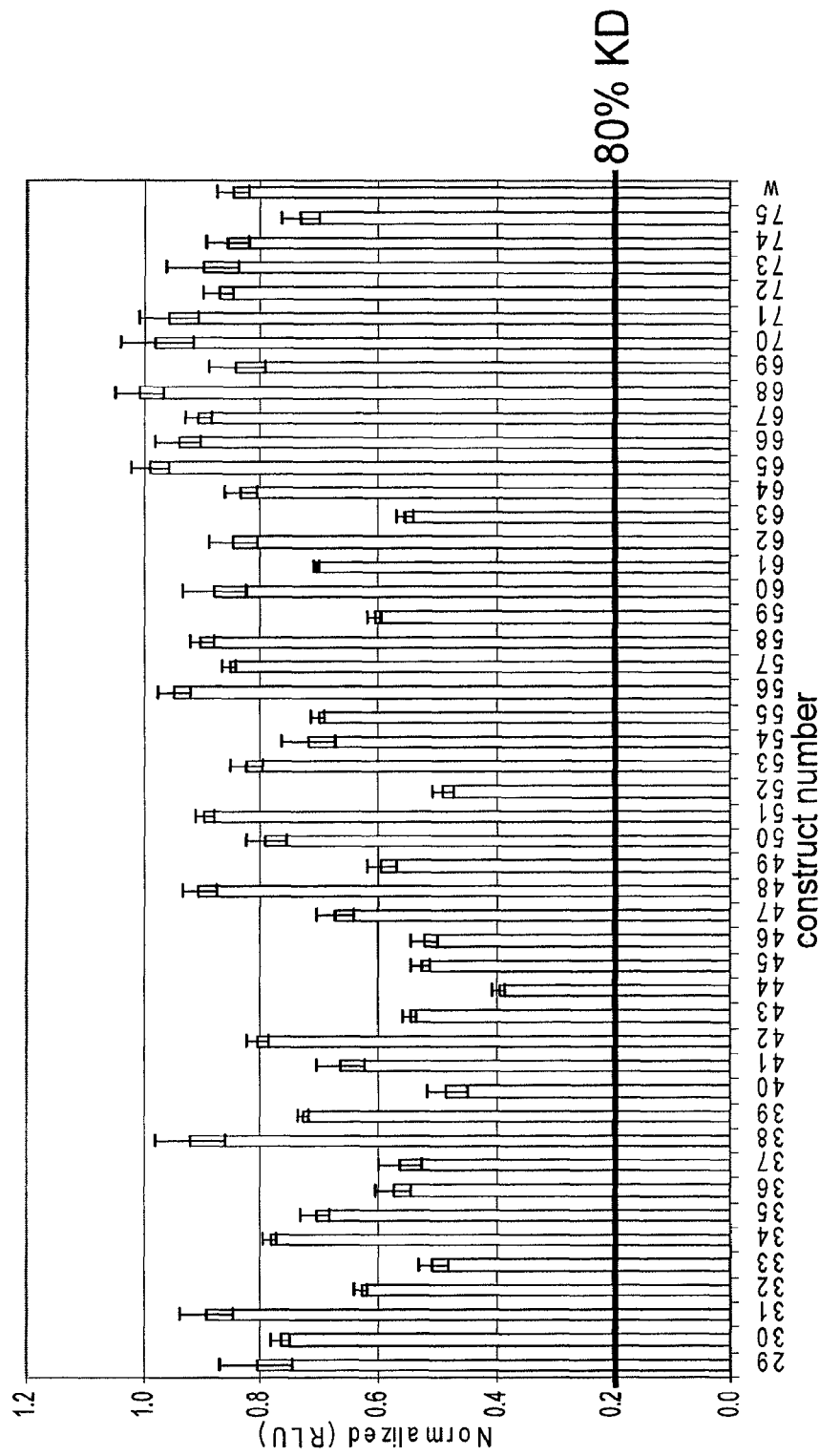
Figure 7H:
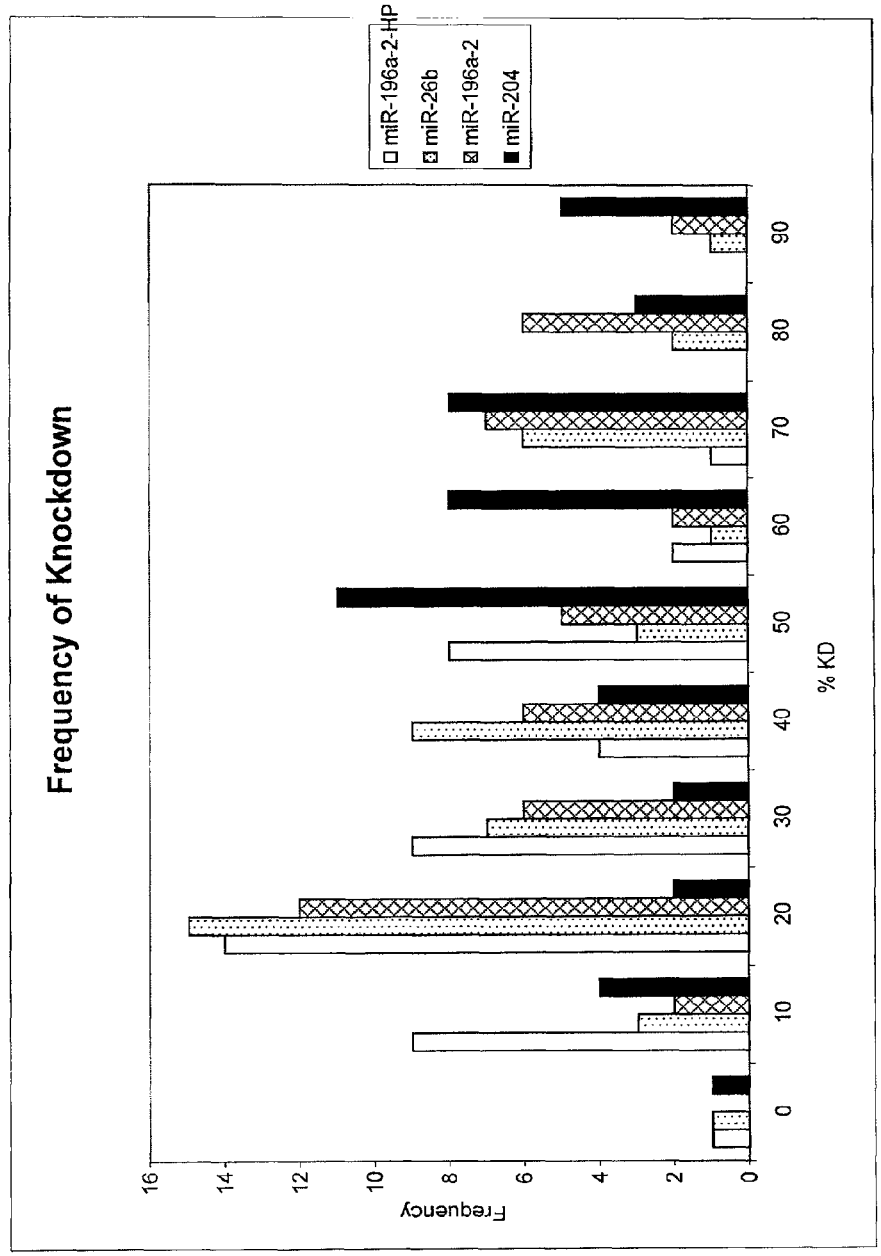

FIG. 7C shows the functionality of each sequence in the walk when it is introduced into the cell as a synthetic 19 bp siRNA. As observed previously, small changes in the position of the targeting siRNA can greatly alter functionality. When those same sequences are introduced into miR-26b, miR-204, and miR-196a-2 and delivered as an expression construct, the latter two scaffolds exhibit greater levels of functionality than the miR-26b scaffold (FIGS. 7 D, E, and F). Interestingly, when all secondary structure was eliminated from sequences incorporated into the miR-196a-2 structure, functionality was found to be greatly suppressed (FIG. 7G). A side-by-side comparison showed that some scaffolds (e.g., miR-196a-2 and -204) provided functionality with a greater number of sequences than other scaffolds (e.g. miR-26b, see FIG. 7H). Together, these findings demonstrate that all three scaffolds (most preferably the miR-204 and miR-196a-2 scaffolds) are useful for delivering foreign sequences and demonstrate that preserving secondary structure is a preferred for optimal functionality.

Example 4

Analysis of Preferred Targeting Sequences

Figure 8A:
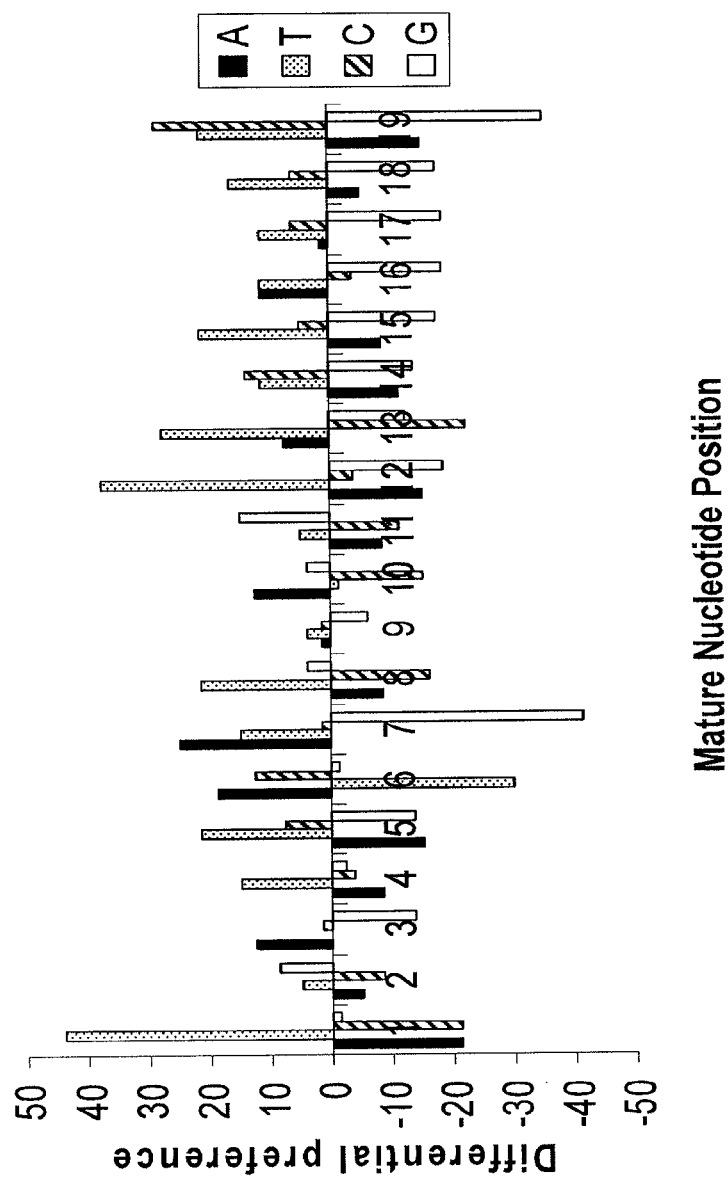
FIG. 8. Desirable Traits for Functional Target Sequences. (A) an analysis of nucleotide prevalence at each position of functional sequences identified nucleotide preferences that could be incorporated into the miR-196a-2 algorithm. Y axis represents differential preference for nucleotides. X axis represents each nucleotide position. (B) a plot of total targeting sequence GC content vs functionality of all sequences in the miR-196a-2 walk. Results show that sequences that contain ten or fewer Gs and Cs in the targeting sequence have a greater tendency to exhibit high performance than sequences with higher numbers of GCs.

Highly functional sequences (>70%) from the miR-196a-2 GAPDH walk were assessed to identify position-specific preferences. When this was performed, it was immediately clear that a "U" at position 1 in the mature strand (a "T" in the DNA encoding that position) was characteristic of highly functional sequences targeting foreign genes. For this reason, this criterion was the first to be identified as desirable for optimal functionality. At position 5 and 6 there was a preference for Ts and As, respectfully. At position 7, few of the functional sequences had a G at this position (FIG. 8A). Position 12, which is the site of a mismatch in the endogenous miR-196a-2, there was an under-representation of "A" and an over-representation of "T". A similar over-representation of "T" was observed in functional sequences at position 13. In this way, site-specific preferences for particular nucleotides were identified.

Further studies were then conducted to identify the importance of each secondary structure. Substituting a mismatch for the GU wobble found at position 1 was observed to be detrimental to overall functionality. Similarly, expanding the size of the mismatch found at position 12 to positions 12 and 13 was also found to be detrimental.

Figure 8B:
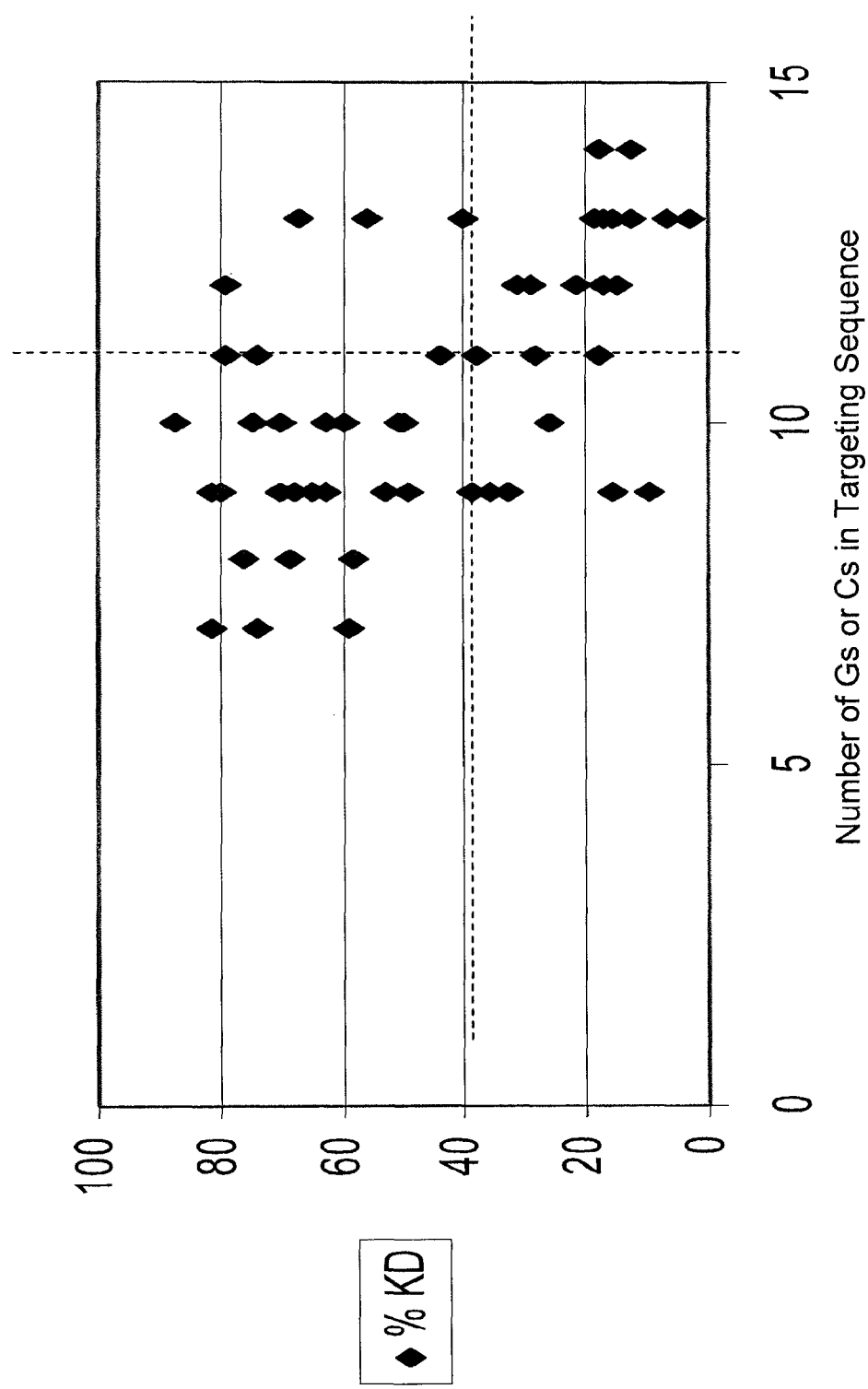

Further analysis of functional and nonfunctional sequences identified strong correlations between functionality and GC content. A comparison of the overall GC content and functionality from the sequences tested in the miR-196a-2 GAPDH walk study showed that in general, the most highly functional sequences had lower GC content. As shown in FIG. 8B, of the 25 sequences having 10 G or C nucleotides or less, 18 (72%) exhibit 50% silencing or greater. In contrast, of the 22 sequences having 11 or more G or C nucleotides, 17 (77%) showed less than 50% silencing, suggesting that overall GC content should be considered in designing foreign sequences to be inserted into the miR-196a-2 scaffold.

Example 5

Comparison of siRNA and shRNA Algorithms

The results obtained from the previous Examples were used to develop an algorithm for identifying target sites that could be targeted efficiently with foreign sequences inserted into the miR-196a-2 scaffold (see Formulas I and II and related descriptions). A side-by-side comparison between target sites identified in the CDC2 gene by the miR-196a-2 algorithm and an algorithm used to design siRNA (see U.S. patent application Ser. No. 10/940,892, filed Sep. 14, 2004, published as U.S. Pat. App. Pub. No. 2005/0255487) show that the two algorithms identify different sequences with very little overlap (see FIG. 9A).

Figure 9D:
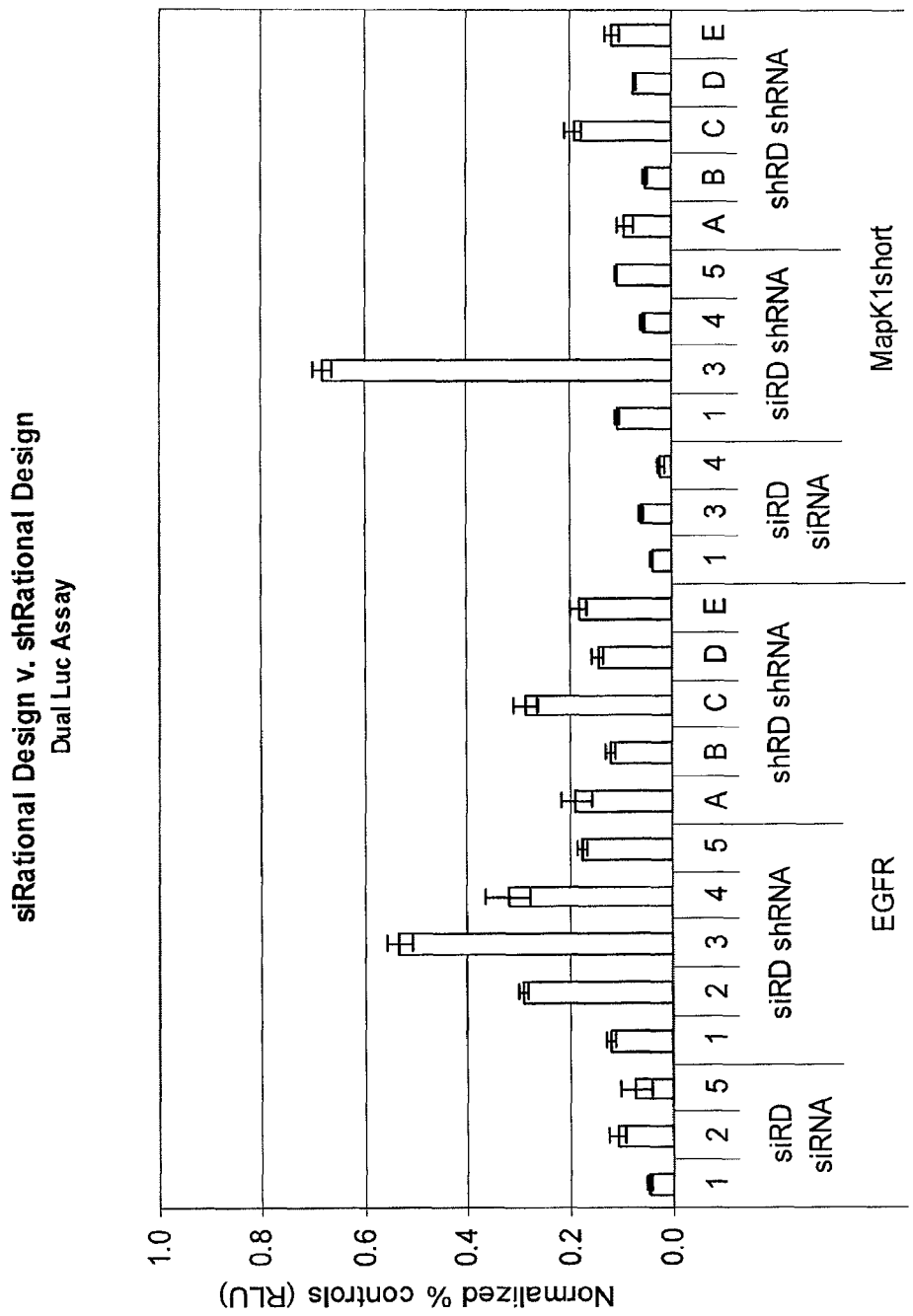
FIG. 9. (A) distinction between targeting sequences chosen by the siRNA rational design algorithm (U.S. patent application Ser. No. 10/940,892, filed Sep. 14, 2004, published as U.S. Pat. App. Pub. No. 2005/0255487) and the miR-196a-2 rational design algorithm. The sequence for the gene CDC2 was run through an siRNA design algorithm and the miR-196a-2 scaffold algorithm. As shown, the two algorithms pick drastically different targeting sequences, thus emphasizing the unrelated nature of the two technologies. (B,C) target sequences for MAPK1 and EGFR that were inserted into the dual luciferase reporter constructs, (D) a comparison of the performance of sequences targeting EGFR and MAPK1 designed with an siRNA algorithm (siRD) vs. sequences designed with the miR-196a-2 algorithm (shRD). Both sets of sequences were cloned into the artificial miR-196a-2 backbone and tested for the ability to knockdown the target gene (hRluc) in the dual luciferase assay. Rationally designed siRNA sequences were 1) converted into shRNAs, and 2) cloned into the miR-196a-2 backbone, were also run for comparison. Note: secondary structure that matched that of the natural miR-196a-2 was included in the siRNA-to-shRNA design. Performance was measured using the dual luciferase reporter assay. (E) Performance of new miR-196a-2 algorithm in targeting additional genes including CDC2, CD28, CD69, and LAT. (F) Sequence of Zap70 target sequence inserted into the 3' UTR hRluc multiple cloning site for the dual luciferase reporter construct, (G) Sequences of four non-functional inserts targeting the Zap70 gene identified a prevalence of GCs in the seed region of the mature strand. Dashed line represents the mature strand sequence (5'→3'), bold underline represents the position of the mature strand seed, solid box line represents GC runs in each sequence. (H) Nearest Neighbor analysis performed on the collection of functional sequences taken from the miR-196a-2 walk shows that as a collection, highly functional sequences have low GC content in the region of the mature strand seed. X-axis represents the position along the mature strand, Y axis represents the differential free-energy preference for functional sequences.

Subsequently, the miR-196a-2 algorithm and the siRNA algorithm were applied to two genes, MAPK1 and EGFR (see FIG. 9B-9C). Targeting sequences were then cloned into the miR-196a-2 scaffold using the previously described restriction sites and co-transfected into HeLa cells along with the appropriate dual luciferase reporter construct (FIG. 9B, C for target sequences). The results are shown in FIG. 9D and show that for EGFR, only two of the five clones selected provided greater than 80% gene knockdown. In contrast, four out of the five clones selected by the new miR-196a-2 algorithm gave >80% knockdown. For MAPK1, three of the four sequences selected by the siRNA algorithm provided >80% knockdown. In contrast, all five clones selected by the new miR-196a-2 algorithm gave >80% knockdown.

Figure 9E:
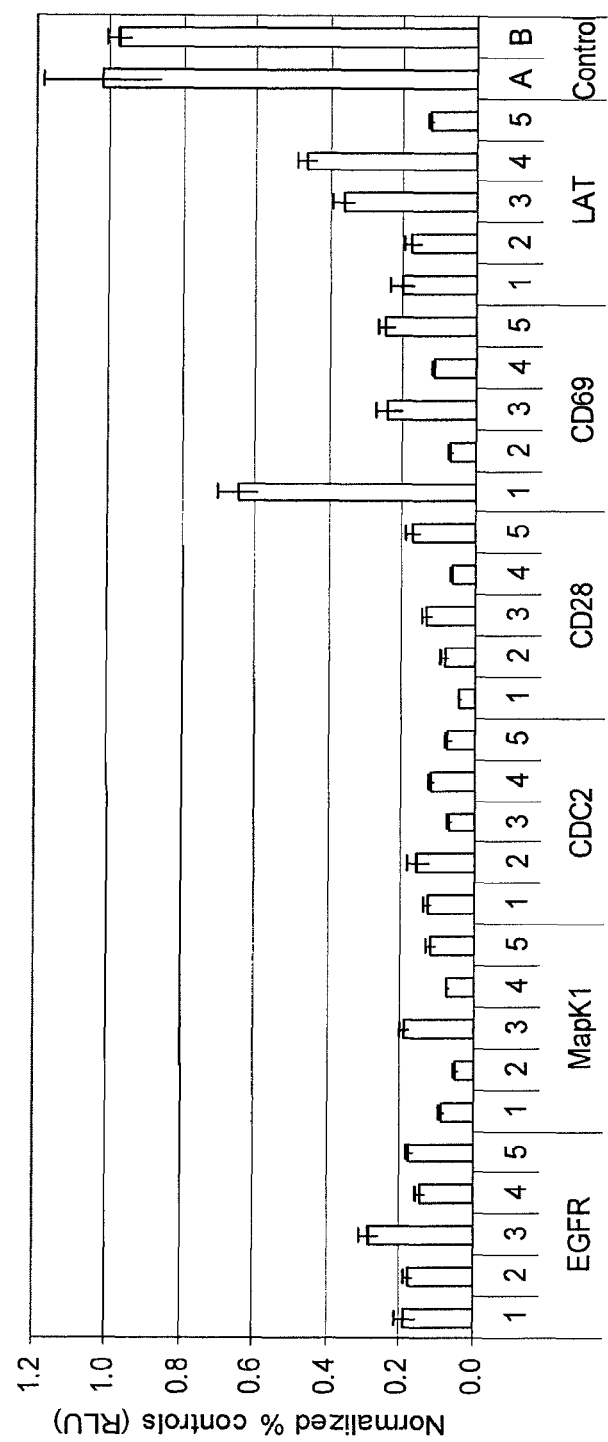

In a further test of the effectiveness of the miR-196a-2 design algorithm, targeting sequences against CDC2 (NM_001786), CD28 (NM_006139), CD69 (NM_001781), and LAT (NM_014387), were designed and cloned into the miR-196a-2 scaffold and subsequently tested for the ability to knockdown the target gene using the dual luciferase assay. The results of these studies are found in FIG. 9E and show that 22 out of the 25 sequences (88%) that were designed using the miR196a-2 algorithm provided greater than 75% silencing.

Figure 9H:
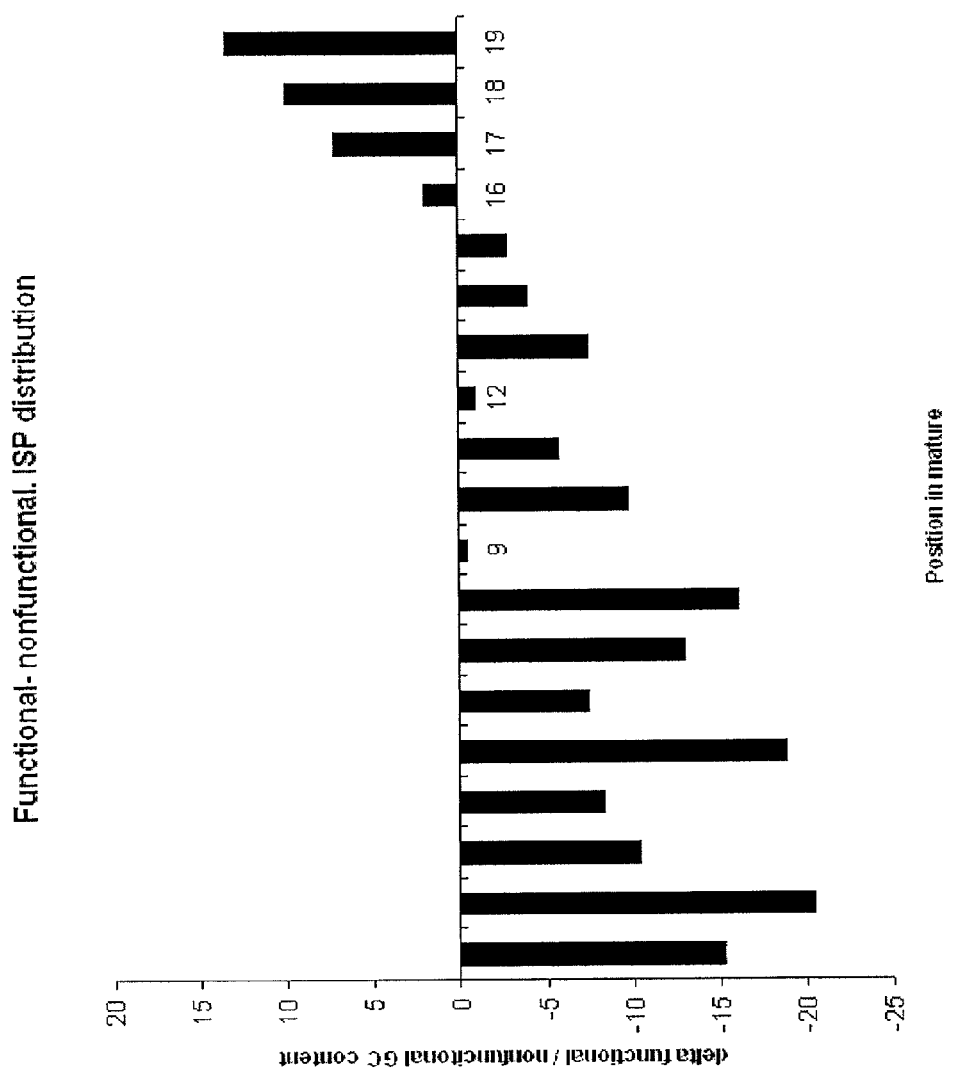

Detailed studies of constructs that failed to provide sufficient knockdown of a target (i.e. <50%, Zap70, FIG. 9F provides target sequence) revealed that a large number of these sequences selected by the algorithms disclosed herein contained strings of Gs and Cs, particularly in the seed region of the mature strand (see FIG. 9G). Subsequent analysis of functional targeting sequences showed that there was a preference for low instability in the mature strand seed region (FIG. 9H). For this reason, additional penalties were incorporated into the miR-196a-2 algorithm to limit GC content in this region.

Table 4 below provides the sequences used in Examples 1-3 (all in 5'→3' direction):

TABLE 4

| | | |
|---|---|---|
| Dual Luc reporter sequences for Screening miRs for functionality | | |
| sense | miR-338 | TCGAATGACCCTTCAACAAAATCACTGATGCTG GAGTCTCGAGCTGC (SEQ ID NO: 50) |
| sense | miR-30c-1 | TCGAATGACCCAGCTGAGAGTGTAGGATGTTT ACACACTCGAGCTGC (SEQ ID NO: 51) |
| sense | miR-26b | TCGAATGACCACAACCTATCCTGAATTACTTGA ACTCTCGAGCTGC (SEQ ID NO: 52) |
| sense | miR-196a-2 | TCGAATGACCTCCCAACAACATGAAACTACCTA AGCTCGAGCTGC (SEQ ID NO: 53) |
| sense | miR-196a-1 | TCGAATGACCGCCCAACAACATGAAACTACCT AATCTCGAGCTGC (SEQ ID NO: 54) |
| sense | miR-30a-5p | TCGAATGACCAGCTTCCAGTCGAGGATGTTTA CAGTCTCGAGCTGC (SEQ ID NO: 55) |
| sense | miR-126* | TCGAATGACCAGCGCGTACCAAAAGTAATAAT GTCCTCGAGCTGC (SEQ ID NO: 56) |
| sense | miR-126 | TCGAATGACCGCGCATTATTACTCACGGTACG AGTCTCGAGCTGC (SEQ ID NO: 57) |
| sense | miR-204 | TCGAATGACCTCAGGCATAGGATGACAAAGGG AAGTCTCGAGCTGC (SEQ ID NO: 58) |
| sense | miR-135a-2 | TCGAATGACCTATCACATAGGAATAAAAAGCCA TAAACTCGAGCTGC (SEQ ID NO: 59) |
| sense | miR-374 | TCGAATGACCAACACTTATCAGGTTGTATTATA ATGCTCGAGCTGC (SEQ ID NO: 60) |
| sense | miR-526a-1 | TCGAATGACCACAGAAAGTGCTTCCCTCTAGA GGGCTCGAGCTGC (SEQ ID NO: 61) |
| sense | miR-486 | TCGAATGACCAGCTCGGGGCAGCTCAGTACAG GATACTCGAGCTGC (SEQ ID NO: 62) |
| Dual Luc reporter sequences for detection of star strand activity | | |
| sense | miR-204 | ggaggctgggaaggcaaagggacgt (SEQ ID NO: 63) |
| sense | miR-26b | ccagcctgttctccattacttggct (SEQ ID NO: 64) |
| sense | miR-196a-2 | actcggcaacaagaaactgcctgag (SEQ ID NO: 65) |
| sense | miR-30a-3p | TCGAATGACCCAGCTGCAAACATCCGACTG AAAGCCCTCGAGCTGC (SEQ ID NO: 66) |
| Artificial Intron | | |
| | | CAGGTAAGTTAGTAGATAGATAGCGTGCTATTTACTAGTCGTAGATCTACAAT GTTGAATTCTCACGCGGCCGCTCTACTAACCCTTCTTTTCTTTCTCTTCCTTT CATCTTTCAGGCG (SEQ ID NO: 67) |
| Probe sequence used for northern blot analysis | | |
| PROBE | miR-196a-2as | CCAACAACATGAAACTACCTA (SEQ ID NO: 68) |
| EGFR and MAPK sequences-siRNA design-sense strand | | |
| S-196a-2-EGFR-1 | | TCAGCTGATCTGTGGCTTTTCGTAGTACATATTTCCTCGATTGA GTTTTGAACGAGGAAATAAGTACTATGAAGAGTTACATCAGTC GGTTTTCGTCGAGGGCCCCAACCGAGCT (SEQ ID NO: 69) |

TABLE 4-continued

| | |
|---|---|
| S-196a-2-EGFR-2 | TCAGCTGATCTGTGGCTAACTGCGTGAGCTTGTTACTCGATTG<br>AGTTTTGAACGAGTAACAACCTCACGTAGTTAGTTACATCAGT<br>CGGTTTTCGTCGAGGGCCCCAACCGAGCT (SEQ ID NO: 70) |
| S-196a-2-EGFR-3 | TCAGCTGATCTGTGGCTCATTGGGACAGCTTGGATCACGATTG<br>AGTTTTGAACGTGGTCCAACCTGTCCTAATGAGTTACATCAGT<br>CGGTTTTCGTCGAGGGCCCCAACCGAGCT (SEQ ID NO: 71) |
| S-196a-2-EGFR-4 | TCAGCTGATCTGTGGCTTCTGTCACCACATAATTACGGGATTG<br>AGTTTTGAACTCGTAATTAAGTGGTGGCAGGAGTTACATCAGT<br>CGGTTTTCGTCGAGGGCCCCAACCGAGCT (SEQ ID NO: 72) |
| S-196a-2-EGFR-5 | TCAGCTGATCTGTGGCTTATTCCGTTACACACTTTGCGGATTG<br>AGTTTTGAACTGTGAAGTGAGTAACGGAATGAGTTACATCAGT<br>CGGTTTTCGTCGAGGGCCCCAACCGAGCT (SEQ ID NO: 73) |
| S_196a-2-MAPK1-1 | TCAGCTGATCTGTGGCTAATTTCTGGAGCCCTGTACCAGATTG<br>AGTTTTGAACTGGTACAGGCGTCCAGGAATTAGTTACATCAGT<br>CGGTTTTCGTCGAGGGCCCCAACCGAGCT (SEQ ID NO: 74) |
| S_196a-2-MAPK1-2 | TCAGCTGATCTGTGGCTCTTGTAAAGATCTGTTTCCATGATTGA<br>GTTTTGAACGTGGAAACACATCTTTGCAAGAGTTACATCAGTC<br>GGTTTTCGTCGAGGGCCCCAACCGAGCT (SEQ ID NO: 75) |
| S_196a-2-MAPK1-3 | TCAGCTGATCTGTGGCTAATAAGTCCAGAGCTTTGGAGGATTG<br>AGTTTTGAACTTTTAAAGCACTGGACTTATTAGTTACATCAGTC<br>GGTTTTCGTCGAGGGCCCCAACCGAGCT (SEQ ID NO: 76) |
| S_196a-2-MAPK1-4 | TCAGCTGATCTGTGGCTAAAGCAAATAGTTCCTAGCTTGATTG<br>AGTTTTGAACGAGTTAGGATCTATTTGCTTTAGTTACATCAGTC<br>GGTTTTCGTCGAGGGCCCCAACCGAGCT (SEQ ID NO: 77) |
| S_196a-2-MAPK1-5 | TCAGCTGATCTGTGGCTTACAATTCAGGTCTTCTTGTGGATTG<br>AGTTTTGAACTATGAGAAGTCCTGAATTGTGAGTTACATCAGTC<br>GGTTTTCGTCGAGGGCCCCAACCGAGCT (SEQ ID NO: 78) |
| EGFR and MAPK sequences-shRNA design-sense strand | |
| EGFR A | TGATCTGTGGCTTATTCGTAGCATTTATGGAGGGATTGAGTTTT<br>GAACTCTTCATAATTGCTACGAATGAGTTACATCAGTCGGTTTT<br>CG (SEQ ID NO: 79) |
| EGFR B | TGATCTGTGGCTTCGTAGTACATATTTCCTCGGGATTGAGTTTT<br>GAACTCGGGGAAAAATGTACTACGGAGTTACATCAGTCGGTTT<br>TCG (SEQ ID NO: 80) |
| EGFR C | TGATCTGTGGCTTCGTCTCGGAATTTGCGGCGGGATTGAGTTT<br>TGAACTCGTCGCAATTTCCGAGACGGAGTTACATCAGTCGGTT<br>TTCG (SEQ ID NO: 81) |
| EGFR D | TGATCTGTGGCTTACGGTTTTCAGAATATCCGGGATTGAGTTTT<br>GAACTCGGATATTGTGAAAATCGTGAGTTACATCAGTCGGTTT<br>TCG (SEQ ID NO: 82) |
| EGFR E | TGATCTGTGGCTTCCGGTTTTATTTGCATCAGGGATTGAGTTTT<br>GAACTCTGATGCATATAAAATCGGGAGTTACATCAGTCGGTTT<br>TCG (SEQ ID NO: 83) |
| MAPK1 A | TGATCTGTGGCTTTGCTCGATGGTTGGTGCTGGGATTGAGTTT<br>TGAACTCGGCACCATCCATCGGGCAGAGTTACATCAGTCGGT<br>TTTCG (SEQ ID NO: 84) |
| MAPK1 B | TGATCTGTGGCTTCGAACTTGAATGGTGCTTGGGATTGAGTTT<br>TGAACTCGGGCACCTTTCAAGTTCGGAGTTACATCAGTCGGTT<br>TTCG (SEQ ID NO: 85) |
| MAPK1 C | TGATCTGTGGCTTACTCGAACTTTGTTGACAGGGATTGAGTTT<br>TGAACTCTGTCAACTAAGTTCGAGTGAGTTACATCAGTCGGTT<br>TTCG (SEQ ID NO: 86) |
| MAPK1 D | TGATCTGTGGCTTCGTAATACTGCTCCAGATGGGATTGAGTTT<br>TGAACTCGTCTGGACCAGTATTACGGAGTTACATCAGTCGGTT<br>TTCG (SEQ ID NO: 87) |
| MAPK1 E | TGATCTGTGGCTTCCATGAGGTCCTGTACTAGGGATTGAGTTT<br>TGAACTCTGGTACACGACCTCGTGGGAGTTACATCAGTCGGTT<br>TTCG (SEQ ID NO: 88) |

Example 6

Compatibility of the miR-196a-2 Scaffold with Endogenous miRNAs

To determine whether the miR-196a-2 scaffold could be used as a delivery platform for expression of endogenous miRNAs, eleven separate endogenous mature strand sequences (miR-499-5p, miR-499-3p, -208a, -9, -34a, -30-3p, -132, -26b, -124, -208b, 122a) were cloned into the miR-196a-2 scaffold present in the pG19SM6 expression plasmid. The resulting constructs are examples of shMIMICs as they comprise a scaffold from a first miRNA and a mature strand sequence from a second miRNA. The constructs had the following features: 1) the length of the incorporated sequence was 19-23 nucleotides, 2) the mismatch at position 12 was preserved, and 3) the nucleotide at position 1 of the mature strand was always U (i.e., if the nucleotide at position 1 of the mature strand of the endogenous miRNA was not U, then it was altered to U in the shMIMIC). Additionally, a G:U wobble was created on the star strand in positions 5, 18, 19 and 21 when possible to maintain the secondary structure of the scaffold. A list of the sequences cloned into the pG19SM6 expression plasmid is provided in Table 5 (lowercase nucleotides indicate positions that were modified so that position 1 of the mature strand would be a U in the expressed mature strand). Sequences were cloned into the expression vector as described previously.

To test the effectiveness of each miRNA to function in the context of the miR-196a-2 scaffold, each individual miR-196a-2 expression cassette containing a unique endogenous miRNA sequence was co-transfected into cells along with a dual luciferase construct containing the appropriate miR target site inserted into the 3' UTR of the humanized Rluc gene (conditions described in previous examples). Cells were the cultured and the ratio of Rluc to Fluc was determined.

Figure 10:
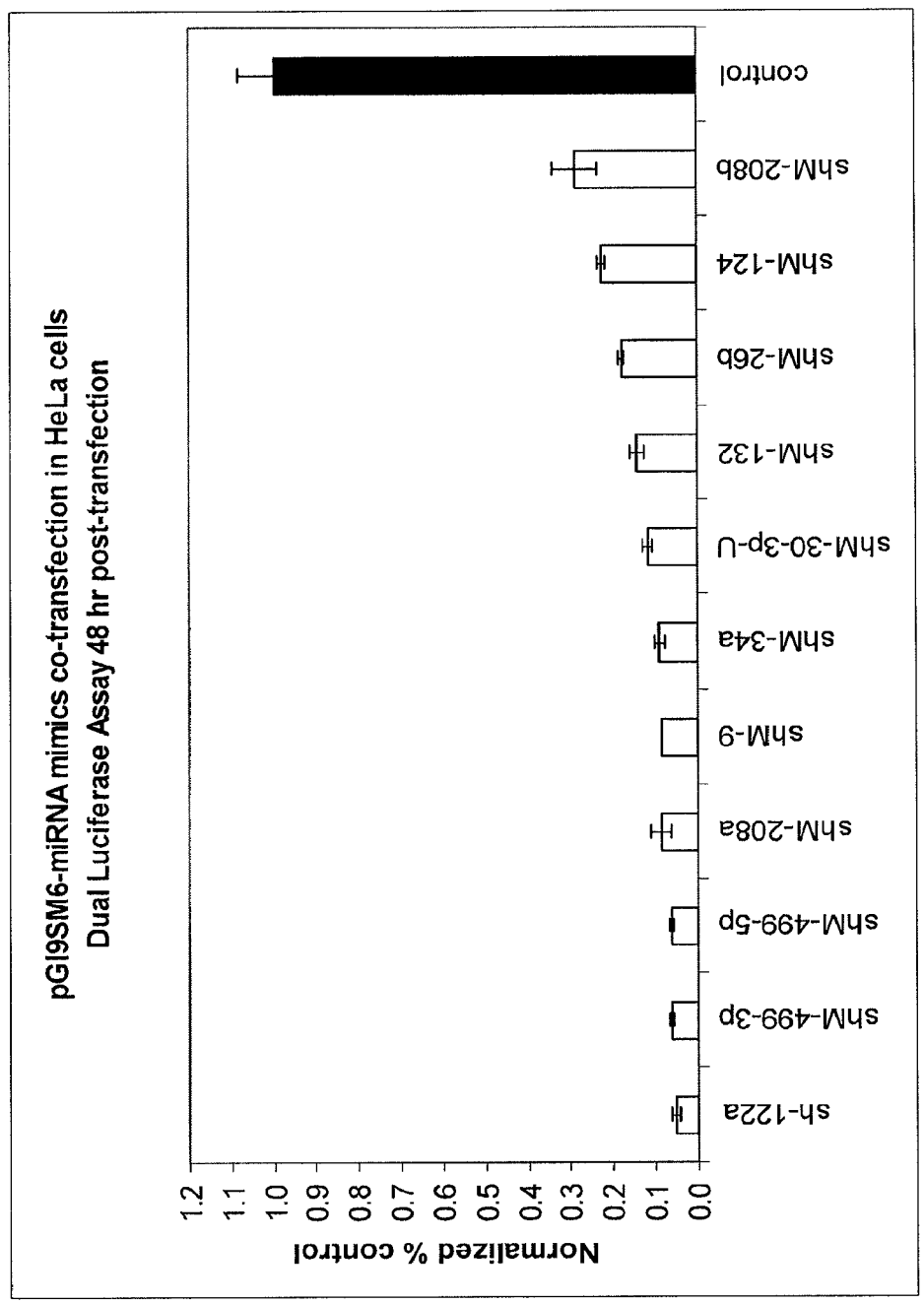
FIG. 10. The graph depicted shows the functionality of multiple endogenous miRNA sequences when inserted into the miR-196a-2 scaffold to form a miR-196a-2 shMIMIC. Native sequences were cloned into the miR-196a-2 scaffold, preserving secondary structures and some sequence preferences associated with endogenous miR-196a-2 microRNA. All constructs demonstrate 70% silencing or better.

Results of these studies demonstrate that the miR-196a-2 scaffold can be used to efficiently deliver endogenous miRNA sequences to cells. As shown in FIG. 10 all of the constructs tested induced 70% or greater silencing of the dual luciferase reporter construct. These results demonstrate the applicability of the miR-196a-2 scaffold as a delivery system for endogenous miRNAs.

Experiments have also been performed where the length of the inserted miRNA sequence was tested at 19 base pairs (e.g., a 22 nt mature sequence was truncated at the 3' end to 19 nt and cloned into the scaffold; see the miR-106b and miR-1 cloned sequences in Table 5). In all cases, truncation of the sequence to 19 nts had no effect on the ability to silence the respective reporter construct. Thus, this demonstrates that the miR-196a-2 scaffold can readily adapt to foreign miRNA sequences of 19-23 nts in length. Furthermore, the ability of the miR-196a-2 scaffold to effectively deliver eleven unique miRNA sequences demonstrates its general applicability to

TABLE 5

List of mature miRNA sequences cloned into the miR-196a-2 scaffold

| microRNA | Endogenous mature strand | mature strand length | oligo cloned | length of cloned oligo |
|---|---|---|---|---|
| miR-1 | UGGAAUGUAAAGAAGUAUGAU (SEQ ID NO: 89) | 22 | TGGAATGTAAAGAAGTATG (SEQ ID NO: 90) | 19 |
| miR-106b | UAAAGUGCUGACAGUGCAGAU (SEQ ID NO: 91) | 21 | TAAAGTGCTGACAGTGCAG (SEQ ID NO: 92) | 19 |
| miR-122a | UGGAGUGUGACAAUGGUGUUUG (SEQ ID NO: 93) | 22 | TGGAGTGTGACAATGGTGTTTG (SEQ ID NO: 94) | 22 |
| miR-124 | UAAGGCACGCGGUGAAUGCC (SEQ ID NO: 95) | 20 | TAAGGCACGCGGTGAATGCC (SEQ ID NO: 96) | 20 |
| miR-132 | UAACAGUCUACAGCCAUGGUCG (SEQ ID NO: 97) | 22 | TAACAGTCTACAGCCATGGTCG (SEQ ID NO: 98) | 22 |
| miR-26b | UUCAAGUAAUUCAGGAUAGGU (SEQ ID NO: 99) | 21 | TTCAAGTAATTCAGGATAGGT (SEQ ID NO: 100) | 21 |
| miR-30a-3p-U | CUUUCAGUCGGAUGUUUGCAGC (SEQ ID NO: 101) | 22 | tTTTCAGTCGGATGTTTGCAGC (SEQ ID NO: 102) | 22 |
| miR-34a | UGGCAGUGUCUUAGCUGGUUGU (SEQ ID NO: 103) | 22 | TGGCAGTGTCTTAGCTGGTTGT (SEQ ID NO: 104) | 22 |
| miR-9 | UCUUUGGUUAUCUAGCUGUAUGA (SEQ ID NO: 105) | 23 | TCTTTGGTTATCTAGCTGTATGA (SEQ ID NO: 106) | 23 |
| miR-208a | AUAAGACGAGCAAAAAGCUUGU (SEQ ID NO: 107) | 22 | tTAAGACGAGCAAAAAGCTTGT (SEQ ID NO: 108) | 22 |
| miR-208b | AUAAGACGAACAAAAGGUUUGU (SEQ ID NO: 109) | 22 | tTAAGACGAACAAAAGGTTTGT (SEQ ID NO: 110) | 22 |
| miR-499-3p | AACAUCACAGCAAGUCUGUGCU (SEQ ID NO: 111) | 22 | tACATCACAGCAAGTCTGTGCT (SEQ ID NO: 112) | 22 |
| miR-499-5p | UUAAGACUUGCAGUGAUGUUU (SEQ ID NO: 113) | 21 | TTAAGACTTGCAGTGATGTTT (SEQ ID NO: 114) | 21 | all miRNAs from any species including human, mouse, rat, and *C. elegans*. Mature miRNA sequences that can be incorporated into the miR-196a-2 scaffold can be found at miR- Base (at the http site for microrna.sanger.ac.uk/sequences/). FIG. 11 provides general design considerations for shMIM-ICs based on the miR-196a-2 scaffold.

What is claimed is:

1. A method of delivery of a mature endogenous miRNA to a cell, the method comprising:
introducing in said cell a non-naturally occurring miR-196a-2 miRNA, wherein said non-naturally occurring miR-196a-2 miRNA comprises a nucleic acid having a stem-loop structure, wherein the stem of the stem-loop structure incorporates a miRNA-196a-2 scaffold, and a mature strand-star strand duplex, wherein said mature strand has a sequence derived from a mature endogenous miRNA, wherein said mature endogenous miRNA has a sequence that is distinct from the sequence of the endogenous mature strand of miR-196a-2, wherein position 1 of the mature strand is U and the opposite nucleotide in the star strand is G and the duplex contains a mismatch at position 12 of the mature strand and either no additional mismatches or wobble pairs at any position other than positions 1 and 12 of the mature strand, or mismatches or wobble pairs at one or more of positions other than at positions 2, 3, 4, 6, 7, 8, 9, 10, 11, 13, 14, 15, 16 and 17 within the duplex, wherein positions of the mature strand are numbered relative to the 5' end of the mature strand, and the mature strand is about 19-25 nucleotides in length;
wherein said non-naturally occurring miR-196a-2 miRNA is processed in said cell to yield a mature miRNA having the sequence of said mature strand.

2. The method of claim 1, wherein said non-naturally occurring miR-196a-2 comprises (SEQ ID NO: 10):

```
5' -ug       - -uc      --c      a  ug
     cucg c    agcugau  uguggcu--M--g u  ag
     |||| |    |||||||  |||||||     | |  |  u
     gagc g    uuggcug  acauuga--S--c a  uu
3' cgg     u  cuu       acu      a  gu
``` wherein M is said mature strand and wherein S is said star strand.

3. The method of claim 1, wherein said introducing comprises contacting the cell with a vector capable of expressing the non-naturally occurring miR-196a-2 miRNA.

4. The method of claim 3, wherein the vector is a lentiviral vector.

5. The method of claim 1, wherein said introducing comprises providing a recombinant expression vector, wherein the expression vector comprises a nucleotide sequence that encodes the non-naturally occurring miR-196a-2 miRNA.

6. The method of claim 1, wherein the mature strand is 19-23 nucleotides in length.

7. The method of claim 1, wherein the non-naturally occurring miR-196a-2 miRNA comprises a mismatch or wobble pair at one or more of positions 5, 18, 19, 20, or 21 of the mature strand.

8. The method of claim 1, wherein the nucleotide at position 12 of the mature strand is the same as the nucleotide at the opposite position of the star strand.

9. The method of claim 5, wherein the nucleotide at position 12 of the mature strand is the same as the nucleotide at the opposite position of the star strand.

10. The method of claim 6, wherein the nucleotide at position 12 of the mature strand is the same as the nucleotide at the opposite position of the star strand.

11. The method of claim 7, wherein the nucleotide at position 12 of the mature strand is the same as the nucleotide at the opposite position of the star strand.

12. The method of claim 1, wherein said introducing is by transfection.

* * * * *